(12) United States Patent
Steiling et al.

(10) Patent No.: US 9,677,138 B2
(45) Date of Patent: Jun. 13, 2017

(54) METHODS AND SYSTEMS FOR MONITORING, DIAGNOSING, AND TREATING CHRONIC OBSTRUCTIVE PULMONARY DISEASE

(71) Applicants: Trustees of Boston University, Boston, MA (US); THE BRITISH COLUMBIA CANCER AGENCY BRANCH, Vancouver (CA)

(72) Inventors: Katrina Steiling, Boston, MA (US); Avrum Spira, Newton, MA (US); Marc Lenberg, Brookline, MA (US); Stephen Lam, Vancouver (CA)

(73) Assignees: TRUSTEES OF BOSTON UNIVERSITY, Boston, MA (US); THE BRITISH COLUMBIA CANCER AGENCY BRANCH, Vancouver (CA)

( * ) Notice: Subject to any disclaimer, the term of this patent is extended or adjusted under 35 U.S.C. 154(b) by 0 days.

(21) Appl. No.: 14/402,607

(22) PCT Filed: May 20, 2013

(86) PCT No.: PCT/US2013/041857
§ 371 (c)(1),
(2) Date: Nov. 20, 2014

(87) PCT Pub. No.: WO2013/177060
PCT Pub. Date: Nov. 28, 2013

(65) Prior Publication Data
US 2015/0240306 A1    Aug. 27, 2015

Related U.S. Application Data

(60) Provisional application No. 61/649,355, filed on May 20, 2012, provisional application No. 61/725,391, filed on Nov. 12, 2012.

(51) Int. Cl.
| | | |
|---|---|---|
| *C12Q 1/68* | (2006.01) | |
| *A61K 31/137* | (2006.01) | |
| *A61K 31/198* | (2006.01) | |
| *A61K 31/357* | (2006.01) | |
| *A61K 31/46* | (2006.01) | |
| *A61K 31/522* | (2006.01) | |
| *A61K 31/53* | (2006.01) | |
| *A61K 31/5377* | (2006.01) | |
| *A61K 31/56* | (2006.01) | |
| *A61K 31/575* | (2006.01) | |
| *A61K 31/58* | (2006.01) | |
| *A61K 38/06* | (2006.01) | |

(52) U.S. Cl.
CPC .......... *C12Q 1/6883* (2013.01); *A61K 31/137* (2013.01); *A61K 31/198* (2013.01); *A61K 31/357* (2013.01); *A61K 31/46* (2013.01); *A61K 31/522* (2013.01); *A61K 31/53* (2013.01); *A61K 31/5377* (2013.01); *A61K 31/56* (2013.01); *A61K 31/575* (2013.01); *A61K 31/58* (2013.01); *A61K 38/06* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 7,368,531 B2 * | 5/2008 | Rosen et al. | 530/350 |
| 2009/0186951 A1 * | 7/2009 | Brody | C12Q 1/6886 514/734 |

FOREIGN PATENT DOCUMENTS

| | | |
|---|---|---|
| EP | 1394274 A2 | 3/2004 |
| WO | 2007/103541 A3 | 9/2007 |
| WO | 2007/147265 A1 | 12/2007 |
| WO | 2008/051260 A1 | 5/2008 |
| WO | 2009/039457 A1 | 3/2009 |
| WO | 2010/020058 A1 | 2/2010 |
| WO | 2011/093813 A1 | 8/2011 |

OTHER PUBLICATIONS

Tilley et al. (2009) Down-regulation of the Notch Pathway in Human Airway Epithelium in Association with Smoking and Chronic Obstructive Pulmonary Disease. American Journal of Respiratory and Critical Care Medicine, 179:457-466.*
Ohtaki et al. (2010) A robust method for estimating gene expression states using Affymetrix microarray probe level data. BMC Bioinformatics, 11:183, pp. 1-14.*
Buck et al. (1999) Design Strategies and Performance of Custom DNA Sequencing Primers. Biotechniques, 27:528-536.*
Sambrook et al. (2001), Molecular Cloning: A laboratory manual,. 3rd ed, Cold Spring Harbor Laboratory Press, New York, pp. 7.1-7.3, 7.42-7.45, and 9.3.*
Affymetrix HG-U133 Plus 2.0 Annotation File (filtered excerpt, accessed from: <http://www.affymetrix.com/Auth/analysis/downloads/na26/ivt/HG-U133_Plus_2.na26.annot.csv.zip> on Mar. 18, 2013, 2 pages.*
Stahlberg et al. (2004) Properties of the Reverse Transcription Reaction in mRNA Quantification. Clinical Chemistry, 50(3):509-515, and data supplement, 5 pages.*

(Continued)

*Primary Examiner* — Neil P Hammell
(74) *Attorney, Agent, or Firm* — Arrigo, Lee & Guttman LLP

(57) ABSTRACT

A novel set of 98 genes expressed in the respiratory tract epithelium that serve as biomarkers for measuring chronic obstructive pulmonary disease (COPD) activity are provided. Methods of classifying the (COPD) status of a subject are provided. Systems for expression-based classification of COPD disease status are provided. Methods of treating COPD are also provided, among other things.

17 Claims, 25 Drawing Sheets

(56) References Cited

OTHER PUBLICATIONS

Steiling et al. (2009) Airway Gene Expression in Chronic Obstructive Pulmonary Disease. Proceedings of the American Thoracic Society, 6:697-700.*

Soumyaroop Bhattacharya et al., Molecular Biomarkers for Quantitative and Discrete COPD Phenotypes, Am J Respir Cell Mol Biol vol. 40. pp. 359-367, 2009.

Joshua D Campbell et al., "A gene expression signature of emphysema-related lung destruction and its reversal by the tripeptide GHK," Genome Medicine 2012, 4:67.

Heiko A. Golpon, et al., "Emphysema Lung Tissue Gene Expression Profiling," Am. J. Respir. Cell Mol. Biol. vol. 31, pp. 595-600, 2004.

Adam M. Gustafson et al., "Airway P13K Pathway Activation is an Early and Reversible Event in Lung Cancer Development," Sci Transl Med 2, 26ra25 (2010).

I.H. Heijink, et al., "Characterisation of cell adhesion in airway epithelial cell types using electric cell-substrate impedance sensing," Eur Respir J 2010; 35: 894-903.

Therese S. Lapperre, et al., "Effect of Fluticasone With and Without Salmeterol on Pulmonary Outcomes in Chronic Obstructive Pulmonary Disease," Ann Intern Med. 2009;151:517-527.

Deepti Malhotra, et al., "Heightened Endoplasmic Reticulum Stress in the Lungs of Patients with Chronic Obstructive Pulmonary Disease," Am J Respir Crit Care Med vol. 180. pp. 1196-1207, 2009.

Wen Ning, et al., "Comprehensive gene expression profiles reveal pathways related to the pathogenesis of chronic obstructive pulmonary disease," PNAS, vol. 101, No. 41, 14895-900 (2004).

Stefan Pierrou, et al., "Expression of Genes Involved in Oxidative Stress Responses in Airway Epithelial Cells of Smokers with Chronic Obstructive Pulmonary Disease," Am J Respir Crit Care Med vol. 175. pp. 577-586, 2007.

Renat Shaykhiev, et al., "Cigarette smoking reprograms apical junctional complex molecular architecture in the human airway epithelium in vivo," Cell. Mol. Life Sci. (2011) 68:877-892.

Ylermi Soini, "Claudins in lung diseases," Respiratory Research 2011, 12:70.

Avrum Spira, et al., "Gene Expression Profiling of Human Lung Tissue from Smokers with Severe Emphysema," Am. J. Respir. Cell Mol. Biol. vol. 31, pp. 601-610, 2004.

Avrum Spira, et al., "Airway epithelial gene expression in the diagnostic evaluation of smokers with suspect lung aancer," Nature Medicine, vol. 13, No. 3, pp. 361-366, 2007.

Katrina Steiling, et al., "Airway Gene Expression in Chronic Obstructive Pulmonary Disease," Proc Am Thorac Soc vol. 6. pp. 697-700, 2009.

Katrina Steiling, et al., "The Field of Tissue Injury in the Lung and Airway," Cancer Prev Res 2008;1:396-403.

Katrina Steiling, et al., "Airway Gene Expression as a Molecular Phenotype of COPD," Proc Am Thorac Soc vol. 8, p. 208, 2011.

K. Steiling, et al., "Airway Epithelial Gene Expression Patterns Associated With COPD Describe Potential Molecular Phenotypes of Disease," Am J Respir Crit Care Med 183;2011:A5521.

K.A. Steiling, et al., "A Bronchial Airway Gene Expression Signature of COPD That is Reflective of Lung Tissue Disease Processes and is Reversible With Inhaled Steroids," Am J Respir Crit Care Med 185;2012:A2665.

Masako Takahashi, et al., "Localization of human airway trypsin-like protease in the airway: an immunohistochemical study," Histochem Cell Biol (2001) 115:181-187.

Martin C. Tammemagi, et al., "Incremental Value of Pulmonary Function and Sputum DNA Image Cytometry in Lung Cancer Risk Prediction," Cancer Prev Res 2011;4:552-561.

Ann E. Tilley, et al., "Down-regulation of the Notch Pathway in Human Airway Epithelium in Association with Smoking and Chronic Obstructive Pulmonary Disease," Am J Respir Crit Care Med vol. 179. pp. 457-466, 2009.

I-Ming Wang, et al., "Gene Expression Profiling in Patients with Chronic Obstructive Pulmonary Disease and Lung Cancer," Am J Respir Crit Care Med vol. 177. pp. 402-411, 2008.

* cited by examiner

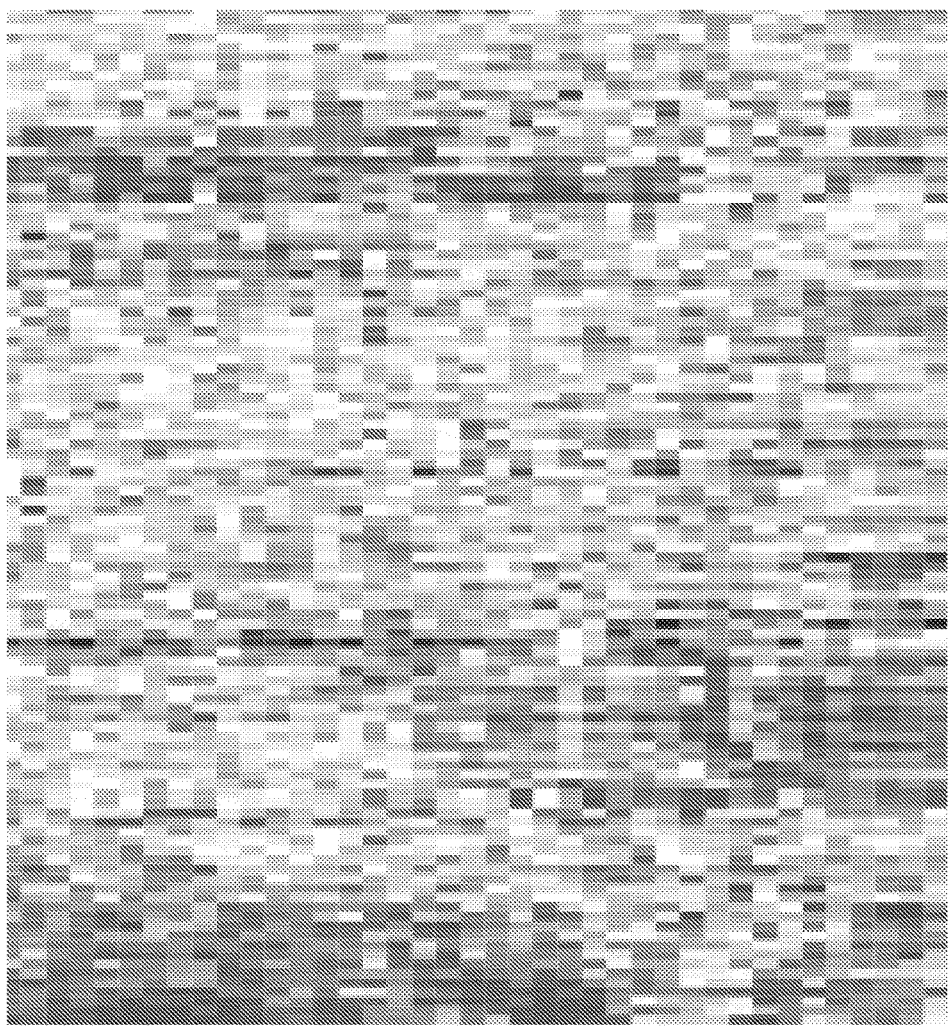
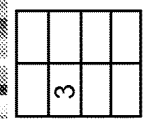
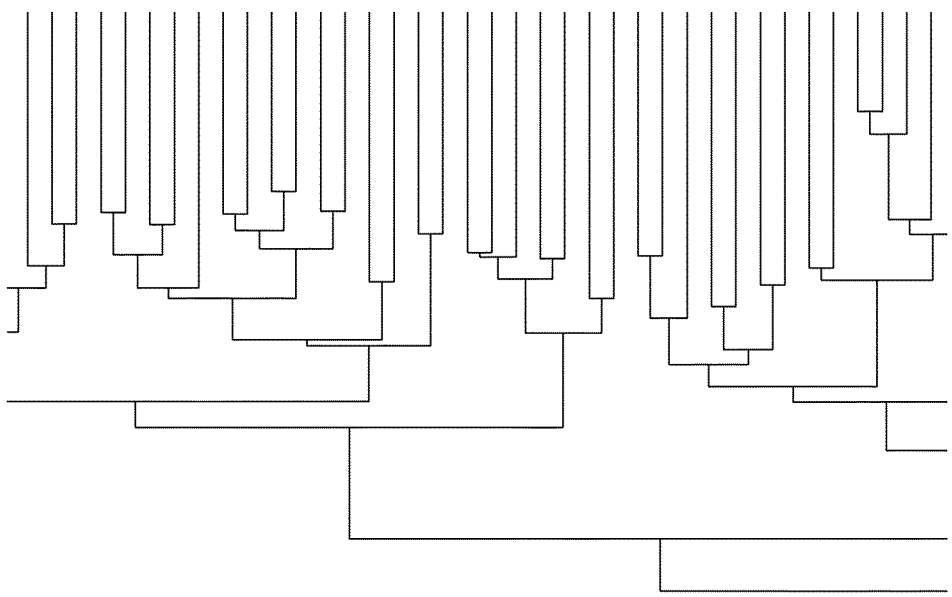
FIG. 2-3

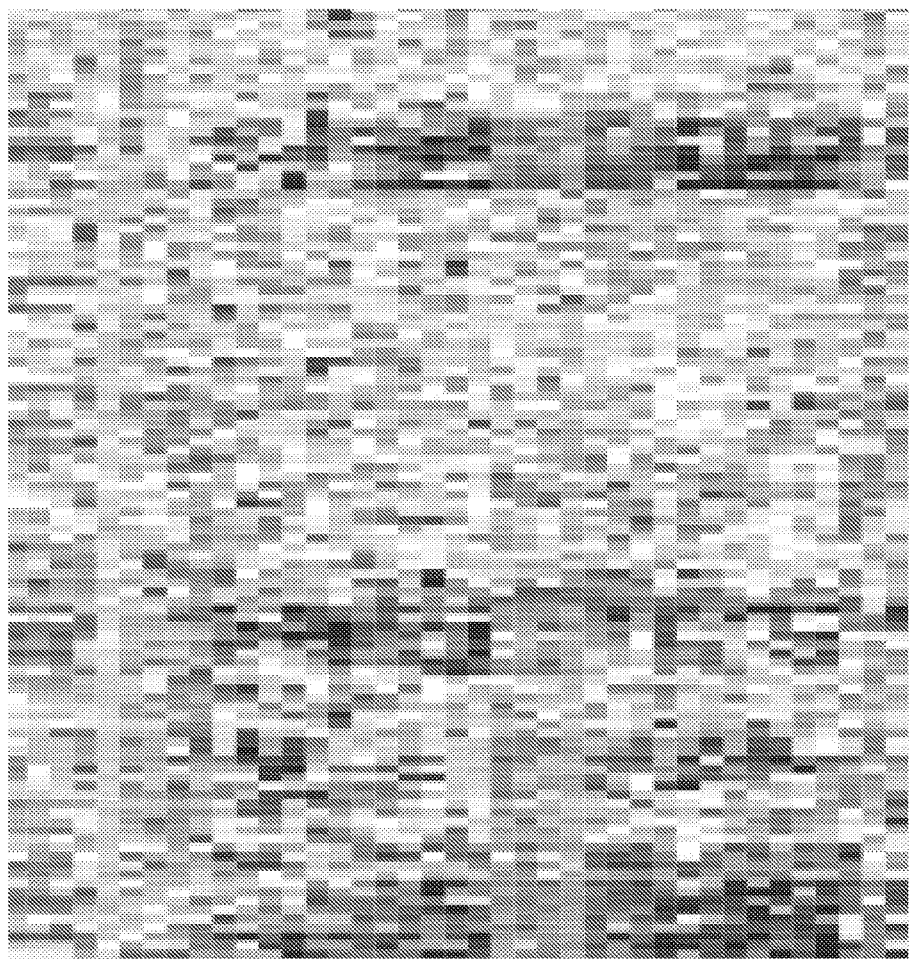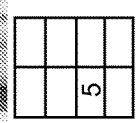
FIG. 2-5

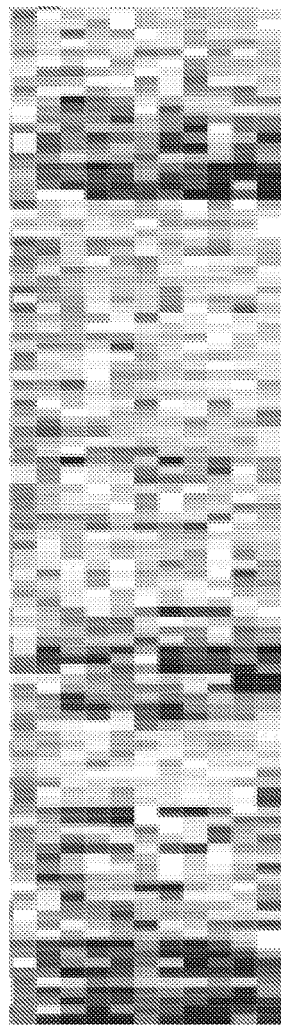
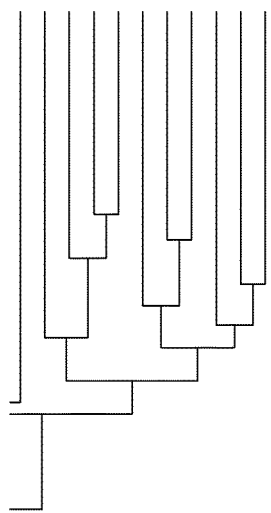
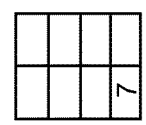
*FIG. 2-7*

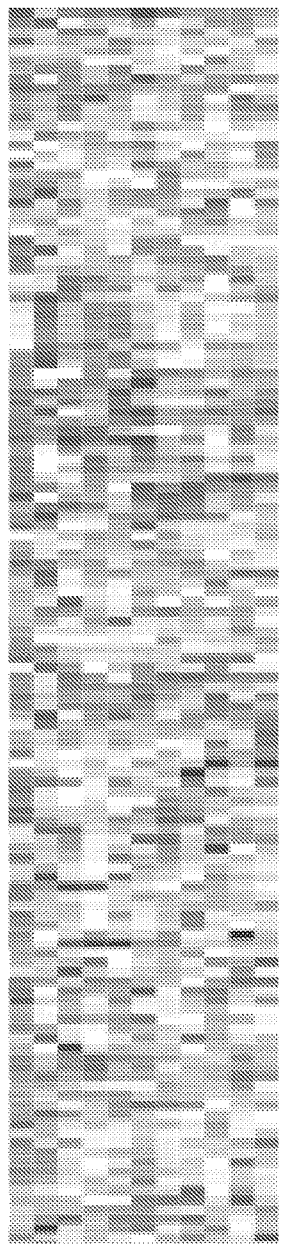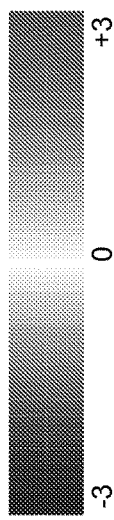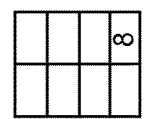
FIG. 2-8

CONTINUED-2

METHODS AND SYSTEMS FOR MONITORING, DIAGNOSING, AND TREATING CHRONIC OBSTRUCTIVE PULMONARY DISEASE

CROSS-REFERENCE TO RELATED APPLICATIONS

This application claims priority to U.S. Provisional Patent Application No. 61/649,355, filed May 20, 2012, and U.S. Provisional Patent Application No. 61/725,391, filed Nov. 12, 2012, which are hereby incorporated herein by reference.

GOVERNMENT FUNDING

This invention was made with Government Support under Contract Nos. HL095388 and RR025770 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 17, 2013, is named 1006_004_PCT.txt and is 1,147,697 bytes in size.

INTRODUCTION

Chronic obstructive pulmonary disease (COPD) affects 14.8 million individuals in the United States alone (National Heart Lung and Blood Institute. 2010. NHLBI Fiscal Year 2010 Fact Book) and is the third leading cause of death (Murphy S L, et al., 2012. Deaths: Preliminary Data for 2012. *National Vital Statistics Reports* 60). While biologic processes such as proteinase-antiproteinase imbalance, chronic inflammation, apoptosis and oxidative stress have been proposed to play a role in COPD pathogenesis, knowledge remains limited about how these molecular processes impact the clinical presentation and progression of COPD.

Genome-wide gene-expression profiling provides a powerful way to survey COPD-associated molecular alterations, but this approach has been hindered by the limited availability of lung tissue samples from individuals with impaired lung function. As a result, studies of whole-genome gene-expression profiling of lung tissue in COPD (Spira A, et al. 2004. Gene Expression Profiling of Human Lung Tissue from Smokers with Severe Emphysema. *Am J Respir Cell Mol Biol* 31:601-610; Golpon H A, et al. 2004. Emphysema Lung Tissue Gene Expression Profiling. *Am J Respir Cell Mol Biol* 31:595-600; Ning W, et al. 2004. Comprehensive gene expression profiles reveal pathways related to the pathogenesis of chronic obstructive pulmonary disease. *Proc Natl Acad Sci USA* 101:14895-14900; Bhattacharya S, et al. 2009. Molecular biomarkers for quantitative and discrete COPD phenotyes. *Am J Respir Cell Mol Biol* 40:359-367; Wang I M, et al., 2008. Gene Expression Profiling in Patients with Chronic Obstructive Pulmonary Disease and Lung Cancer. *Am J Respir Crit Care Med* 177:411.) have been limited by small sample sizes and confounding variables such as the presence of adjacent lung cancer. The development of a less invasive method for measuring COPD-associated cellular and molecular processes would allow for the study of large cohorts and the potential for identifying molecular subtypes of COPD as well as clinically-useful predictors of prognosis and response to therapy.

Alterations in airway epithelial gene expression among current and former smokers that can serve as a tool for the early detection of lung cancer. Specifically, the expression levels of genes in cytologically normal large airway epithelial cells can serve as a sensitive and specific diagnostic biomarker for lung cancer (Spira A, et al. 2007. Airway epithelial gene expression in the diagnostic evaluation of smokers with suspect lung cancer. *Nat Med* 13:361-366). Airway gene expression also reflects PI3K pathway activation in smokers with airway epithelial cell dysplasia that is reversible with the candidate lung cancer chemoprevention agent myo-inositol (Gustafson A M, et al. 2010. Airway PI3K pathway activation is an early and reversible event in lung cancer development. *Sci Transl Med* 2:26a25.). Importantly, PI3K is also activated in tumors, suggesting that the airway can potentially serve as a surrogate for assessing some disease-associated processes. The impact of lung cancer on airway gene expression suggests that the airway epithelium might also be impacted by other smoking-related diseases such as COPD. Two small studies have demonstrated COPD-associated expression differences in airway epithelium, but focused on the expression of a limited number of genes hypothesized to be involved in the pathogenesis of COPD (Pierrou S, et al. 2007. Expression of genes involved in oxidative stress responses in airway epithelial cells of smokers with chronic obstructive pulmonary disease. *Am J Respir Crit Care Med* 175:577-586; Tilley A E, et al. 2009. Down-regulation of the Notch pathway in human airway epithelium in association with smoking and chronic obstructive pulmonary disease. *Am J Respir Crit Care Med* 179:457-466.). Moreover, the relationship of these airway gene expression changes to those that occur with COPD in lung tissue remains unstudied ((Pierrou S, et al. 2007. Expression of genes involved in oxidative stress responses in airway epithelial cells of smokers with chronic obstructive pulmonary disease. *Am J Respir Crit Care Med* 175:577-586; Tilley A E, et al. 2009. Down-regulation of the Notch pathway in human airway epithelium in association with smoking and chronic obstructive pulmonary disease. *Am J Respir Crit Care Med* 179:457-466.), and it is unclear if the bronchial airway can be used as a more readily available biospecimen for identifying and measuring the activity of distal COPD-associated processes to guide clinical decisions in COPD management.

Accordingly, there is a need for new systems and methods and systems for monitoring, diagnosing, and treating COPD.

SUMMARY

Gene expression profiling of bronchial brushings obtained from current and former smokers with and without COPD was performed as described in the examples. Ninety-eight genes whose expression levels were associated with COPD status, $FEV_1\%$ predicted, and $FEV_1/FVC$ were identified. In silico analysis identified ATF4 as a potential transcriptional regulator of genes with COPD-associated airway expression, and ATF4 overexpression in airway epithelial cells in vitro recapitulated COPD-associated gene expression changes. Genes with COPD-associated expression in the bronchial airway epithelium had similarly altered expression profiles in prior studies performed on small-airway epithelium and lung parenchyma, suggesting that transcriptomic alterations in the bronchial airway epithelium reflect molecular events found at more distal sites of disease activity. Many of the airway COPD-associated gene expression changes revert toward baseline following therapy with the inhaled corticosteroid fluticasone in independent cohorts. The findings reported in the examples demonstrate a molecular field of injury throughout the bronchial airway of active and former smokers with COPD that may be driven in part by modulation of ATF4 and is modifiable with therapy. These results demonstrate the novel finding that expression of the 98 identified genes in the airway epithelium serve biomarkers for measuring biomarkers of COPD disease activity for guiding clinical management of COPD and other uses described herein.

Accordingly, this disclosure provides methods of classifying the chronic obstructive pulmonary disease (COPD) status of a subject. The methods may comprise (a) providing a tissue sample obtained from the respiratory tract epithelium of the subject; (b) determining the expression level of at least one transcript comprising (i) a sequence as set forth in any one of SEQ ID NOS. 1 to 98, (ii) a fragment of at least 100 nucleotides of a sequence as set forth in any one of SEQ ID NOS. 1 to 98, or (iii) a sequence with substantial homology to (i) or (ii), in the tissue sample to provide an expression pattern profile; (c) comparing the expression pattern profile with a reference expression pattern profile; and (d) classifying the COPD status of the subject based on the comparing.

In some embodiments of the methods the tissue sample is a tissue sample obtained from the bronchi walls of at least one of sixth generation, seventh generation, and eighth generation bronchi of the subject. In some embodiments of the methods the tissue sample is obtained during fiberoptic bronchoscopy by brushing the bronchi walls of the subject.

In some embodiments of the methods the at least one transcript is a transcript that is upregulated in COPD and is selected from SEQ ID NO: 6, SEQ ID NO: 7, SEQ ID NO: 8, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 22, SEQ ID NO: 26, SEQ ID NO: 27, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 37, SEQ ID NO: 38, SEQ ID NO: 39, SEQ ID NO: 42, SEQ ID NO: 43, SEQ ID NO: 45, SEQ ID NO: 46, SEQ ID NO: 51, SEQ ID NO: 52, SEQ ID NO: 53, SEQ ID NO: 55, SEQ ID NO: 56, SEQ ID NO: 57, SEQ ID NO: 59, SEQ ID NO: 63, SEQ ID NO: 64, SEQ ID NO: 65, SEQ ID NO: 66, SEQ ID NO: 68, SEQ ID NO: 71, SEQ ID NO: 72, SEQ ID NO: 73, SEQ ID NO: 74, SEQ ID NO: 78, SEQ ID NO: 81, SEQ ID NO: 82, SEQ ID NO: 84, SEQ ID NO: 86, SEQ ID NO: 87, SEQ ID NO: 94, SEQ ID NO: 96, and SEQ ID NO: 98.

In some embodiments of the methods the at least one transcript is a transcript that is downregulated in COPD and is selected from SEQ ID NO: 1, SEQ ID NO: 2, SEQ ID NO: 3, SEQ ID NO: 4, SEQ ID NO: 5, SEQ ID NO: 9, SEQ ID NO: 11, SEQ ID NO: 15, SEQ ID NO: 21, SEQ ID NO: 23, SEQ ID NO: 24, SEQ ID NO: 25, SEQ ID NO: 29, SEQ ID NO: 36, SEQ ID NO: 40, SEQ ID NO: 41, SEQ ID NO: 44, SEQ ID NO: 47, SEQ ID NO: 48, SEQ ID NO: 49, SEQ ID NO: 50, SEQ ID NO: 54, SEQ ID NO: 58, SEQ ID NO: 60, SEQ ID NO: 61, SEQ ID NO: 62, SEQ ID NO: 67, SEQ ID NO: 69, SEQ ID NO: 70, SEQ ID NO: 75, SEQ ID NO: 76, SEQ ID NO: 77, SEQ ID NO: 79, SEQ ID NO: 80, SEQ ID NO: 83, SEQ ID NO: 85, SEQ ID NO: 88, SEQ ID NO: 89, SEQ ID NO: 90, SEQ ID NO: 91, SEQ ID NO: 92, SEQ ID NO: 93, SEQ ID NO: 95, SEQ ID NO: 97.

In some embodiments the methods comprise determining the expression level of at least ten transcripts, each comprising (i) a sequence as set forth in any one of SEQ ID NOS. 1 to 98, (ii) a fragment of at least 100 nucleotides of a sequence as set forth in any one of SEQ ID NOS. 1 to 98, or (iii) a sequence with substantial homology to (i) or (ii), in the tissue sample to provide the expression pattern profile. In some embodiments of the methods comprise determining the expression level of at least 98 transcripts, each comprising (i) a sequence as set forth in any one of SEQ ID NOS. 1 to 98, (ii) a fragment of at least 100 nucleotides of a sequence as set forth in any one of SEQ ID NOS. 1 to 98, or (iii) a sequence with substantial homology to (i) or (ii), in the tissue sample to provide the expression pattern profile. In some embodiments the expression level of a plurality of transcripts is determined. In some embodiments the expression level of from 1-5, 5-10, 5-20, 10-25, 20-40, 30-50, 50-75, or all 98 transcripts is determined.

In some embodiments of the methods an increased relative level of expression of the at least one transcript in the respiratory tract epithelium sample of the subject, a decreased relative level of the at least one transcript in the respiratory tract epithelium sample of the subject, or a combination thereof is used to classify the COPD.

In some embodiments of the methods the COPD status of the subject is classified as to the extent of at least one of airflow obstruction, emphysematous destruction of lung parenchyma, and small airway inflammation in the subject. In some embodiments of the methods the COPD status of the subject is classified as the the likelihood of disease progression. In some embodiments of the methods the COPD status of the subject is classified as to current disease severity. In some embodiments of the methods the COPD status of the subject is classified as to the likelihood of a positive clinical response to treatment with an anti-COPD therapeutic agent. In some embodiments of the methods the COPD status of the subject is classified as to the clinical response of the subject to treatment with an anti-COPD therapeutic agent.

In some embodiments of the methods the expression level of the at least one transcript is determined by a process comprising a method selected from RT-PCR, Northern blotting, ligase chain reaction, and array hybridization.

In some embodiments the methods further comprise measuring the expression level of at least one control nucleic acid in the tissue sample.

In some embodiments of the methods the expression level of the at least one transcript is determined by a process comprising pattern recognition. In some embodiments the process comprising pattern recognition comprises a linear combination of expression levels of the target transcripts. In some embodiments of the process comprising pattern recognition comprises a nonlinear combination of expression levels of the target sequences. In some embodiments of the process comprising pattern recognition comprises a nonlinear combination of expression levels of the target sequences.

This disclosure also provides systems for expression-based classification of COPD disease status. The system comprises at least one polynucleotide capable of specifically hybridizing to a RNA transcript comprising (i) a sequence as set forth in any one of SEQ ID NOS. 1 to 98, (ii) a fragment of at least 100 nucleotides of a sequence as set forth in any one of SEQ ID NOS. 1 to 98, (iii) a sequence with substantial homology to (i) or (ii), or (iv) a sequence that is the complement of a sequence according to any one of (i) to (iii).

In some embodiments of the systems the at least one polynucleotide comprises at least one polynucleotide probe for the detection of the transcript. In some embodiments of the systems the at least one polynucleotide comprises at least one primer pair capable of amplifying a portion of the RNA transcript. In some embodiments the system comprises polynucleotides comprising sequences as set forth in SEQ ID NOs: 1, 2, 3, 4, 5, 6, 7, 8, 9 and 10. In some embodiments the system comprises at least 5 polynucleotides. In some embodiments the system system comprises at least 10 polynucleotides.

In some embodiments of the systems the at least one polynucleotide comprises a sequence corresponding to one or more nucleic acid molecules selected from: (a) a nucleic acid depicted in any one of SEQ ID NOs: 1-98; (b) an RNA form of any one of the nucleic acids depicted in SEQ ID NOs: 1-98; (c) a peptide nucleic acid form of any one of the nucleic acids depicted in SEQ ID NOs: 1-98; (d) a nucleic acid comprising at least 20 consecutive bases of any of (a-c); (e) a nucleic acid comprising at least 25 consecutive bases having at least 90% sequence identity to any of (a-c); and (f) a complement to any of (a-e).

This disclosure also provides methods of treating COPD in a subject in need thereof. The methods comprise (a) providing a tissue sample obtained from the respiratory tract epithelium of the subject; (b) determining the expression level of at least one transcript comprising (i) a sequence as set forth in any one of SEQ ID NOS. 1 to 98, (ii) a fragment of at least 100 nucleotides of a sequence as set forth in any one of SEQ ID NOS. 1 to 98, or (iii) a sequence with substantial homology to (i) or (ii), in the tissue sample to provide an expression pattern profile; (c) comparing the expression pattern profile with a reference expression pattern profile; (d) classifying the COPD status of the subject based on the comparing; (e) administering an anti-COPD therapeutic agent to the subject if the subject is classified as having active COPD disease status warranting therapeutic intervention; and/or (f) not administering an anti-COPD therapeutic agent to the subject if the subject is classified as not having active COPD disease status warranting therapeutic intervention.

In some embodiments of the methods the tissue sample is a tissue sample obtained from the bronchi walls of at least one of sixth generation, seventh generation, and eighth generation bronchi of the subject. In some embodiments of the methods the tissue sample is obtained during fiberoptic bronchoscopy by brushing the bronchi walls of the subject.

In some embodiments of the methods the at least one transcript is a transcript that is upregulated in COPD and is selected from SEQ ID NO: 6, SEQ ID NO: 7, SEQ ID NO: 8, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 22, SEQ ID NO: 26, SEQ ID NO: 27, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 37, SEQ ID NO: 38, SEQ ID NO: 39, SEQ ID NO: 42, SEQ ID NO: 43, SEQ ID NO: 45, SEQ ID NO: 46, SEQ ID NO: 51, SEQ ID NO: 52, SEQ ID NO: 53, SEQ ID NO: 55, SEQ ID NO: 56, SEQ ID NO: 57, SEQ ID NO: 59, SEQ ID NO: 63, SEQ ID NO: 64, SEQ ID NO: 65, SEQ ID NO: 66, SEQ ID NO: 68, SEQ ID NO: 71, SEQ ID NO: 72, SEQ ID NO: 73, SEQ ID NO: 74, SEQ ID NO: 78, SEQ ID NO: 81, SEQ ID NO: 82, SEQ ID NO: 84, SEQ ID NO: 86, SEQ ID NO: 87, SEQ ID NO: 94, SEQ ID NO: 96, and SEQ ID NO: 98.

In some embodiments of the methods the at least one transcript is a transcript that is downregulated in COPD and is selected from SEQ ID NO: 1, SEQ ID NO: 2, SEQ ID NO: 3, SEQ ID NO: 4, SEQ ID NO: 5, SEQ ID NO: 9, SEQ ID NO: 11, SEQ ID NO: 15, SEQ ID NO: 21, SEQ ID NO: 23, SEQ ID NO: 24, SEQ ID NO: 25, SEQ ID NO: 29, SEQ ID NO: 36, SEQ ID NO: 40, SEQ ID NO: 41, SEQ ID NO: 44, SEQ ID NO: 47, SEQ ID NO: 48, SEQ ID NO: 49, SEQ ID NO: 50, SEQ ID NO: 54, SEQ ID NO: 58, SEQ ID NO: 60, SEQ ID NO: 61, SEQ ID NO: 62, SEQ ID NO: 67, SEQ ID NO: 69, SEQ ID NO: 70, SEQ ID NO: 75, SEQ ID NO: 76, SEQ ID NO: 77, SEQ ID NO: 79, SEQ ID NO: 80, SEQ ID NO: 83, SEQ ID NO: 85, SEQ ID NO: 88, SEQ ID NO: 89, SEQ ID NO: 90, SEQ ID NO: 91, SEQ ID NO: 92, SEQ ID NO: 93, SEQ ID NO: 95, SEQ ID NO: 97.

In some embodiments the methods comprise determining the expression level of at least ten transcripts, each comprising (i) a sequence as set forth in any one of SEQ ID NOS. 1 to 98, (ii) a fragment of at least 100 nucleotides of a sequence as set forth in any one of SEQ ID NOS. 1 to 98, or (iii) a sequence with substantial homology to (i) or (ii), in the tissue sample to provide the expression pattern profile. In some embodiments the methods comprise determining the expression level of at least 98 transcripts, each comprising (i) a sequence as set forth in any one of SEQ ID NOS. 1 to 98, (ii) a fragment of at least 100 nucleotides of a sequence as set forth in any one of SEQ ID NOS. 1 to 98, or (iii) a sequence with substantial homology to (i) or (ii), in the tissue sample to provide the expression pattern profile. In some embodiments the expression level of a plurality of transcripts is determined. In some embodiments the expression level of from 1-5, 5-10, 5-20, 10-25, 20-40, 30-50, 50-75, or all 98 transcripts is determined.

In some embodiments of the methods an increased relative level of expression of the at least one transcript in the respiratory tract epithelium sample of the subject, a decreased relative level of the at least one transcript in the respiratory tract epithelium sample of the subject, or a combination thereof is used to classify the COPD.

In some embodiments of the methods the COPD status of the subject is classified as to the extent of at least one of airflow obstruction, emphysematous destruction of lung parenchyma, and small airway inflammation in the subject. In some embodiments of the methods the COPD status of the subject is classified as the the likelihood of disease progression. In some embodiments of the methods the COPD status of the subject is classified as to current disease severity. In some embodiments of the methods the COPD status of the subject is classified as to the likelihood of a positive clinical response to treatment with an anti-COPD therapeutic agent. In some embodiments of the methods the COPD status of the subject is classified as to the clinical response of the subject to treatment with an anti-COPD therapeutic agent.

In some embodiments of the methods the expression level of the at least one transcript is determined by a process comprising a method selected from RT-PCR, Northern blotting, ligase chain reaction, and array hybridization.

In some embodiments the methods further comprise measuring the expression level of at least one control nucleic acid in the tissue sample.

In some embodiments of the methods the expression level of the at least one transcript is determined by a process comprising pattern recognition. In some embodiments the process comprising pattern recognition comprises a linear combination of expression levels of the target transcripts. In some embodiments the process comprising pattern recognition comprises a nonlinear combination of expression levels of the target sequences. In some embodiments the process comprising pattern recognition comprises a nonlinear combination of expression levels of the target sequences.

In some embodiments of the methods the anti-COPD therapeutic agent is fluticasone.

BRIEF DESCRIPTION OF THE DRAWINGS

FIGS. 2-1 to 2-8 show a semi-supervised heatmap of the 98 genes associated with COPD and continuous measures of lung function. A total of 107 genes were associated with COPD, 110 genes with FEV1% predicted, and 101 genes with FEV1/FVC (FDR<0.05, FC>1.25). 98 genes were in common to all of these measures. These results demonstrate that airway epithelial gene expression reflects the presence of COPD and the severity of lung function impairment.

FIG. 3 (shows that lung tissue gene expression associated with COPD-related phenotypes is concordant with the airway epithelial gene expression signature of COPD. COPD-associated gene expression in previously published datasets was compared to the bronchial airway COPD signature. The color bar indicates the strength of association of gene expression in the previously published datasets with COPD-related phenotypes. The position of each vertical bar indicates the position of a gene from the COPD airway gene expression signature within the ranked list. The height of this bar represents the running GSEA enrichment score. This analysis identified concordant enrichment of the bronchial airway COPD signature among previously published COPD gene expression datasets (FDR<0.05).

FIG. 4 presents a validation of genes within the bronchial airway COPD signature. A total of nine genes were selected for validation by RT-PCR. For each of the nine genes, the bar plots show the mean and standard error of the log 2-gene expression level as measured by microarray (left), and the relative expression as measured by qRT-PCR.

FIG. 6 presents confirmation of in vitro ATF4 overexpression in cultured airway epithelial cells. qRT-PCR was used to confirm successful transfection and overexpression of ATF4 in BEAS2B cells. The bar plots illustrate the relative expression and standard error of ATF4 and one of its predicted downstream targets, ATF3.

FIG. 7 shows that airway epithelial gene expression associated with COPD is concordant with previously published microarray datasets of COPD lung tissue. Airway gene expression associated with COPD was compared to gene lists identified in previous studies of lung tissue gene expression in COPD using GSEA. The color bar indicates the strength of association of airway epithelial gene expression with COPD as measured by the t-statistic for the COPD term after adjusting for covariates. The position of each vertical bar from left to right indicates the position of a gene from one of the previously published lung parenchyma gene sets (genes whose expression was previously identified to be associated with a COPD-related trait) within the ranked airway gene list. The height of this bar represents the running GSEA enrichment score. This analysis identified concordant enrichment of previously reported COPD-associated gene expression changes in lung tissue and COPD-associated changes in gene expression in the bronchial airway (FDR<0.05), and suggests that there is a common COPD effect in both tissues.

DETAILED DESCRIPTION

A. Introduction

Figure 1:
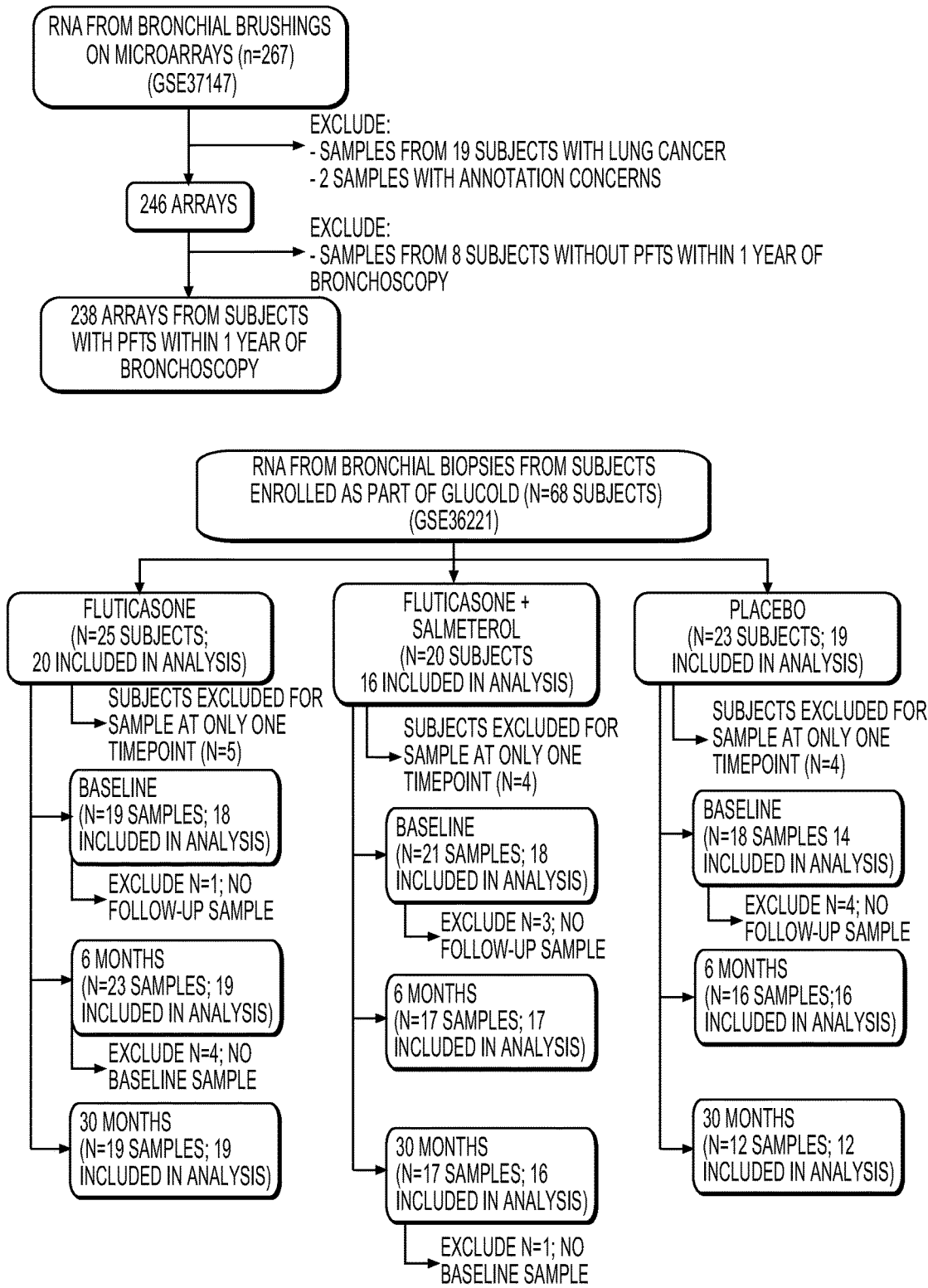
FIG. 1 is a diagram illustrating the flow of samples in the primary cohort (GSE37147) and the GLUCOLD study (GSE36221).

The present disclosure provides systems and methods for classifying COPD in a subject, which allows for the diagnosis of COPD in the subject. The systems and methods are based on the identification of expressed transcripts that are differentially expressed in the airway of subjects with COPD relative to normal subjects. These expressed transcripts can be considered as a library which can be used as a resource for the identification of sets of specific target sequences ("COPD classification sets"), which may represent the entire library of expressed transcripts or a subset of the library and the detection of which is indicative of the status of COPD in a subject. The disclosure further provides for probes capable of detecting these target sequences and primers that are capable of amplifying the target sequences.

In accordance with some embodiments, the target sequences comprised by the COPD classification set are sequences based on or derived from the gene transcripts from the library, or a subset thereof. Such sequences are occasionally referred to herein as "probe selection regions" or "PSRs." In some embodiments, the target sequences comprised by the COPD classification set are sequences based on the gene transcripts from the library, or a subset thereof, and include both coding and non-coding sequences.

The methods employ molecular analysis of the expression levels of one or more transcripts corresponding to SEQ ID NOs:1 to 98. Subsets and combinations of these transcripts may be used as described herein. In some embodiments, the systems and methods provide for the molecular analysis of the expression levels of one or more of the target sequences as set forth in SEQ ID NOs: 1-98. Subsets and combinations of these target sequences or probes complementary thereto may be used as described herein.

In some embodiments, the subset includes non-canonical expressed transcripts.

In some embodiments, the subset includes at least one transcript, each of the at least one transcripts comprising a non-coding sequence as set forth in any one of SEQ ID NOS: 1-98.

Before the present disclosure is described in further detail, it is to be understood that the inventions disclosed herein are not limited to the particular methodology, compositions, articles or machines described, as such methods, compositions, articles or machines can, of course, vary. It is also to be understood that the terminology used herein is for the purpose of describing particular embodiments only, and is not intended to limit the scope of the disclosure or the disclosed inventions.

B. Definitions and Terminology

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. Certain references and other documents cited herein are expressly incorporated herein by reference. Additionally, all UniProt/SwissProt records cited herein are hereby incorporated herein by reference. In case of conflict, the present specification, including definitions, will control. The materials, methods, and examples are illustrative only and not intended to be limiting.

The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual, 3d ed., Cold Spring Harbor Laboratory Press, Cold Spring Harbor, N.Y. (2001); Ausubel et al., Current Protocols in Molecular Biology, Greene Publishing Associates (1992, and Supplements to 2002); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999).

This disclosure refers to sequence database entries (e.g., Entrezgene ID identifiers) for certain protein and gene sequences that are published on the internet and maintained in public databases known to and used by those of skill in the art, as well as other information on the internet. The skilled artisan understands that information on the internet, including sequence database entries, is updated from time to time and that, for example, the reference number used to refer to a particular sequence can change. Where reference is made to a public database of sequence information or other information on the internet, it is understood that such changes can occur and particular embodiments of information on the internet can come and go. Because the skilled artisan can find equivalent information by searching on the internet, a reference to an internet web page address or a sequence database entry evidences the availability and public dissemination of the information in question.

Before the present proteins, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The terms "comprising" and "having" as used herein are synonymous with each other and "including" or "containing", and are inclusive or open-ended and do not exclude additional, unrecited members, elements or method steps The term "polynucleotide" as used herein refers to a polymer of greater than one nucleotide in length of ribonucleic acid (RNA), deoxyribonucleic acid (DNA), hybrid RNA/DNA, modified RNA or DNA, or RNA or DNA mimetics, including peptide nucleic acids (PNAs). The polynucleotides may be single- or double-stranded. The term includes polynucleotides composed of naturally-occurring nucleobases, sugars and covalent internucleoside (backbone) linkages as well as polynucleotides having non-naturally-occurring portions which function similarly. Such modified or substituted polynucleotides are well-known in the art and for the purposes of this disclosure, are referred to as "analogues."

"Complementary" or "substantially complementary" refers to the ability to hybridize or base pair between nucleotides or nucleic acids, such as, for instance, between a sensor peptide nucleic acid or polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, in some embodiments at least about 90% to 95%, and in some embodiments at least about 95%, 96%, 97%, 98%, 99%, up to 100%.

Alternatively, substantial complementarity exists when a polynucleotide will hybridize under selective hybridization conditions to its complement. Typically, selective hybridization will occur when there is at least about 65% complementarity over a stretch of at least 14 to 25 bases, for example at least about 75%, or at least about 90% complementarity. See, M. Kanehisa Nucleic Acids Res. 12:203 (1984).

"Preferential binding" or "preferential hybridization" refers to the increased propensity of one polynucleotide to bind to its complement in a sample as compared to a noncomplementary polymer in the sample.

Hybridization conditions will typically include salt concentrations of less than about 1M, more usually less than about 500 mM, for example less than about 200 mM. In the case of hybridization between a peptide nucleic acid and a polynucleotide, the hybridization can be done in solutions containing little or no salt. Hybridization temperatures can be as low as 5° C., but are typically greater than 22° C., such as greater than about 30° C., for example in excess of about 37° C. Longer fragments may require higher hybridization temperatures for specific hybridization as is known in the art. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

A "target sequence as used herein (also occasionally referred to as a "PSR" or "probe selection region") refers to a region of the genome against which one or more probes can be designed. As used herein, a probe is any polynucleotide capable of selectively hybridizing to a target sequence or its complement, or to an RNA version of either. A probe may comprise ribonucleotides, deoxyribonucleotides, peptide nucleic acids, and combinations thereof. A probe may optionally comprise one or more labels. In some embodiments, a probe may be used to amplify one or both strands of a target sequence or an RNA form thereof, acting as a sole primer in an amplification reaction or as a member of a set of primers.

"Administer" refers to the placement of a composition into a subject by a method or route which results in at least partial localization of the composition at a desired site such that desired effect is produced. A compound or composition described can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. In some embodiments, the compositions are administered by intravenous infusion or injection.

As used herein the terms "treat," "treatment," and the like, refer to a decrease in severity, indicators, symptoms, or markers of COPD. In the context of the present disclosure insofar as it relates to any of the conditions recited herein, the terms "treat," "treatment," and the like mean to relieve, alleviate, ameliorate, inhibit, slow down, reverse, or stop the progression, aggravation, deterioration, progression, anticipated progression or severity of at least one symptom or complication associated with COPD. In some embodiments, the symptoms of COPD are alleviated by at least 5%, at least 10%, at least 20%, at least 30%, at least 40%, or at least 50%.

As used herein, a "subject" means a human or animal. Typically, the subject is a mammal. The mammal can be a human, non-human primate, mouse, rat, dog, cat, horse, or cow, but are not limited to these examples. Mammals other than humans can be advantageously used, for example, as subjects that represent animal models of COPD, for example. In addition, the methods, systems and other aspects described herein can be used to classify and/or treat domesticated animals and/or pets. A subject can be male or female. A subject can be one who has been previously diagnosed with or identified as suffering from or having COPD or one or more complications related to COPD, and optionally, but need not have already undergone treatment for COPD or the one or more complications related to COPD. A subject can also be one who is not suffering from COPD. A subject can also be one who has been diagnosed as having an above average likelihood of developing COPD or one or more complications related to COPD. It can include one who shows improvements in known COPD risk factors as a result of receiving one or more treatments for COPD or one or more complications related to COPD. Alternatively, a subject can also be one who has not been previously diagnosed as having COPD or one or more complications related to COPD. For example, a subject can be one who exhibits one or more risk factors for COPD or one or more complications related to COPD, or a subject who does not exhibit COPD risk factors, or a subject who is asymptomatic for COPD or one or more complications related to COPD. A subject can also be one who is suffering from or at risk of developing COPD or one or more complications related to COPD. A subject can also be one who has been diagnosed with or identified as having one or more complications related to COPD, or alternatively, a subject can be one who has not been previously diagnosed with or identified as having one or more complications related to COPD.

The term "chronic obstructive pulmonary disease" or "COPD" is generally applied to chronic respiratory disease processes characterized by the persistent obstruction of bronchial air flow. COPD patients can suffer from conditions such as bronchitis, cystic fibrosis, asthma or emphysema.

As used herein, the term "respiratory tract epithelium" refers to epithelium from anywhere in the upper respiratory tract or respiratory airways. The term specifically excludes lung tissue. Thus, the term includes epithelium from the nose, mouth, nasal passages, paranasal sinuses, pharynx, larynx, trachea, bronchi and bronchioles. In some embodiments the term may include epithelium from one, two, three, four, five, six, seven, eight, or all of the nose, mouth, nasal passages, paranasal sinuses, pharynx, larynx, trachea, bronchi and bronchioles. In some embodiments respiratory tract epithelium is specified as epithelium from the mouth. In some embodiments respiratory tract epithelium is specified as epithelium from the nose. In some embodiments respiratory tract epithelium is specified as epithelium from the trachea. In some embodiments respiratory tract epithelium is specified as epithelium from the bronchi. In some embodiments respiratory tract epithelium is specified as epithelium from at least one of the sixth generation, seventh generation, and eighth generation bronchi. Because the term "respiratory tract epithelium" specifically excludes lung tissue it excludes tissue from any of the respiratory bronchioles, alveolar ducts, alveolar sacs, and alveoli.

As used herein, an "anti-COPD therapeutic" refers to any molecule used treat COPD. Non-limiting examples include bronchodilators (e.g. short and long acting β-2 stimulants), orally administered bronchodilators, anti-cholinergic agents (e.g. ipratoprium bromide, theophylline compounds or a combination), inhaled anti-cholinergic agents, steroids (oral or topical), corticosteroids, fluticasone, mucolytic agents (e.g., ambroxol, ergosterin, carbocysteine, iodinated glycerol), antibiotics, antifungals, moisterization by nebulization, anti-tussives, respiratory stimulants (e.g., doxapram, almitrine bismesylate), a-1 antitrypsin administration, fromoterol, budesonide, and/or fromoterol/budesonide combination therapy. In some embodiments the anti-COPD therapeutic agent is a GHK tripeptide in any form. GHK is comprised of a Glycine-Histidine-Lysine tripeptide. GHK may be synthesized by methods familiar to those skilled in the art or purchased commercially. GHK tripeptides are described in WO2012/129237A2, which is hereby incorporated herein by reference.

"Optional" or "optionally" means that the subsequently described event or circumstance may or may not occur, and that the description includes instances where the event or circumstance occurs and instances in which it does not.

As used herein, the term "about" refers to approximately a+/−10% variation from a given value. It is to be understood that such a variation is always included in any given value provided herein, whether or not it is specifically referred to.

Terms such as "connected," "attached," "linked" and "conjugated" are used interchangeably herein and encompass direct as well as indirect connection, attachment, linkage or conjugation unless the context clearly dictates otherwise.

As used herein, "classifying the COPD status" of a subject includes without limitation, determining that the subject has an increased likelihood of currently suffering from COPD or that the subject currently does suffer from COPD, determining that the subject does not have an increased likelihood of currently suffering from COPD or that the subject currently does not suffer from COPD, determining that the subject has an increased risk of developing COPD in the future, and determining that the subject does not have an increased risk of developing COPD in the future. The term also includes determining that a subject is more or less likely to respond to a particular course of therapeutic intervention such as without limitation a course of treatment with a an anti-COPD therapeutic agent. As a skilled artisan will appreciate, the term includes all forms of diagnosing COPD and/or the symptoms of COPD and of prognosis of subjects who suffer from COPD.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed by the disclosure. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the disclosure, as are ranges based thereon. Where a combination is disclosed, each subcombination of the elements of that combination is also specifically disclosed and is within the scope of the disclosure. Conversely, where different elements or groups of elements are disclosed, combinations thereof are also disclosed. Where any element of is disclosed as having a plurality of alternatives, examples of that element in which each alternative is excluded singly or in any combination with the other alternatives are also hereby disclosed; more than one element of an embodiment can have such exclusions, and all combinations of elements having such exclusions are hereby disclosed.

C. COPD Classification System

The systems of the present disclosure are based on the identification of a library of gene transcripts (COPD classification library) that are differentially expressed in the respiratory tract epithelium of subjects having a COPD disease state in their lung tissue relative to the respiratory tract epithelium of subjects having healthy lung tissue, and thus may be diagnostic for COPD disease state. For example, relative over and/or under expression of one or more of the gene transcripts in an airway tissue sample compared to a reference sample or expression profile or signature there from may be indicative of a COPD disease state. The reference sample can be, for example, from the respiratory tract epithelium of a subject having healthy lung tissue. The reference expression profile or signature may optionally be normalized to one or more appropriate reference gene transcripts. Alternatively or in addition to, expression of one or more of the gene transcripts in a respiratory tract epithelium sample may be compared to an expression profile or signature from one or more known COPD respiratory tract epithelium samples such that a substantially similar expression profile or signature may be used to validate a finding of COPD disease state or may be compared to the expression profile or signature from respiratory tract epithelium of subjects with normal lung tissue.

Expression profiles or signatures from diagnostic samples may be normalized to one or more house keeping gene transcripts such that normalized over and/or under expression of one or more of the gene transcripts in a respiratory tract epithelium sample may be indicative of a COPD disease state.

D. COPD Classification Library

The COPD Classification Library in accordance with the present disclosure comprises at least one gene transcript whose relative and/or normalized expression is indicative of a COPD disease state or the absence of a COPD disease state. Gene transcripts which show differential expression in respiratory tract epithelium of subjects with COPD diseased lung tissue include (i) transcripts comprising the sequences as set forth in SEQ ID NOS: 1 to 98, (ii) transcripts comprising a fragment of at least 100 nucleotides of a sequence as set forth in any one of SEQ ID NOS: 1 to 98, or (iii) a sequence with substantial homology to (i) or (ii). In some embodiments of the disclosure, the library comprises at least one of the gene transcripts, each of the transcripts comprising a sequence as set forth in any one of SEQ ID NOS: 1 to 98.

In some embodiments, the library comprises at least one transcript that (i) comprises a sequence as set forth in SEQ ID NOS: 1 to 98, (ii) comprises a fragment of at least 100 nucleotides of a sequence as set forth in any one of SEQ ID NOS: 1 to 98, or (iii) comprises a sequence with substantial homology to (i) or (ii). In some embodiments, the library comprises at least five transcripts, each of which (i) comprises a sequence as set forth in SEQ ID NOS: 1 to 98, (ii) comprises a fragment of at least 100 nucleotides of a sequence as set forth in any one of SEQ ID NOS: 1 to 98, or (iii) comprises a sequence with substantial homology to (i) or (ii). In some embodiments, the library comprises at least 10 transcripts, each of which (i) comprises a sequence as set forth in SEQ ID NOS: 1 to 98, (ii) comprises a fragment of at least 100 nucleotides of a sequence as set forth in any one of SEQ ID NOS: 1 to 98, or (iii) comprises a sequence with substantial homology to (i) or (ii). In some embodiments, the library comprises at least 15 transcripts, each of which (i) comprises a sequence as set forth in SEQ ID NOS: 1 to 98, (ii) comprises a fragment of at least 100 nucleotides of a sequence as set forth in any one of SEQ ID NOS: 1 to 98, or (iii) comprises a sequence with substantial homology to (i) or (ii). In some embodiments, the library comprises at least 20, at least 25, at least 30, at least 35, at least 40, at least 45, at least 50, at least 55, at least 60, at least 65, at least 70, at least 75, at least 80, at least 85, at least 90, at lease 95 or at least 98 transcripts, each of the at least 20, at least 25, at least 30, at least 35, at least 40, at least 45, at least 50, at least 55, at least 60, at least 65, at least 70, at least 75, at least 80, at least 85, at least 90, at lease 95 or at least 98 transcripts each of which (i) comprises a sequence as set forth in SEQ ID NOS: 1 to 98, (ii) comprises a fragment of at least 100 nucleotides of a sequence as set forth in any one of SEQ ID NOS: 1 to 98, or (iii) comprises a sequence with substantial homology to (i) or (ii).

In some embodiments the library comprises transcripts that correspond to the gene sequences listed in a table selected from Tables B, C, D, E, F, and G.

This disclosure also contemplates that alternative libraries may be designed that include in addition to transcripts comprising a sequence as set forth in any one of SEQ ID NOs: 1 to 98, additional gene transcripts that are identified as having differential expression in the respiratory tract epithelium of subjects having COPD diseased lung tissue as compared to the respiratory tract epithelium of subjects having healthy lung tissue. As is known in the art, the publication and sequence databases can be mined using a variety of search strategies to identify appropriate candidates for inclusion in the library. For example, currently available scientific and medical publication databases such as Medline, Current Contents, OMIM (online Mendelian inheritance in man), various Biological and Chemical Abstracts, Journal indexes, and the like can be searched using term or key-word searches, or by author, title, or other relevant search parameters. Many such databases are publicly available, and strategies and procedures for identifying publications and their contents, for example, genes, other nucleotide sequences, descriptions, indications, expression pattern, etc, are well known to those skilled in the art. Numerous databases are available through the internet for free or by subscription, see, for example, the National Center Biotechnology Information (NCBI), Infotrieve, Thomson ISI, and Science Magazine (published by the AAAS) websites. Additional or alternative publication or citation databases are also available that provide identical or similar types of information, any of which can be employed in the context of the disclosure. These databases can be searched for publications describing altered gene expression between the respiratory tract epithelium of subjects having COPD diseased lung tissue as compared to the respiratory tract epithelium of subjects having healthy lung tissue. Additional potential candidate genes may be identified by searching the above described databases for differentially expressed proteins and by identifying the nucleotide sequence encoding the differentially expressed proteins.

In alternative embodiments the COPD Classification Library in accordance with the present disclosure comprises at least one protein encoded by a transcript whose relative and/or normalized expression is indicative of a COPD disease state or the absence of a COPD disease state. Gene transcripts which show differential expression in respiratory tract epithelium of subjects with COPD diseased lung tissue include (i) transcripts comprising the sequences as set forth in SEQ ID NOS: 1 to 98, (ii) transcripts comprising a fragment of at least 100 nucleotides of a sequence as set forth in any one of SEQ ID NOS: 1 to 98, or (iii) a sequence with substantial homology to (i) or (ii). Thus, in some embodiments of the disclosure, the library comprises at least one protein encoded by at least one of SEQ ID NOS: 1 to 98. In some embodiments the at least one protein comprises a sequence selected from SEQ ID NOS: 99-195.

E. COPD Classification Sets

A COPD Classification Set comprises one or more target sequences identified within each of the gene transcripts in the COPD classification library, or a subset of these gene transcripts. The target sequences may be within the coding and/or non-coding regions of the gene transcripts. The set can comprise one or a plurality of target sequences from each gene transcript in the library, or subset thereof. The relative and/or normalized level of these target sequences in a sample is indicative of the level of expression of the particular gene transcript and thus of having COPD diseased lung tissue or having healthy lung tissue. For example, the relative and/or normalized expression level of one or more of the target sequences may be indicative of a COPD disease state while the relative and/or normalized expression level of one or more other target sequences may be indicative of healthy lung tissue.

Accordingly, in some embodiments the present disclosure provides for a library or catalog of candidate target sequences derived from the transcripts (both coding and non-coding regions) of at least one gene suitable for classifying a COPD disease state as being present or absent. In further embodiments, the library or catalog of candidate target sequences comprises target sequences as set forth in SEQ ID NOS: 1 to 98. The library or catalog in effect provides a resource list of transcripts from which target sequences appropriate for inclusion in a COPD classification set can be derived. In one embodiment, an individual COPD classification set may comprise target sequences derived from the transcripts of one or more genes exhibiting a positive correlation with a COPD disease state. In some embodiments, an individual COPD classification set may comprise target sequences derived from the transcripts of one or more genes exhibiting a negative correlation with a COPD disease state. In some embodiments, an individual COPD Classification Set may comprise target sequences derived from the transcripts of from two or more genes, wherein at least one gene has a transcript that exhibits a positive correlation with COPD and at least one gene has a transcript that exhibits a negative correlation with COPD.

In some embodiments, the COPD Classification Set comprises target sequences derived from the transcripts of at least one gene. In some embodiments, the COPD Classification set comprises target sequences derived from the transcripts of at least 5 genes. In some embodiments, the COPD Classification set comprises target sequences derived from the transcripts of at least 10 genes. In some embodiments, the COPD Classification set comprises target sequences derived from the transcripts of at least 15 genes. In some embodiments, the COPD Classification set comprises target sequences derived from the transcripts of at least 20, at least 25, at least 30, at least 35, at least 40, at least 45, at least 50, at least 55, at least 60, at least 65, at least 70, at least 75, at least 80, at least 85, at least 90, at least 95, or at least 98 genes.

Following the identification of candidate gene transcripts, appropriate target sequences can be identified by screening for target sequences that have been annotated to be associated with each specific gene locus from a number of annotation sources including GenBank, RefSeq, Ensembl, dbEST, GENSCAN, TWINSCAN, Exoniphy, Vega, microRNAs registry and others (see Affymetrix Exon Array design note).

As part of the target sequence selection process, target sequences can be further evaluated for potential cross-hybridization against other putative transcribed sequences in the design (but not the entire genome) to identify only those target sequences that are predicted to uniquely hybridize to a single target.

The set of target sequences that are predicted to uniquely hybridize to a single target can be further filtered using a variety of criteria including, for example, sequence length, for their mean expression levels across a wide selection of human tissues, as being representative of transcripts expressed either as novel alternative (i.e., non-consensus) exons, alternative retained introns, novel exons 5' or 3' of the gene's transcriptional start site or representing transcripts expressed in a manner antisense to the gene, and others.

In some embodiments, the COPD Classification Set comprises target sequences derived from the sequences as set forth in at least one sequence selected from SEQ ID NOs: 1-98.

In some embodiments, the COPD Classification Set comprises at least one target sequences derived from each of the sequences set forth in SEQ ID NOs: 1-98.

In some embodiments, the potential set of target sequences can be filtered for their expression levels using the multi-tissue expression data made publicly available by Affymetrix such that probes with, for example, expression across numerous tissues or no expression in respiratory tract epithelium can be excluded.

In some embodiments, the COPD classification set can be specifically designed to be indicative of COPD disease in general or alternatively be indicative of one or more individual clinical manifestations of COPD.

E. Validation of Target Sequences

Following selection in silico or otherwise of target sequences, each target sequence suitable for use in the COPD classification set may be validated to confirm differential relative or normalized expression in respiratory tract epithelium of subjects having COPD and/or not having COPD. Validation methods are known in the art and include hybridization techniques such as microarray analysis or Northern blotting using appropriate controls, and may include one or more additional steps, such as reverse transcription, transcription, PCR, RT-PCR and the like. The validation of the target sequences using these methods is well within the abilities of a worker skilled in the art.

F. Minimal Expression Signature

In some embodiments, individual COPD classification sets provide for at least a determination of a minimal expression signature, capable of distinguishing between the presence of COPD in lung tissue. Means for determining the appropriate number of target sequences necessary to obtain a minimal expression signature are known in the art and include, without limitation, the Nearest Shrunken Centroids (NSC) method.

In the NSC method (see US 20070031873), a standardized centroid is computed for each class. This is the average gene expression for each gene in each class divided by the within-class standard deviation for that gene. Nearest centroid classification takes the gene expression profile of a new sample, and compares it to each of these class centroids. The class whose centroid that it is closest to, in squared distance, is the predicted class for that new sample. Nearest shrunken centroid classification "shrinks" each of the class centroids toward the overall centroid for all classes by an amount called the threshold. This shrinkage consists of moving the centroid towards zero by threshold, setting it equal to zero if it hits zero. For example if threshold was 2.0, a centroid of 3.2 would be shrunk to 1.2, a centroid of −3.4 would be shrunk to −1.4, and a centroid of 1.2 would be shrunk to zero. After shrinking the centroids, the new sample is classified by the usual nearest centroid rule, but using the shrunken class centroids. This shrinkage can make the classifier more accurate by reducing the effect of noisy genes and provides an automatic gene selection. In particular, if a gene is shrunk to zero for all classes, then it is eliminated from the prediction rule. Alternatively, it may be set to zero for all classes except one, and it can be learned that the high or low expression for that gene characterizes that class. The user decides on the value to use for threshold. Typically one examines a number of different choices. To guide in this choice, PAM does K-fold cross-validation for a range of threshold values. The samples are divided up at random into K roughly equally sized parts. For each part in turn, the classifier is built on the other K-1 parts then tested on the remaining part. This is done for a range of threshold values, and the cross-validated misclassification error rate is reported for each threshold value. Typically, the user would choose the threshold value giving the minimum cross-validated misclassification error rate.

Alternatively, minimal expression signatures can be established through the use of optimization algorithms such as the mean variance algorithm widely used in establishing stock portfolios. This method is described in detail in US patent publication number 20030194734. Essentially, the method calls for the establishment of a set of inputs (stocks in financial applications, expression as measured by intensity here) that will optimize the return (e.g., signal that is generated) one receives for using it while minimizing the variability of the return. In other words, the method calls for the establishment of a set of inputs (e.g., expression as measured by intensity) that will optimize the signal while minimizing variability. Many commercial software programs are available to conduct such operations. "Wagner Associates Mean-Variance Optimization Application," referred to as "Wagner Software" throughout this specification, is one suitable option. This software uses functions from the "Wagner Associates Mean-Variance Optimization Library" to determine an efficient frontier and optimal portfolios in the Markowitz sense. Use of this type of software requires that microarray data be transformed so that it can be treated as an input in the way stock return and risk measurements are used when the software is used for its intended financial analysis purposes.

The process of selecting a minimal expression signature can also include the application of heuristic rules. Preferably, such rules are formulated based on biology and an understanding of the technology used to produce clinical results. More preferably, they are applied to output from the optimization method. For example, the mean variance method of portfolio selection can be applied to microarray data for a number of genes differentially expressed in the respiratory tract epithelium of subjects with COPD.

Other heuristic rules can be applied that are not necessarily related to the biology in question. For example, one can apply a rule that only a prescribed percentage of the portfolio can be represented by a particular gene or group of genes. Commercially available software such as the Wagner Software readily accommodates these types of heuristics. This can be useful, for example, when factors other than accuracy and precision have an impact on the desirability of including one or more genes.

In some embodiments, the COPD classification set for obtaining a minimal expression signature comprises at least one, two, three, four, five, six, eight, 10, 15, 20, 25 or more of target sequences shown to have a positive correlation with COPD disease state, for example those depicted in SEQ ID NOs: 1-98 or a subset thereof.

In some embodiments, the COPD classification set comprises target sequences for detecting expression products of SEQ ID NOs:1-98. In some embodiments the COPD classification set comprises target sequences for detecting expression products of each gene listed in Table B. In some embodiments the COPD classification set comprises target sequences for detecting expression products of each gene listed in Table C. In some embodiments the COPD classification set comprises target sequences for detecting expression products of each gene listed in Table D. In some embodiments the COPD classification set comprises target sequences for detecting expression products of each gene listed in Table E. In some embodiments the COPD classification set comprises target sequences for detecting expression products of each gene listed in Table F. In some embodiments the COPD classification set comprises target sequences for detecting expression products of each gene listed in Table G.

The COPD classification set can optionally include one or more target sequences specifically derived from the transcripts of one or more housekeeping genes and/or one or more internal control target sequences and/or one or more negative control target sequences. In one embodiment, these target sequences can, for example, be used to normalize expression data. Housekeeping genes from which target sequences for inclusion in a COPD Classification Set can be derived from are known in the art and include those genes in which are expressed at a constant level in normal respiratory tract epithelium.

The target sequences described herein may be used alone or in combination with each other or with other known or later identified disease markers.

G. COPD Classification Probes/Primers

The systems of this disclosure provide combinations of polynucleotide probes that are capable of detecting the target sequences of the COPD Classification Sets. Individual polynucleotide probes comprise a nucleotide sequence derived from the nucleotide sequence of the target sequences or complementary sequences thereof. The nucleotide sequence of the polynucleotide probe is such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In some embodiments of the disclosure, the polynucleotide probe is complementary to a region of a target mRNA derived from a PSR in the COPD classification set. Computer programs can also be employed to select probe sequences that will not cross hybridize or will not hybridize non-specifically.

One skilled in the art will understand that the nucleotide sequence of the polynucleotide probe need not be identical to its target sequence in order to specifically hybridise thereto. The polynucleotide probes of the present disclosure, therefore, comprise a nucleotide sequence that is at least about 75% identical to a region of the target gene or mRNA. In some embodiments, the nucleotide sequence of the polynucleotide probe is at least about 90% identical a region of the target gene or mRNA. In some embodiments, the nucleotide sequence of the polynucleotide probe is at least about 95% identical to a region of the target gene or mRNA. Methods of determining sequence identity are known in the art and can be determined, for example, by using the BLASTN program of the University of Wisconsin Computer Group (GCG) software or provided on the NCBI website. The nucleotide sequence of the polynucleotide probes of the present invention may exhibit variability by differing (e.g. by nucleotide substitution, including transition or transversion) at one, two, three, four or more nucleotides from the sequence of the target gene.

Other criteria known in the art may be employed in the design of the polynucleotide probes of the present disclosure. For example, the probes can be designed to have <50% G content and/or between about 25% and about 70% G+C content. Strategies to optimize probe hybridization to the target nucleic acid sequence can also be included in the process of probe selection. Hybridization under particular pH, salt, and temperature conditions can be optimized by taking into account melting temperatures and by using empirical rules that correlate with desired hybridization behaviours. Computer models may be used for predicting the intensity and concentration-dependence of probe hybridization.

As is known in the art, in order to represent a unique sequence in the human genome, a probe should be at least about 15 nucleotides in length. Accordingly, the polynucleotide probes of the present invention range in length from about 15 nucleotides to the full length of the PSR or target mRNA. In some embodiments, the polynucleotide probes are at least about 15 nucleotides in length. In some embodiments, the polynucleotide probes are at least about 20 nucleotides in length. In some embodiments, the polynucleotide probes are at least about 25 nucleotides in length. In some embodiments, the polynucleotide probes are between about 15 nucleotides and about 500 nucleotides in length. In some embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides, about 15 nucleotides and about 250 nucleotides, about 15 nucleotides and about 200 nucleotides, about 15 nucleotides and about 150 nucleotides, about 15 nucleotides and about 100 nucleotides, about 15 nucleotides and about 50 nucleotides in length.

The polynucleotide probes of a COPD classification set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability.

The system of the present invention further provides for primers and primer pairs capable of amplifying target sequences defined by the COPD classification set, or fragments or subsequences or complements thereof. The nucleotide sequences of the COPD classifying set may be provided in computer-readable media for in silico applications and as a basis for the design of appropriate primers for amplification of one or more target sequences of the COPD classifying set.

Primers based on the nucleotide sequences of target sequences can be designed for use in amplification of the target sequences. For use in amplification reactions such as PCR, a pair of primers will be used. The exact composition of the primer sequences is not critical, but for most applications the primers will hybridize to specific sequences of the COPD classification set under stringent conditions, particularly under conditions of high stringency, as known in the art. The pairs of primers are usually chosen so as to generate an amplification product of at least 50 to about 100 nucleotides. Algorithms for the selection of primer sequences are generally known, and are available in commercial software packages. These primers may be used in standard quantitative or qualitative PCR-based assays to assess transcript expression levels of RNAs defined by the COPD classification set. Alternatively, these primers may be used in combination with probes, such as molecular beacons in amplifications using real-time PCR.

In some embodiments, the primers or primer pairs, when used in an amplification reaction, specifically amplify at least a portion of a nucleic acid depicted in one of SEQ ID NOs: 1-98, an RNA form thereof, or a complement to either thereof. Optionally, when amplified, either stand produced by amplification may be provided in purified and/or isolated form.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. Specific examples of polynucleotide probes or primers useful in this invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary polynucleotide probes or primers having modified oligonucleotide backbones include, for example, those with one or more modified internucleoside linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3' amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene containing backbones; sulphamate backbones; methyleneimino and methylenehydrazino backbones; sulphonate and sulfonamide backbones; amide backbones; and others having mixed N, O, S and $CH_2$ component parts.

The present disclosure also contemplates oligonucleotide mimetics in which both the sugar and the internucleoside linkage of the nucleotide units are replaced with novel groups. The base units are maintained for hybridization with an appropriate nucleic acid target compound. An example of such an oligonucleotide mimetic, which has been shown to have excellent hybridization properties, is a peptide nucleic acid (PNA) [Nielsen et al., Science, 254:1497-1500 (1991)]. In PNA compounds, the sugar-backbone of an oligonucleotide is replaced with an amide containing backbone, in particular an aminoethylglycine backbone. The nucleobases are retained and are bound directly or indirectly to aza-nitrogen atoms of the amide portion of the backbone.

The present disclosure also contemplates polynucleotide probes or primers comprising "locked nucleic acids" (LNAs), which are novel conformationally restricted oligonucleotide analogues containing a methylene bridge that connects the 2'-O of ribose with the 4'-C (see, Singh et al., Chem. Commun., 1998, 4:455-456). LNA and LNA analogues display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described (see Koshkin et al., Tetrahedron, 1998, 54:3607-3630). Studies of mis-matched sequences show that LNA obey the Watson-Crick base pairing rules with generally improved selectivity compared to the corresponding unmodified reference strands.

LNAs form duplexes with complementary DNA or RNA or with complementary LNA, with high thermal affinities. The universality of LNA-mediated hybridization has been emphasized by the formation of exceedingly stable LNA:LNA duplexes (Koshkin et al., J. Am. Chem. Soc., 1998, 120:13252-13253). LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements.

Synthesis of 2'-amino-LNA (Singh et al., J. Org. Chem., 1998, 63, 10035-10039) and 2'-methylamino-LNA has been described and thermal stability of their duplexes with complementary RNA and DNA strands reported. Preparation of phosphorothioate-LNA and 2'-thio-LNA have also been described (Kumar et al., Bioorg. Med. Chem. Lett., 1998, 8:2219-2222).

Modified polynucleotide probes or primers may also contain one or more substituted sugar moieties. For example, oligonucleotides may comprise sugars with one of the following substituents at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Examples of such groups are: $O[(CH_2)_nO]_mCH_3$, $O(CH_2)_nOCH_3$, $O(CH_2)_nNH_2$, $(CH_2)_nCH_3$, $O(CH_2)_nONH_2$, and $O(CH_2)_nON[(CH_2)_nCH_3)]_2$, where n and m are from 1 to about 10. Alternatively, the oligonucleotides may comprise one of the following substituents at the 2' position: $C.sub._1$ to $C.sub._{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-methoxyethoxy (2'-O—$CH_2CH_2OCH_3$, also known as 2'-O-(2-methoxyethyl) or 2'-MOE) [Martin et al., Helv. Chim. Acta, 78:486-504 (1995)], 2'-dimethylaminooxyethoxy ($O(CH_2)_2ON(CH_3)_2$ group, also known as 2'-DMAOE), 2'-methoxy(2'-O—CH3), 2'-aminopropoxy(2'-$OCH_2CH_2CH_2NH_2$) and 2'-fluoro (2'-F).

Similar modifications may also be made at other positions on the polynucleotide probes or primers, particularly the 3' position of the sugar on the 3' terminal nucleotide or in 2'-5' linked oligonucleotides and the 5' position of 5' terminal nucleotide. Polynucleotide probes or primers may also have sugar mimetics such as cyclobutyl moieties in place of the pentofuranosyl sugar.

Polynucleotide probes or primers may also include modifications or substitutions to the nucleobase. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. I., ed. John Wiley & Sons; Englisch et al., Angewandte Chemie, Int. Ed., 30:613 (1991); and Sanghvi, Y. S., (1993) Antisense Research and Applications, pp 289-302, Crooke, S. T. and Lebleu, B., ed., CRC Press. Certain of these nucleobases are particularly useful for increasing the binding affinity of the polynucleotide probes of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi, Y. S., (1993) Antisense Research and Applications, pp 276-278, Crooke, S. T. and Lebleu, B., ed., CRC Press, Boca Raton].

One skilled in the art will recognize that it is not necessary for all positions in a given polynucleotide probe or primer to be uniformly modified. The present disclosure, therefore, contemplates the incorporation of more than one of the aforementioned modifications into a single polynucleotide probe or even at a single nucleoside within the probe or primer.

One skilled in the art will also appreciate that the nucleotide sequence of the entire length of the polynucleotide probe or primer does not need to be derived from the target sequence. Thus, for example, the polynucleotide probe may comprise nucleotide sequences at the 5' and/or 3' to the transcription start and stop sites, respectively that are not derived from the target sequences. Nucleotide sequences which are not derived from the nucleotide sequence of the target sequence may provide additional functionality to the polynucleotide probe. For example, they may provide a restriction enzyme recognition sequence or a "tag" that facilitates detection, isolation, purification or immobilisation onto a solid support. Alternatively, the additional nucleotides may provide a self-complementary sequence that allows the primer/probe to adopt a hairpin configuration. Such configurations are necessary for certain probes, for example, molecular beacon and Scorpion probes, which can be used in solution hybridization techniques.

The polynucleotide probes or primers can incorporate moieties useful in detection, isolation, purification, or immobilisation, if desired. Such moieties are well-known in the art (see, for example, Ausubel et al., (1997 & updates) Current Protocols in Molecular Biology, Wiley & Sons, New York) and are chosen such that the ability of the probe to hybridize with its target sequence is not affected.

Examples of suitable moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the disclosure include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the invention. A variety of different coding schemes are known in the art, including fluorophores, including SCNCs, deposited metals, and RF tags.

Polynucleotides from the described target sequences may be employed as probes for detecting target sequences expression, for ligation amplification schemes, or may be used as primers for amplification schemes of all or a portion of a target sequences. When amplified, either strand produced by amplification may be provided in purified and/or isolated form.

In some embodiments, polynucleotides of the disclosure include a nucleic acid depicted in (a) any of SEQ ID NOs: 1-98; (b) an RNA form of any of the nucleic acids depicted in SEQ ID NOs: 1-98; (c) a peptide nucleic acid form of any of the nucleic acids depicted in SEQ ID NOs: 1-98; (d) a nucleic acid comprising at least 20 consecutive bases of any of (a-c); (e) a nucleic acid comprising at least 25 consecutive bases having at least 90% sequence identity to any of (a-c); and a complement to any of (a-e).

Complements may take any polymeric form capable of base pairing to the species recited in (a)-(e), including nucleic acid such as RNA or DNA, or may be a neutral polymer such as a peptide nucleic acid. Polynucleotides of the disclosure can be selected from the subsets of the recited nucleic acids described herein, as well as their complements.

In some embodiments, polynucleotides of the disclosure comprise at least 20 consecutive bases as depicted in SEQ ID NOs:1-98, or a complement thereto. The polynucleotides may comprise at least 21, 22, 23, 24, 25, 27, 30, 32, 35 or more consecutive bases as depicted in SEQ ID NOs:1-98.

The polynucleotides may be provided in a variety of formats, including as solids, in solution, or in an array. The polynucleotides may optionally comprise one or more labels, which may be chemically and/or enzymatically incorporated into the polynucleotide.

In some embodiments, solutions comprising polynucleotide and a solvent are also provided. In some embodiments, the solvent may be water or may be predominantly aqueous. In some embodiments, the solution may comprise at least two, three, four, five, six, seven, eight, nine, ten, twelve, fifteen, seventeen, twenty or more different polynucleotides, including primers and primer pairs, of the invention. Additional substances may be included in the solution, alone or in combination, including one or more labels, additional solvents, buffers, biomolecules, polynucleotides, and one or more enzymes useful for performing methods described herein, including polymerases and ligases. The solution may further comprise a primer or primer pair capable of amplifying a polynucleotide of the invention present in the solution.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

H. Preparation of Probes and Primers

The polynucleotide probes or primers of the present disclosure can be prepared by conventional techniques well-known to those skilled in the art. For example, the polynucleotide probes can be prepared using solid-phase synthesis using commercially available equipment. As is well-known in the art, modified oligonucleotides can also be readily prepared by similar methods. The polynucleotide probes can also be synthesized directly on a solid support according to methods standard in the art. This method of synthesizing polynucleotides is particularly useful when the polynucleotide probes are part of a nucleic acid array.

Polynucleotide probes or primers can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261. Still further techniques include bead based techniques such as those described in PCT Appl. No. PCT/US93/04145 and pin based methods such as those described in U.S. Pat. No. 5,288,514. Additional flow channel or spotting methods applicable to attachment of sensor polynucleotides to a substrate are described in U.S. patent application Ser. No. 07/980,523, filed Nov. 20, 1992, and U.S. Pat. No. 5,384,261.

Alternatively, the polynucleotide probes of the present disclosure can be prepared by enzymatic digestion of the naturally occurring target gene, or mRNA or cDNA derived therefrom, by methods known in the art.

I. COPD Classification Methods

As demonstrated in the Examples, the inventors have made the surprising discovery that the expression of gene sets in the airway epithelium of a subject reflects the COPD disease status of the subject. That finding together with the identification of 98 different genes that are differentially expressed in the respiratory tract epithelium of subjects with COPD compared to normal control subjects has allowed the inventors to provide in this disclosure methods of classifying the COPD disease status of a subject.

Accordingly, this disclosure provides methods for classifying the chronic obstructive pulmonary disease (COPD) status of a subject. The methods comprise providing a tissue sample obtained from the respiratory tract epithelium of the subject. The methods further include determining the expression level of at least one transcript comprising (i) a sequence as set forth in any one of SEQ ID NOS. 1 to 98, (ii) a fragment of at least 100 nucleotides of a sequence as set forth in any one of SEQ ID NOS. 1 to 98, or (iii) a sequence with substantial homology to (i) or (ii), in the tissue sample to provide an expression pattern profile. The methods may further include comparing the expression pattern profile with a reference expression pattern profile. The methods may further include classifying the COPD status of the subject based on the comparing.

The methods use the COPD classification sets, probes and primers described herein to provide expression signatures or profiles from a test sample derived from the respiratory tract epithelium of a subject having or suspected of having COPD and/or undergoing a therapeutic intervention comprising administering an anti-COPD therapeutic agent. In some embodiments, such methods involve contacting the test sample with COPD classifying probes (either in solution or immobilized) under conditions that permit hybridization of the probe(s) to any target nucleic acid(s) present in the test sample and then detecting any probe:target duplexes formed as an indication of the presence of the target nucleic acid in the sample. Expression patterns thus determined are then compared to one or more reference profiles or signatures.

Optionally, the expression pattern can be normalized. The methods use the COPD classification sets, probes and primers described herein to provide expression signatures or profiles from a test sample derived from a subject to classify the COPD disease status of the subject.

The assay/method is capable in some embodiments of discriminating COPD disease status with good accuracy even without the need for a biopsy of lung tissue from the subject.

In some embodiments, such methods involve the specific amplification of target sequences nucleic acid(s) present in the test sample using methods known in the art to generate an expression profile or signature which is then compared to a reference profile or signature.

In some embodiments, the disclosure further provides for diagnosing COPD, for prognosing patient outcome, and/or for designating treatment modalities.

In some embodiments, the methods generate expression profiles or signatures detailing the expression of at least 2, at least 3, at least 4, at least 5, at least 10, at least 15, at least 20, at least 25, at least 30, at least 35, at least 40, at least 45, at least 50, at least 55, at least 65, at least 70, at least 75, at least 80, at least 85, at least 90, at least 95 or all 98 target sequences having altered relative expression in COPD disclosed herein. In some embodiments the methods generate expression profiles or signatures detailing the expression of each gene listed in Table B. In some embodiments the methods generate expression profiles or signatures detailing the expression of each gene listed in Table C. In some embodiments the methods generate expression profiles or signatures detailing the expression of each gene listed in Table D. In some embodiments the methods generate expression profiles or signatures detailing the expression of each gene listed in Table E. In some embodiments the methods generate expression profiles or signatures detailing the expression of each gene listed in Table F. In some embodiments the methods generate expression profiles or signatures detailing the expression of each gene listed in Table G.

In some embodiments, the methods detect combinations of expression levels of sequences exhibiting positive correlation with a disease status. In some embodiments, the methods detect a minimal expression signature.

Any method of detecting and/or quantitating the expression of the encoded target sequences can in principle be used in the methods of classifying the COPD disease status of a subject. Such methods can include Northern blotting, array or microarray hybridization, by enzymatic cleavage of specific structures (e.g., an Invader® assay, Third Wave Technologies, e.g. as described in U.S. Pat. Nos. 5,846,717; 6,090,543; 6,001,567; 5,985,557; and 5,994,069) and amplification methods, e.g. RT-PCR, including in a TaqMan® assay (PE Biosystems, Foster City, Calif., e.g. as described in U.S. Pat. Nos. 5,962,233 and 5,538,848), and may be quantitative or semi-quantitative, and may vary depending on the origin, amount and condition of the available biological sample. Combinations of these methods may also be used. For example, nucleic acids may be amplified, labeled and subjected to microarray analysis. Single-molecule sequencing (e.g., Illumina, Helicos, PacBio, ABI SOLID), in situ hybridization, bead-array technologies (e.g., Luminex xMAP, Illumina BeadChips), branched DNA technology (e.g., Panomics, Genisphere).

The expressed target sequences can be directly detected and/or quantitated, or may be copied and/or amplified to allow detection of amplified copies of the expressed target sequences or its complement. In some embodiments, degraded and/or fragmented RNA can be usefully analyzed for expression levels of target sequences, for example RNA having an RNA integrity number of less than about 8.

In some embodiments, quantitative RT-PCR assays are used to measure the expression level of at least one target sequence depicted in SEQ ID NOs: 1-98. In other embodiments, a GeneChip or microarray can be used to measure the expression of one or more of the target sequences.

Molecular assays measure the relative expression levels of the target sequences, which can be normalized to the expression levels of one or more control sequences, for example array control sequences and/or one or more housekeeping genes, for example GAPDH. Increased (or decreased) relative expression of the target sequences as described herein, including any of SEQ ID NOs:1-98, may thus be used alone or in any combination with each other in the methods described herein. In addition, negative control probes may be included.

In alternative methods the expression level of a protein listed in Table A is determined. In some embodiments the protein comprises a sequence as set forth in any one of SEQ ID NOS: 99-195. Any suitable method known in the art may be used to determine the protein expression level including mass spectroscopy or an antibody assay such as in situ hybridization, a Western blot, or an ELISA assay. Methods of generating antibodies against the proteins listed in Table A are well within the level of skill in the art. Skilled artisans will appreciate that in many assays a monoclonal antibody will be useful but is not necessarily required.

J. Diagnostic Samples

Diagnostic samples for use with the systems and in the methods of the present disclosure comprise nucleic acids suitable for providing RNA expression information. The biological sample from which the expressed RNA is obtained and analyzed for target sequence expression is obtained from the respiratory tract epithelium of the bronchi of a subject. In some embodiments the sample is obtained from the bronchi walls of at least one of sixth generation, seventh generation, and eighth generation bronchi of the subject. The diagnostic sample can be a biological sample used directly in a method of the invention. Alternatively, the diagnostic sample can be a sample prepared from a biological sample.

The sample may be archival sample, having a known and documented medical outcome, or may be a sample from a current patient whose ultimate medical outcome is not yet known. Samples to be analyzed for COPD are typically obtained as airway epithelium brushings, for example.

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Helv solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek®, V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFM™, Cryo-Gel™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

K. RNA Extraction

RNA can be extracted and purified from biological samples using any suitable technique. A number of techniques are known in the art, and several are commercially available (e.g., FormaPure™ nucleic acid extraction kit, Agencourt Biosciences, Beverly Mass., High Pure FFPE RNA Micro Kit™, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA concentrations can be made using a Nanodrop ND-1000 spectrophotometer (Nanodrop Technologies, Rockland, Del.). RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

L. Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a PSR, and may optionally be labeled. A variety of amplification methods are suitable for use, including polymerase-based methods and ligation-based methods. Exemplary amplification techniques include the polymerase chain reaction method (PCR), the ligase chain reaction (LCR), ribozyme-based methods, self sustained sequence replication (3SR), nucleic acid sequence-based amplification (NASBA), the use of Q Beta replicase, reverse transcription, nick translation, and the like.

Asymmetric amplification reactions may be used to preferentially amplify one strand representing the PSR that is used for detection as the target polynucleotide. In some cases, the presence and/or amount of the amplification product itself may be used to determine the expression level of a given PSR. In other instances, the amplification product may be used to hybridize to an array or other substrate comprising sensor polynucleotides which are used to detect and/or quantitate PSR expression.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H.sup.-MMLV (SuperScript®), SuperScript® II, ThermoScript®, HIV-1, and RAV2 reverse transcriptases. All of these enzymes are commercially available.

Exemplary polymerases with multiple specificities include RAV2 and Tli (exo-) polymerases. Exemplary thermostable polymerases include Tub, Taq, Tth, Pfx, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, Calif.), including the WT-Ovation™ System, WT-Ovation™ System v2, WT-Ovation™ Pico System, WT-Ovation™ FFPE Exon Module, WT-Ovation™ FFPE Exon Module RiboAmp and RiboAmpPlus RNA Amplification Kits (MDS Analytical Technologies (formerly Arcturus) (Mountain View, Calif.), Genisphere, Inc. (Hatfield, Pa.), including the RampUp Plus™ and SenseAmp™ RNA Amplification kits, alone or in combination. Amplified nucleic acids may be subjected to one or more purification reactions after amplification and labeling, for example using magnetic beads (e.g., RNAClean magnetic beads, Agencourt Biosciences).

Multiple RNA biomarkers can be analyzed using real-time quantitative multiplex RT-PCR platforms and other multiplexing technologies such as GenomeLab GeXP Genetic Analysis System (Beckman Coulter, Foster City, Calif.), SmartCycler® 9600 or GeneXpert® Systems (Cepheid, Sunnyvale, Calif.), ABI 7900 HT Fast Real Time PCR system (Applied Biosystems, Foster City, Calif.), LightCycler® 480 System (Roche Molecular Systems, Pleasanton, Calif.), xMAP 100 System (Luminex, Austin, Tex.) Solexa Genome Analysis System (Illumina, Hayward, Calif.), OpenArray Real Time qPCR (BioTrove, Woburn, Mass.) and BeadXpress System (Illumina, Hayward, Calif.).

M. COPD Classification Arrays

The present disclosure contemplates that a COPD classification set or probes derived therefrom may be provided in an array format. In the context of the present disclosure, an "array" is a spatially or logically organized collection of polynucleotide probes. Any array comprising sensor probes specific for two or more of the target sequences depicted in SEQ ID NOs: 1-98 or a product derived from the target sequences depicted therein can be used. Desirably, an array will be specific for at least 5, 10, 15, 20, 25, 30, 35, 40, 45, 50, 55, 60, 65, 70, 75, 80, 85, 90, 95 or all of SEQ ID NOs: 1-98. Expression of these sequences may be detected alone or in combination with other transcripts. In some embodiments, an array is used which comprises a wide range of sensor probes for COPD expression products, along with appropriate control sequences. An array of interest is the Human Exon 1.0 ST Array (HuEx 1.0 ST, Affymetrix, Inc., Santa Clara, Calif.).

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that will be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In some embodiments the COPD classification array is a chip.

N. Data Analysis

Array data (or other expression data) can be managed and analyzed using techniques known in the art. The Genetrix suite of tools can be used for microarray analysis (Epicenter Software, Pasadena, Calif.). Probe set modeling and data pre-processing can be derived using the Robust Multi-Array (RMA) algorithm or variant GC-RMA, Probe Logarithmic Intensity Error (PLIER) algorithm or variant iterPLIER. Variance or intensity filters can be applied to pre-process data using the RMA algorithm, for example by removing target sequences with a standard deviation of <10 or a mean intensity of <100 intensity units of a normalized data range, respectively.

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (i.e., an "expression signature") and converted into a likelihood score. This likelihood score indicates the probability that a biological sample is from a subject having COPD or at least one symptom thereof. The likelihood score can be used to distinguish classify COPD. The models and/or algorithms can be provided in machine readable format, and may be used to correlate expression levels or an expression profile with a disease state, and/or to designate a treatment modality for a subject, patient, or class of subjects/patients.

Thus, results of the expression level analysis can be used to correlate increased expression of one or more target sequences with COPD, and to designate a treatment modality based on the classification. For example, the treatment modality may be initiating or ceasing treatment by administration of at least one anti-COPD therapeutic agent.

Factors known in the art for diagnosing and/or suggesting, selecting, designating, recommending or otherwise determining a course of treatment for a patient or class of patients suspected of having COPD can be employed in combination with measurements of the target sequence expression.

Certified tests for classifying COPD disease status and/or designating treatment modalities are also provided. A certified test comprises a means for characterizing the expression levels of one or more of the target sequences of interest, and a certification from a government regulatory agency endorsing use of the test for classifying the COPD status of a biological sample.

In some embodiments, the certified test may comprise reagents for amplification reactions used to detect and/or quantitate expression of the target sequences to be characterized in the test. An array of probe nucleic acids can be used, with or without prior target amplification, for use in measuring target sequence expression.

The test is submitted to an agency having authority to certify the test for use in classifying COPD disease status of a subject. Results of detection of expression levels of the target sequences used in the test and correlation with disease status and/or outcome are submitted to the agency. A certification authorizing the diagnostic and/or prognostic use of the test is obtained.

Also provided are portfolios of expression levels comprising a plurality of normalized expression levels of the target sequences described herein, including SEQ ID NOs: 1-98. Such portfolios may be provided by performing the methods described herein to obtain expression levels from an individual patient or from a group of patients. The expression levels can be normalized by any method known in the art; exemplary normalization methods that can be used in various embodiments include Robust Multichip Average (RMA), probe logarithmic intensity error estimation (PLIER), non-linear fit (NLFIT) quantile-based and nonlinear normalization, and combinations thereof. Background correction can also be performed on the expression data; exemplary techniques useful for background correction include mode of intensities, normalized using median polish probe modeling and sketch-normalization.

In some embodiments, portfolios are established such that the combination of genes in the portfolio exhibit improved sensitivity and specificity relative to known methods. In considering a group of genes for inclusion in a portfolio, a small standard deviation in expression measurements correlates with greater specificity. Other measurements of variation such as correlation coefficients can also be used in this capacity. The invention also encompasses the above methods where the specificity is at least about 50% and at least about 60%. The invention also encompasses the above methods where the sensitivity is at least about 90%.

The gene expression profiles of each of the target sequences comprising the portfolio can fixed in a medium such as a computer readable medium. This can take a number of forms. For example, a table can be established into which the range of signals (e.g., intensity measurements) indicative of disease is input. Actual patient data can then be compared to the values in the table to determine whether the patient samples are normal, or indicate the presence of COPD. In a more sophisticated embodiment, patterns of the expression signals (e.g., fluorescent intensity) are recorded digitally or graphically.

Comparisons can also be used to determine whether the patient is not likely to experience COPD. The expression profiles of the samples are then compared to a control portfolio. If the sample expression patterns are consistent with the expression pattern for COPD then (in the absence of countervailing medical considerations) the patient is treated as one would treat a COPD patient. If the sample expression patterns are consistent with the expression pattern from the normal/control cell then the patient is diagnosed negative for COPD.

Genes can be grouped so that information obtained about the set of genes in the group can be used to make or assist in making a clinically relevant judgment such as a diagnosis, prognosis, or treatment choice.

A patient report is also provided comprising a representation of measured expression levels of a plurality of target sequences in a biological sample from the patient, wherein the representation comprises expression levels of target sequences corresponding to any one, two, three, four, five, six, eight, ten, twenty, thirty, fifty or more of the target sequences depicted in SEQ ID NOs: 1-98, or of the subsets described herein, or of a combination thereof. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known COPD status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in dif-

O. Kits

Kits for performing the desired method(s) are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. At least two, three, four or five primers or pairs of primers suitable for selectively amplifying the same number of target sequence-specific polynucleotides can be provided in kit form. In some embodiments, the kit comprises from five to fifty primers or pairs of primers suitable for amplifying the same number of target sequence-representative polynucleotides of interest.

The reagents may independently be in liquid or solid form. The reagents may be provided in mixtures. Control samples and/or nucleic acids may optionally be provided in the kit. Control samples may include tissue and/or nucleic acids obtained from or representative of the presence of COPD disease in a subject, as well as tissue and/or nucleic acids obtained from or representative of the presence of COPD disease in a subject.

The nucleic acids may be provided in an array format, and thus an array or microarray may be included in the kit. The kit optionally may be certified by a government agency for use in classifying the disease status of COPD tissue and/or for designating a treatment modality.

Instructions for using the kit to perform one or more methods of the disclosure can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

P. Devices

Devices useful for performing methods of the disclosure are also provided. The devices can comprise means for characterizing the expression level of a target sequence of the invention, for example components for performing one or more methods of nucleic acid extraction, amplification, and/or detection. Such components may include one or more of an amplification chamber (for example a thermal cycler), a plate reader, a spectrophotometer, capillary electrophoresis apparatus, a chip reader, and or robotic sample handling components. These components ultimately can obtain data that reflects the expression level of the target sequences used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection components.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

The devices also comprise a means for correlating the expression levels of the target sequences being studied with a classification of COPD. Such means may comprise one or more of a variety of correlative techniques, including lookup tables, algorithms, multivariate models, and linear or non-linear combinations of expression models or algorithms. The expression levels may be converted to one or more likelihood scores, reflecting the likelihood that the sample is from a subject with COPD and/or is from a subject without COPD. The models and/or algorithms can be provided in machine readable format, and can optionally further designate a treatment modality for a patient or class of patients.

The device also comprises output means for outputting the COPD disease status and/or a treatment modality. Such output means can take any form which transmits the results to a patient and/or a healthcare provider, and may include a monitor, a printed format, or both. The device may use a computer system for performing one or more of the steps provided.

Q. Methods of Treatment

The methods and systems of this disclosure also find use in conjunction with treatment of COPD in a subject. For example, the methods and systems may be used to identify a subject or a class of subjects as suitable for treatment with at least one anti-COPD therapeutic agent. The methods and systems may also be used to monitor the response of a patient or a class of patients to treatment with at least one anti-COPD therapeutic agent. As a result of the monitoring the treatment course may be modified, discontinued, or continued, for example.

Generally the treatment methods include providing a tissue sample obtained from the respiratory tract epithelium of a subject. The methods may also include determining the expression level of at least one transcript comprising (i) a sequence as set forth in any one of SEQ ID NOS. 1 to 98, (ii) a fragment of at least 100 nucleotides of a sequence as set forth in any one of SEQ ID NOS. 1 to 98, or (iii) a sequence with substantial homology to (i) or (ii), in the tissue sample to provide an expression pattern profile. In some embodiments the expression level of at least 5, 10, 15, 20, 25, 30, 35, 40, 45, 50, 55, 60, 65, 70, 75, 80, 85, 90, 95 or 98 transcripts are determined, each such transcript comprising (i) a sequence as set forth in any one of SEQ ID NOS. 1 to 98, (ii) a fragment of at least 100 nucleotides of a sequence as set forth in any one of SEQ ID NOS. 1 to 98, or (iii) a sequence with substantial homology to (i) or (ii), in order to provide an expression pattern profile. In some embodiments the expression level of at least 5, 10, 15, 20, 25, 30, 35, 40, 45, 50 transcripts are determined, each such transcript comprising (i) a sequence as set forth in Table E, (ii) a fragment of at least 100 nucleotides of a sequence as set forth in Table E, or (iii) a sequence with substantial homology to (i) or (ii), in order to provide an expression pattern profile.

The methods may also include comparing the expression pattern profile with a reference expression pattern profile. The methods may also include classifying the COPD status of the subject based on the comparing. The methods may also include administering an anti-COPD therapeutic agent to the subject if the subject is classified as having active COPD disease status warranting therapeutic intervention. The methods may also include not administering an anti-COPD therapeutic agent to the subject if the subject is classified as not having active COPD disease status warranting therapeutic intervention. The methods may also include adjusting the dosing of the anti-COPD therapeutic agent based on the classification of the COPD disease status of the subject.

EXAMPLES

Methods

Patient Population

Bronchial airway brushings were obtained during bronchoscopy from subjects who were being followed longitudinally for the development of lung cancer at the British Columbia Cancer Research Agency between June 2000 and May 2009 as part of the British Columbia Lung Health Study (Tammemagi M C, et al. 2011. Incremental value of pulmonary function and sputum DNA image cytometry in lung cancer risk prediction. *Cancer Prev Res* 4:552-561.) and the Pan-Canadian Lung Health Study. A total of 267 bronchial brushing samples were selected to ensure matching for covariates (Table 1). All subjects provided written informed consent. Institutional review board approval was obtained from participating institutions. High molecular weight RNA isolated from the bronchial brushings using the miRNeasy mini kit (Qiagen, Valencia, Calif.) was processed and hybridized to Affymetrix Human Gene 1.0 ST Arrays.

Sample Collection

Brushings were obtained from the $6^{th}$ to $8^{th}$ generation bronchi using a 1.5 mm brush, immediately placed in 1.5 mL RNALater (Qiagen) and stored at −80 C until processing. A detailed questionnaire was completed for each subject which included age, race, ethnicity, a detailed smoking history, and medications. Spirometry was conducted as previously described (Tammemagi M C, et al. 2011. Incremental value of pulmonary function and sputum DNA image cytometry in lung cancer risk prediction. *Cancer Prev Res* 4:552-561) using flow-sensitive spirometer (Presto Flash Portable Spirometer Version 1.2) according to the American Thoracic Society recommendations. (1987. Standardization of spirometry—1987 update. Statement of the American Thoracic Society. *Am Rev Respir Dis* 136:1285-1298; 1995. Standardization of spirometry, 1994 Update. American Thoracic Society. *Am J Respir Crit Care Med* 152:1107-1136.)

Percent emphysema was quantified by calculating the percentage of low attenuation area on CT scan using a −950HU threshold as previously described. (Grydeland T B, et al. 2011. Quantitative CT measures of emphysema and airway wall thickness are related to D(L)CO. *Respir Med* 105:343-351; Grydeland T B, et al. 2010. Quantitative computed tomography measures of emphysema and airway wall thickness are related to respiratory symptoms. *Am J Respir Crit Care Med* 181:353-359.) Samples were selected on the basis of age, gender, smoking status, and pack-years of smoking to ensure that relevant co-variates were balanced between groups.

Sample Processing

High molecular weight RNA was isolated from the bronchial brushings using the miRNeasy mini kit (Qiagen) according to the manufacturer's protocol. Bronchial epithelial cells were lysed and homogenized in QIAzol Lysis Reagent. After chloroform extraction, the aqueous phase was mixed with ethanol and applied to an RNeasy Mini Spin Column in order to retain high molecular weight RNA (>200 nt). Column flow-through was collected, mixed with ethanol, and applied to an RNAEasy MinElute spin column to retain low molecular weight RNA. After washing, the high and low molecular weight RNA fractions were separately eluted from the columns. Large and small RNA quantity and purity was assessed using a NanoDrop ND-1000 spectrophotometer, and integrity assessed using an Agilent 2100 BioAnalyzer.

High molecular weight RNA from bronchial epithelial brushings was processed and hybridized to Affymetrix Human Gene 1.0 ST Arrays as described in the GeneChip® Whole Transcript (WT) Sense Target Labeling Assay Manual (Affymetrix). A total of 200 ng of high molecular weight RNA was reverse transcribed (Whole Transcript cDNA Synthesis Kit, Affymetrix, Santa Clara, Calif.). This was followed by in vitro transcription (IVT) (Whole Transcript cDNA Amplification Kit, Affymetrix, Santa Clara, Calif.), purification (GeneChip Sample Cleanup Module), and reverse transcription with dUTP incorporation (Whole Transcript cDNA Synthesis Kit). The resulting single-stranded DNA was fragmented using uracil DNA glycosylase (UDG) and apurinic/apyrimidinic endonuclease 1 (APE1), and labeled using DNA Labeling Reagent which is covalently linked to biotin with terminal deoxynucleotidyl transferase (TdT) (Whole Transcript Terminal Labeling Kit, Affymetrix, Santa Clara, Calif.). IVT and cDNA fragmentation quality was determined using the mRNA Nano Assay in the Agilent 2100 BioAnalyzer.

The labeled fragmented cDNA was hybridized to Affymetrix Human Gene 1.0 ST Arrays for 16-18 hours in the GeneChip Hybridization Oven 640 at 45 C with 60 rpm rotation. After washing, the hybridized samples were stained with strepavidin (SAPE), followed by signal amplification with a biotinylated goat anti-streptavidin antibody and a second SAPE stain using the Affymetrix Fluidics Station 450 (Hybridization Washing and Staining Kit, Affymetrix, Santa Clara, Calif.). Microarrays were immediately scanned using an Affymetrix GeneArray Scanner 3000 7G Plus (Affymetrix). (Zhang X, et al. 2010. Similarities and differences between smoking-related gene expression in the nasal and bronchial epithelium. *Physiol Genomics* 41:1-8.)

Data Acquisition, Probeset Summarization and Normalization, and Data Preprocessing A total of 269 arrays from 267 samples including two samples run in duplicate were used for the generation of gene expression levels. The array data for two subjects were excluded due to sample annotation concerns, leaving a total of 265 samples. To minimize the potential confounding effect of lung cancer, data from 19 subjects with a diagnosis of lung cancer as of January 2010 were excluded as were data from 8 subjects who lacked lung function testing within 1 year of their study bronchoscopy, leaving a total of 238 samples.

Gene expression estimates were derived from the probe hybridization intensities in the R statistical environment (R 2.9.2 and R 2.10.0) with the aroma.affymetrix package v1.4.0 (Bengtsson H, Simpson K, Bullard J, and Hansen K. aroma.affymetrix: A generic framework in R for analyzing small to very large Affymetrix data sets in bounded memory. Tech Report #745. 2008. Department of Statistics, University of California, Berkeley) using the Robust Multichip Average algorithm and the Entrez Gene Chip Definition File (CDF) v11.0.1. (Dai M, et al. 2005. Evolving gene/transcript definitions significantly alter the interpretation of GeneChip data. *Nucleic Acids Research* 33:e175.) Raw and processed microarray data has been deposited in the Gene Expression Omnibus (GEO) (GSE37147).

Microarray data quality was assessed using relative log expression (RLE) plots, normalized unscaled standard error (NUSE) plots, and principle component analysis (PCA) of all genes across all samples. As an additional quality control measure to exclude samples contaminated with inflammatory cells, hierarchical clustering was performed across epithelial and inflammatory cell specific genes as previously described. (Spira A, et al. 2004. Effects of cigarette smoke on the human airway epithelial cell transcriptome. *Proc Natl Acad Sci USA* 101:10143-10148.) A metagene representing inflammatory cell specific gene expression was calculated from the first principle component. The 238 samples from lung cancer-free current and former smokers with and without COPD were of adequate quality for subsequent analysis (FIG. 1).

Using spirometry measurements obtained within 1 year of bronchoscopy, COPD was defined as the presence of both an $FEV_1/FVC \leq 0.7$ and $FEV_1\%$ predicted <80, based on standard reference equations. (Tammemagi M C, et al. 2011. Incremental value of pulmonary function and sputum DNA image cytometry in lung cancer risk prediction. *Cancer Prev Res* 4:552-561; Crapo R O, Morris A H, and Gardner R M. 1981. Reference spirometric values using techniques and equipment that meet ATS recommendations. *Am Rev Respir Dis* 123:659-664.) Age (at time of bronchoscopy), gender, smoking status (current or former smoker), and cumulative tobacco exposure (calculated for the time of bronchoscopy) were used as covariates using the 222 samples with complete covariate data. For active smokers, pack years at the time of bronchoscopy was calculated from self-reported pack years at the time of last follow up, smoking duration and age at the time of last follow up, and age at the time of sample collection. For the ANOVA, models 1a-1c (below) were each compared to model 2.

$$ge_i = \beta_0 + \beta_1 x_{Age} + \beta_2 x_{Smoke\_Status} + \beta_3 x_{PY} + \beta_4 x_{Gender} + \beta_5 x_{COPD} + \epsilon_i \quad (1a)$$

$$ge_i = \beta_0 + \beta_1 x_{Age} + \beta_2 x_{Smoke\_Status} + \beta_3 x_{PY} + \beta_4 x_{Gender} + \beta_5 x_{FEV1/FVC} + \epsilon_i \quad (1b)$$

$$ge_i = \beta_0 + \beta_1 x_{Age} + \beta_2 x_{Smoke\_Status} + \beta_3 x_{PY} + \beta_4 x_{Gender} + \beta_5 x_{FEV1} + \epsilon_i \quad (1c)$$

$$ge_i = \beta_0 + \beta_1 x_{Age} + \beta_2 x_{Smoke\_Status} + \beta_3 x_{PY} + \beta_4 x_{Gender} + \epsilon_i \quad (2)$$

In these models, $ge_i$ represents the log 2-expression of gene i and $\epsilon_i$, represents the error assumed to be normally distributed. The false discovery rates (FDR) of the p-values from each ANOVA were calculated using the method of Benjamini and Hochberg. (Benjamini Y and Hochberg Y. 1995. Controlling the false discovery rate: a practical and powerful approach to multiple testing. *J R Statist Soc* 57:289-300.) Expression profiles of genes associated with COPD and continuous measures of lung function were organized by hierarchical clustering of z-score normalized relative expression levels using complete linkage clustering with a Euclidean distance metric. Cluster membership based on gene expression among individuals with COPD was determined using the cuttree function.

Genes whose expression levels were associated with COPD and/or continuous measures of lung function were identified by an ANOVA FDR of <0.05 and a linear fold change (FC) of >1.25 between COPD and No COPD after controlling for major demographic variables and risk factors for COPD.

Enrichment Analysis

Analysis to determine functional enrichment among the 98 genes whose expression was associated with COPD was performed using DAVID 6.7b. (Dennis G, et al. DAVID: Database for Annotation, Visualization, and Integrated Discovery. Genome Biol 4[5], P3. 2003.) Transcription factor binding site enrichment analysis was performed using GATHER. (GATHER: a systems approach to interpreting genomic signatures. 2006. Chang J T; Nevins J R. *Bioinformatics* 22:2926-2933.) Additional predicted targets of selected transcription factors were identified with patser using Transfac version 12.1. (Matys V, et al. 2006. TRANSFAC and its module TRANSCompel: transcriptional gene regulation in eukaryotes. *Nucleic Acids Res* 34(Database issue):D108-110; Hertz G Z and Stormo G D. 1999. Identifying DNA and protein patterns with statistically significant alignments of multiple sequences. *Bioinformatics* 15:563-577.) GSEA was used to determine the relationship between our results and previously published studies as detailed in the supplementary methods and Table 2. A false-discovery rate threshold of FDR<0.05 was used to determine significant enrichment by GSEA.

TABLE 2

Summary of study designs of previously published lung tissue gene expression studies in COPD

| Study | Patient population | Sample type | Sample size | COPD Definitions |
|---|---|---|---|---|
| GSE1122 (Golpon HA, et al. 2004. Emphysema Lung Tissue | Undergoing lung transplantation, or healthy donors whose lungs could not be used | Explanted lung tissue or surgically resected lung | N = 5 emphysema N = 6 alpha 1 antitrypsin deficiency | Severe emphysema |

TABLE 2-continued

Summary of study designs of previously published
lung tissue gene expression studies in COPD

| Study | Patient population | Sample type | Sample size | COPD Definitions |
|---|---|---|---|---|
| Gene Expression Profiling. Am J Respir Cell Mol Biol 31:595-600.) | for transplant | | N = 5 controls | |
| GSE8500 (Wang IM, et al. 2008. Gene Expression Profiling in Patients with Chronic Obstructive Pulmonary Disease and Lung Cancer. Am J Respir Crit Care Med 177:411) | Surgical resection of lung nodules | Surgically resected lung tissue | N = 3 GOLD3<br>N = 10 GOLD2<br>N = 9 GOLD1<br>N = 21 GOLD0<br>N = 5 nonsmokers* | GOLD classification |
| GSE8581 (Bhattacharya S, et al. 2009. Molecular biomarkers for quantitative and discrete COPD phenotyes. Am J Respir Cell Mol Biol 40:359-367) | Surgical resection of a lung nodule suspected to be cancer | Histologically normal tissue distant from the tumor margin | N = 15 cases<br>N = 18 controls<br>N = 23 unclassified† | FEV1/FVC < 0.7 and FEV1 < 70% predicted |
| GSE1650 (Spira A, et al. 2004. Gene Expression Profiling of Human Lung Tissue from Smokers with Severe Emphysema. Am J Respir Cell Mol Biol 31:601-610) | Cases: lung volume reduction surgery Controls: thoracotomy for suspicion of malignancy | Surgically resected lung tissue | N = 20 severe emphysema<br>N = 14 controls | FEV1 < 50% predicted |
| Ning et al. PNAS 2004 (Ning W, et al. 2004. Comprehensive gene expression profiles reveal pathways related to the pathogenesis of chronic obstructive pulmonary disease. Proc Natl Acad Sci USA 101:14895-14900) | Surgical lung specimens | Surgically resected lung tissue | N = 14 moderate (GOLD2) COPD<br>N = 12 controls | GOLD classification |
| GSE27597 (Campbell JD, et al. 2012. A gene expression signature of emphysema-related lung destruction and its reversal by the tripeptide GHK. Genome Med 4:67) | Undergoing lung transplantation, or healthy donors whose lungs could not be used for transplant | Lung tissue cores from explanted lung | N = 6 severe emphysema<br>N = 2 controls | Mean linear intercept |

Enrichment analysis of other gene expression datasets was performed using GSEA v2.07. (Mootha V K, et al. 2003. PGC-1α-responsive genes involved in oxidative phosphorylation are coordinately downregulated in human diabetes. *Nature Genetics* 34:267-273; Subramanian A, et al. 2005. Gene set enrichment analysis: A knowledge-based approach for interpreting genome-wide expression profiles. *Proc Natl Acad Sci USA* 102:15545-15550.) Enrichment p-values were calculated by gene set permutation (n=1000), and significant enrichment was determined by an FDR-corrected p-value of <0.05. The core enrichment genes, or leading edge subset, were defined by GSEA as the genes with the most contribution to the significant enrichment. To determine whether predicted transcription factor binding sites were enriched in the regulatory regions of the airway COPD gene-expression signature, analysis was performed using GATHER. (GATHER: a systems approach to interpreting genomic signatures. 2006. Chang J T; Nevins J R. *Bioinformatics* 22:2926-2933.) Significant enrichment was determined using a Bayes Factor of ≥6 and a p-value of <0.05.

GSE5058:

To determine whether COPD-associated changes in bronchial airway gene expression are concordant with those that occur in the small airway epithelium (10-12th generation bronchi), we examined a dataset of small-airway gene expression associated with COPD. (Tilley A E, et al. 2009. Down-regulation of the Notch pathway in human airway epithelium in association with smoking and chronic obstructive pulmonary disease. *Am J Respir Crit Care Med* 179: 457-466.) Data was normalized using the RMA algorithm and Entrez Gene CDF v11.0.1. (Dai M, et al. 2005. Evolving gene/transcript definitions significantly alter the interpretation of GeneChip data. *Nucleic Acids Research* 33:e175.) Genes were ranked according to the t-statistic from a t-test comparing small airway gene expression from subjects with GOLD 1-2 COPD (n=4) and healthy subjects with normal lung function (n=12). GSEA was used to compare this ranked list to the genes significantly altered in association with COPD in our study.

GSE1122, GSE8500, GSE8581, GSE1650:

To determine the relationship between COPD-associated changes in airway gene expression and gene expression changes in the more distal lung parenchyma, we re-analyzed several previously published gene expression datasets as previously described. (Campbell J D, et al. 2012. A gene expression signature of emphysema-related lung destruction and its reversal by the tripeptide GHK. Genome Med 4:67.) Briefly, raw data obtained from the Gene Expression Omnibus (GEO) were normalized using RMA and the Entrez Gene CDF v11.0.1. Data was analyzed using linear models including terms for COPD-related clinical variables available through GEO. For each dataset, gene expression profiles were ranked according to the association with categorical and continuous measures of COPD and lung function. GSEA was used to compare these ranked lists to the genes significantly altered in association with COPD in our study. GSEA was also used to compare a ranked list of COPD-associated changes in airway gene expression to the genes whose expression levels in the lung parenchyma were previously reported to be associated with COPD. (Spira A, et al. 2004. Gene Expression Profiling of Human Lung Tissue from Smokers with Severe Emphysema. *Am J Respir Cell Mol Biol* 31:601-610; Bhattacharya S, et al. 2009. Molecular biomarkers for quantitative and discrete COPD phenotypes. *Am J Respir Cell Mol Biol* 40:359-367; Ning W, et al. 2004. Comprehensive gene expression profiles reveal pathways related to the pathogenesis of chronic obstructive pulmonary disease. *Proc Natl Acad Sci USA* 101:14895-14900; Golpon H A, et al. 2004. Emphysema Lung Tissue Gene Expression Profiling. *Am J Respir Cell Mol Biol* 31:595-600; Wang I M, et al. 2008. Gene Expression Profiling in Patients with Chronic Obstructive Pulmonary Disease and Lung Cancer. *Am J Respir Crit Care Med* 177:411.

GSE27597:

We also sought to investigate the relationship between COPD-associated changes in airway gene expression and a model of disease progression (GSE27597). (Campbell J D, et al. 2012. A gene expression signature of emphysema-related lung destruction and its reversal by the tripeptide GHK. *Genome Med* 4:67.) This dataset modeled emphysema progression by profiling multiple lung parenchymal cores from six individuals with advanced COPD and two individuals without COPD. These cores represented a range of emphysema severities, quantified by the mean linear intercept (Lm), within each individual. Raw data were normalized using RMA, and analyzed using a linear mixed effects model including fixed effects for Lm and lung slice from which the core was obtained, and a random patient effect. Gene expression profiles were ranked according to association with Lm. GSEA was used to compare this ranked list to airway gene expression significantly altered in COPD.

Real Time PCR Validation of Gene Expression Associated with COPD

To confirm COPD-associated gene expression changes, quantitative real-time PCR (qRT-PCR) was performed as previously described. (Beane J, et al. 2011. Characterizing the impact of smoking and lung cancer on the airway transcriptome using RNA-Seq. *Cancer Prev Res* 4:803-817.) Relative expression of DUSP5, TMPRSS11D, SERPINB13, WIF1, and CLDN8 was calculated using the ΔΔCt method and 18S expression for normalization. Relative expression of PTGS2, NR4A1, C8orf4, and FOS was calculated using the ΔΔCt method and GAPDH expression for normalization.

Gene Expression Changes Associated With ATF4 Overexpression

Figures 1, 2:
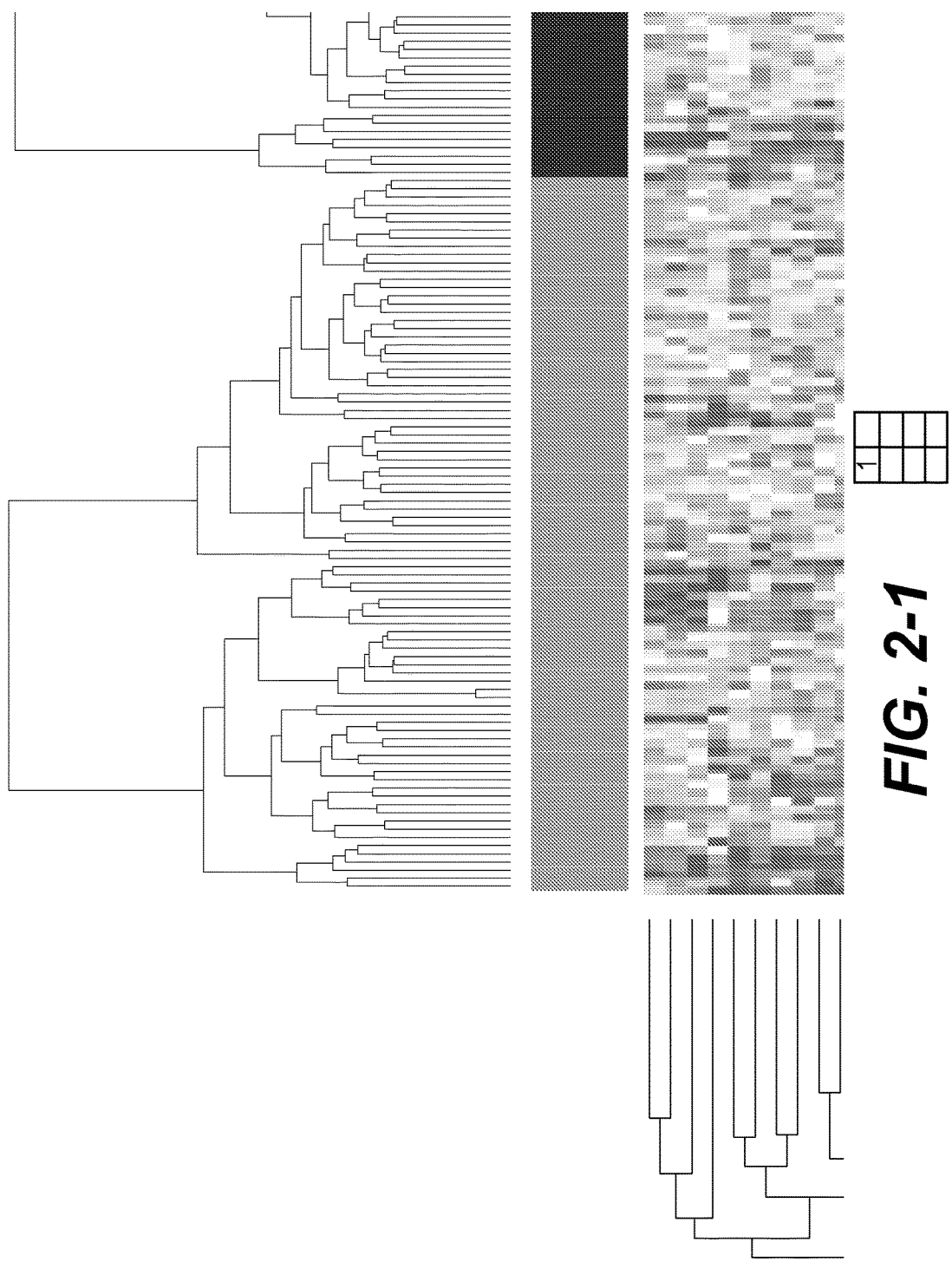
Figure 2:
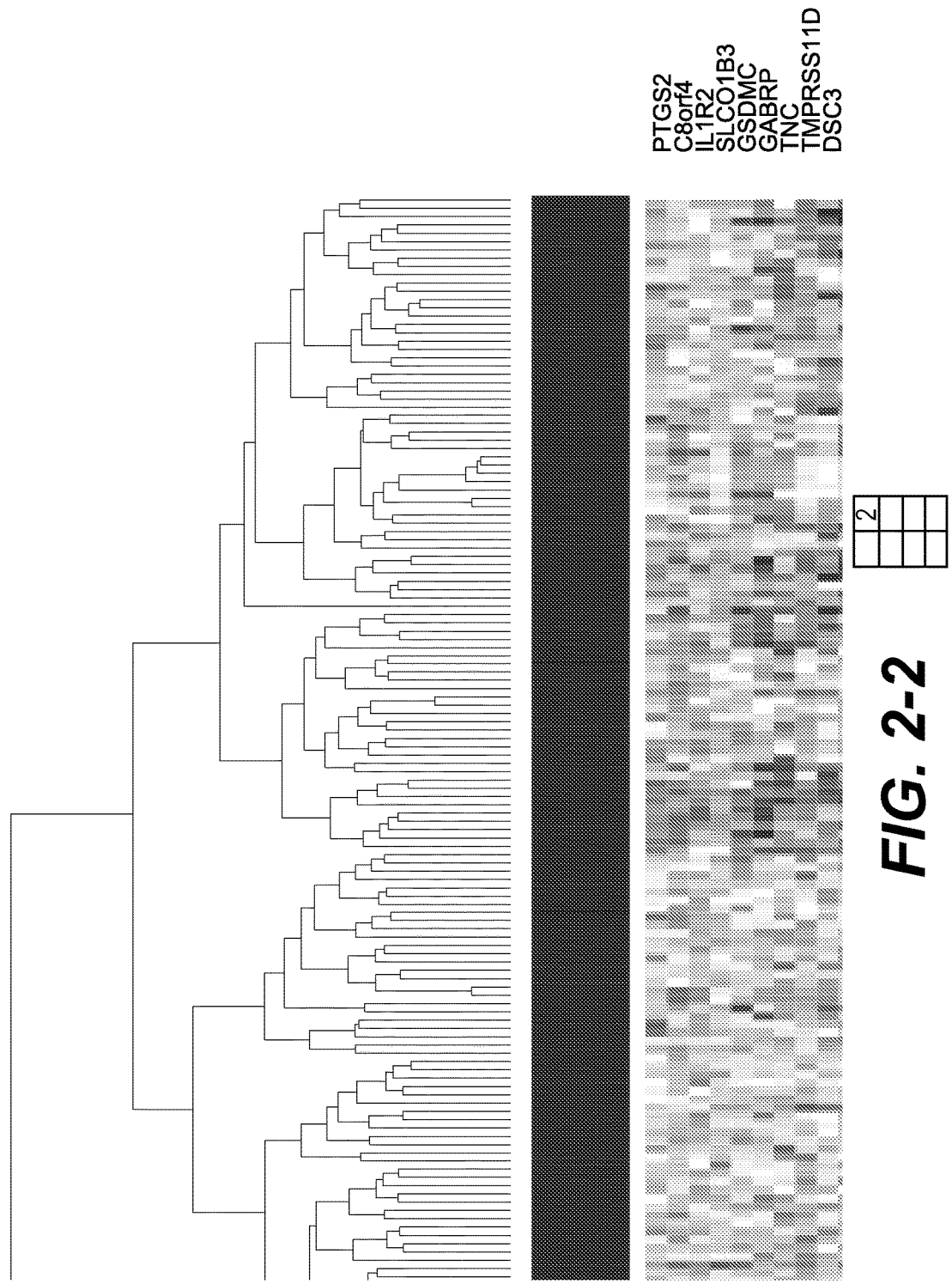
Figures 2, 3, 4:
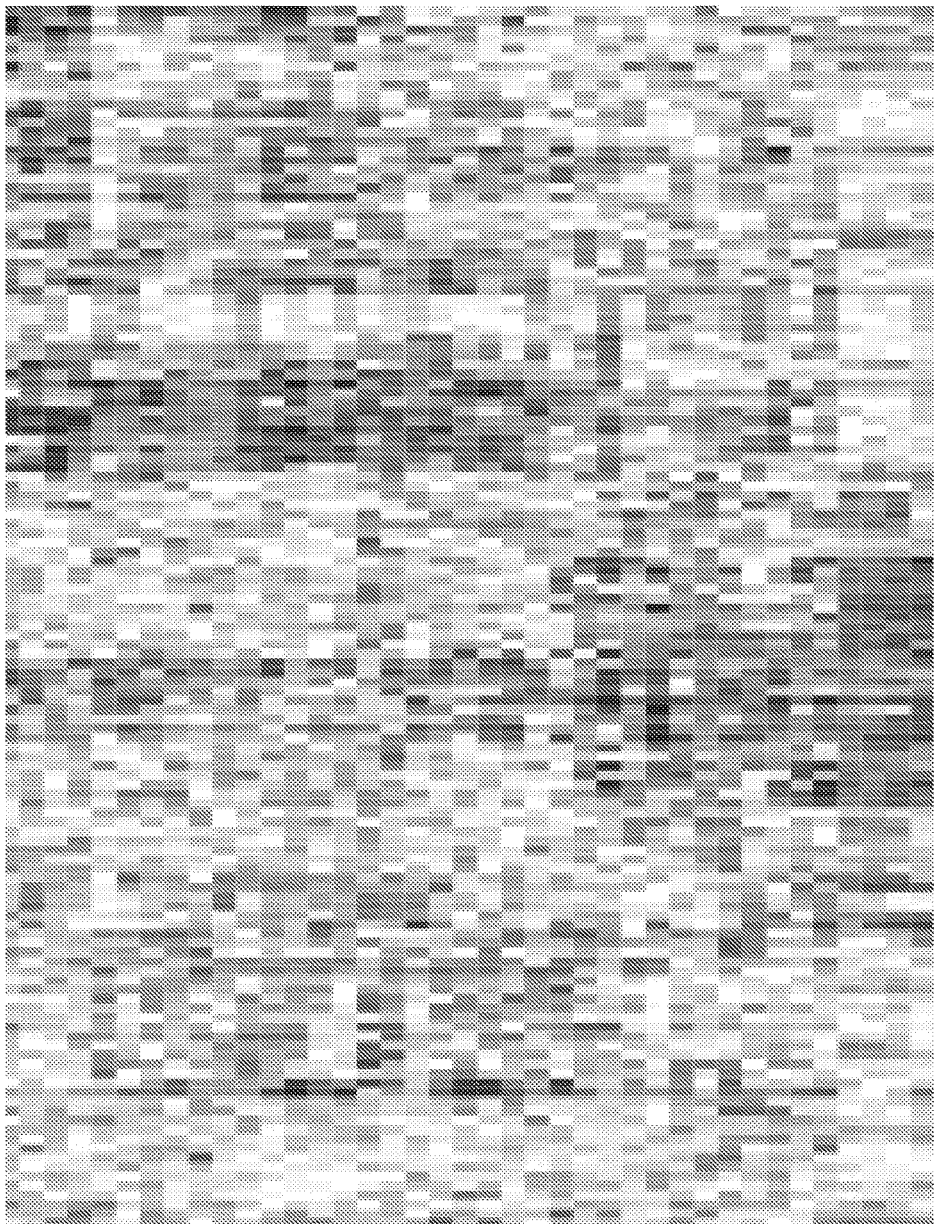
Figures 2, 3, 4, 5, 6:
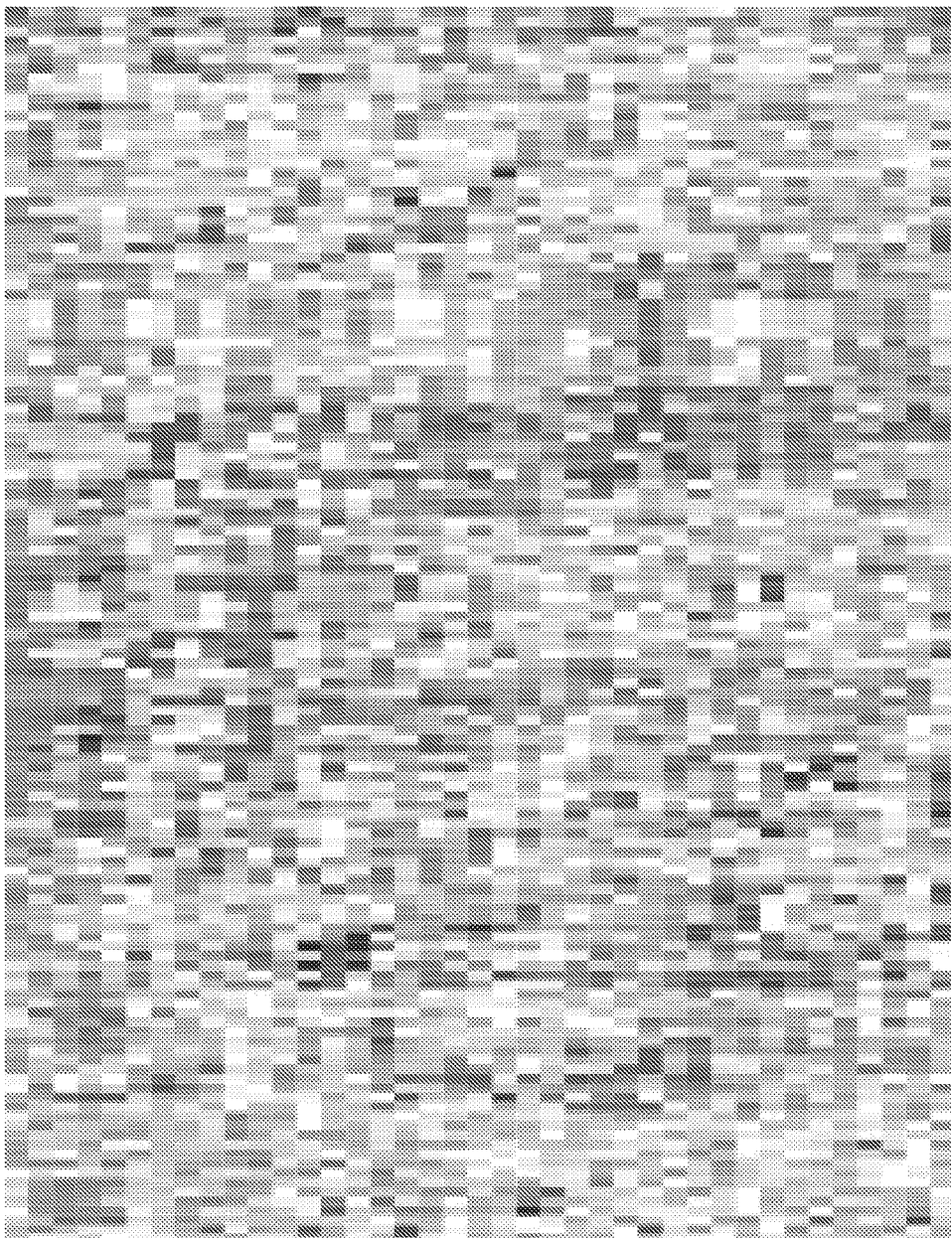
Figure 3:
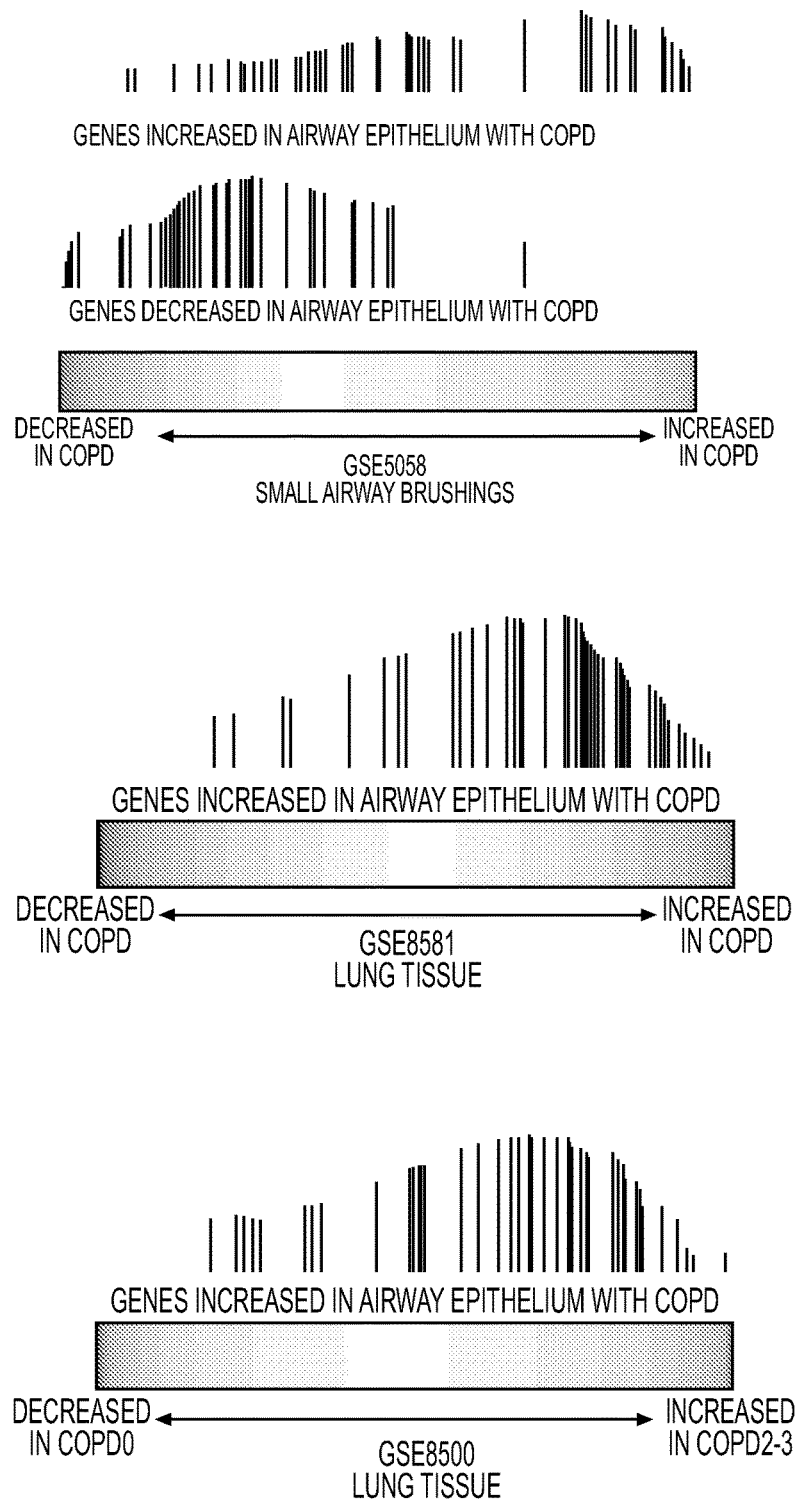
Figure 3:
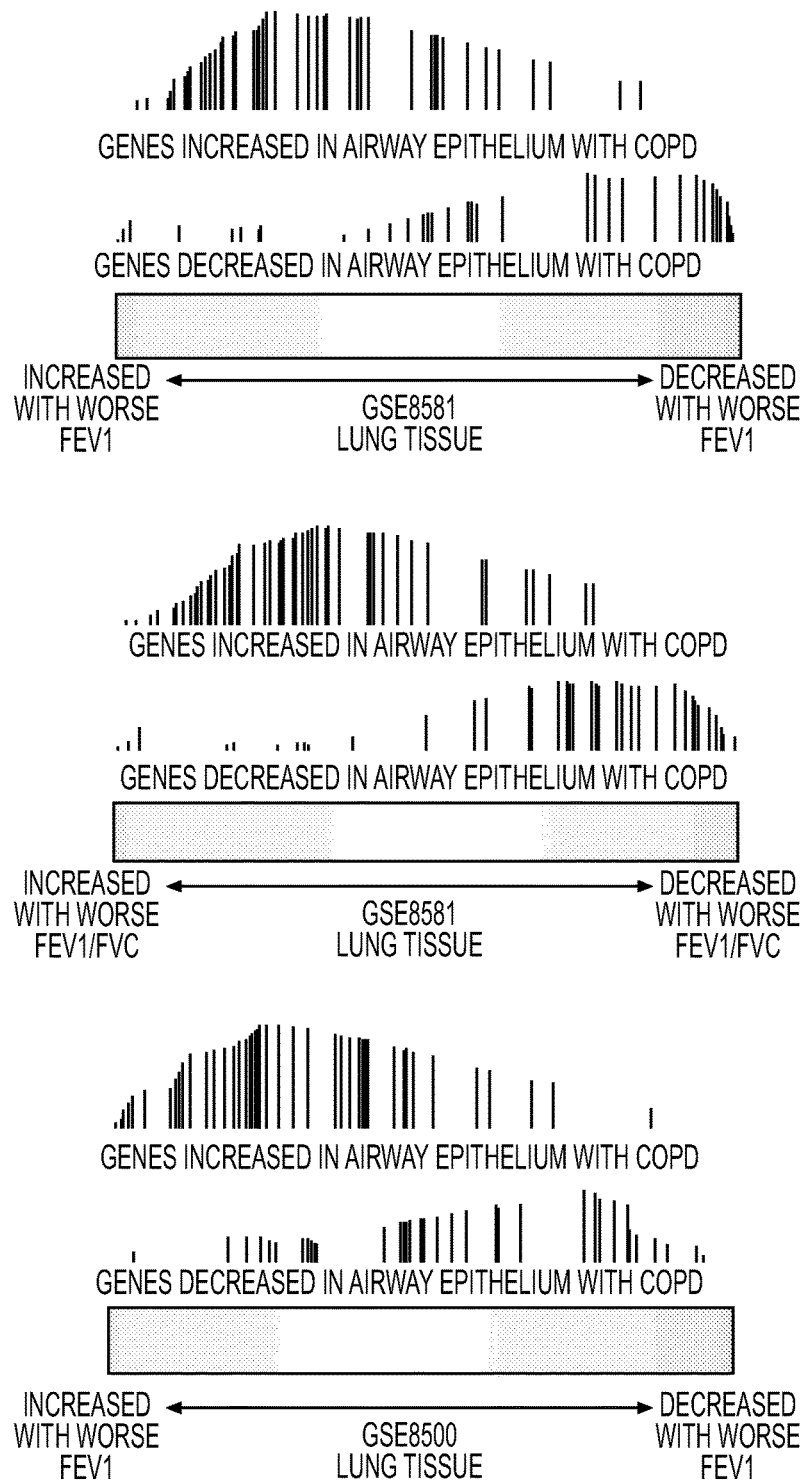
Figure 3:
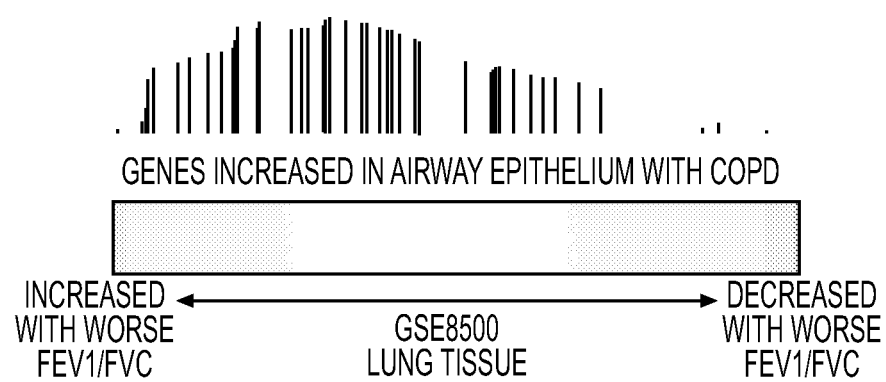
Figure 4:
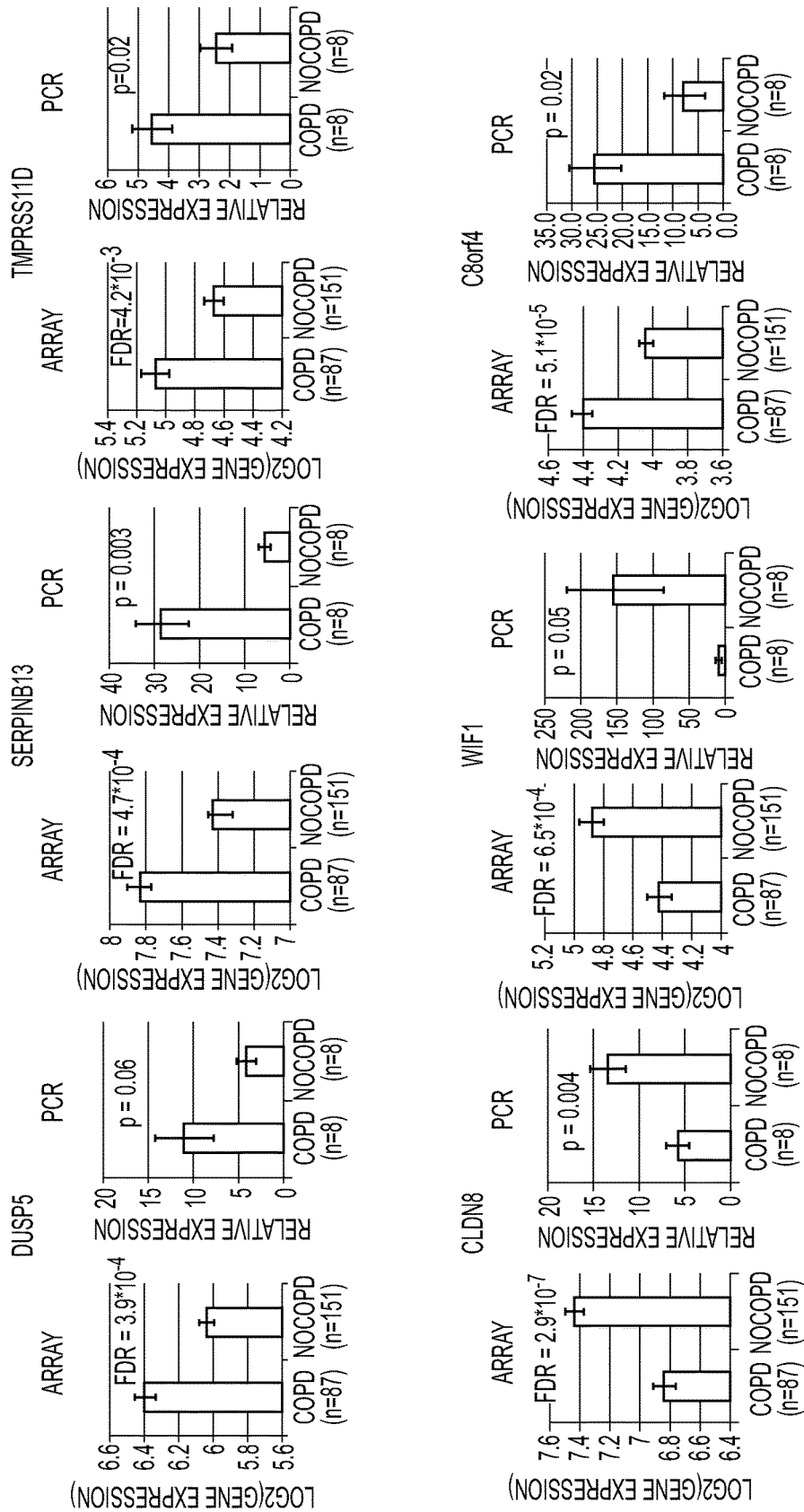
Figure 4:
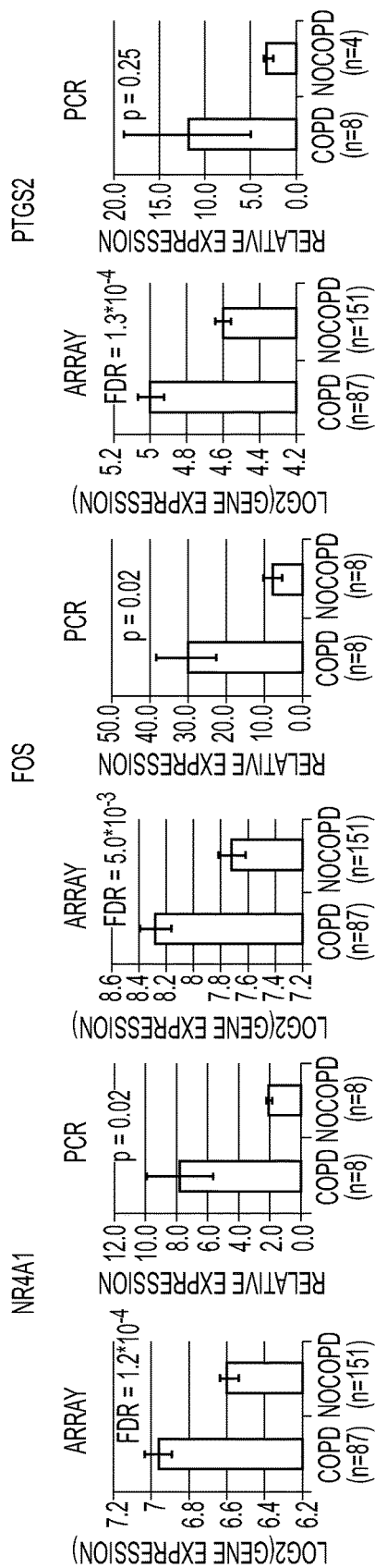

To determine the relationship between ATF4 expression and the airway COPD signature, we overexpressed ATF4 in immortalized human bronchial epithelial cells (BEAS2B). BEAS2B cells were cultured in BEGM growth medium (Lonza) and plated at an 80% confluence in 6-well plates 2411 before transfection. 3 ug of the plasmid SC119103 (human ATF4 cDNA cloned into a pCMV6-XL5 vector backbone; Origene) was transfected into the cells in triplicate using Lipofectamine 2000 (Invitrogen) as per manufacturer's protocol. 3 ug of an empty pCMV6-XL5 vector (Origene) was transfected into the cells in triplicate as a negative controls. Cells were harvested at 24 hours post-transfection and total RNA was isolated using the miRNeasy mini kit (Qiagen), ATF4 over-expression was confirmed by qRT-PCR (FIG. 6). Briefly, RNA was reverse transcribed using the $RT^2$ First Strand Kit (QIAQEN) and 4.5 ng of starting cDNA product together with 1 ul of 10 uM $RT^2$ qPCR primer assay were added to the $RT^2$ SYBR Green Mastermix (QIAGEN) as per manufacturer's protocol. Amplification (40 cycles), data acquisition, and data analysis were carried out using the StepOne Real Time PCR System (Applied Biosystems). Relative expression was calculated using the ΔΔCt method.

Total RNA was isolated from the BEAS2B cells transfected with ATF4 (n=3) or empty vector (n=3) at the 24 hour time point, processed, labeled, and hybridized to Affymetrix Human Gene 1.0 ST Arrays. Raw data were normalized using the RMA algorithm and Entrez Gene CDF v11.0.1[8]. (Dai M, et al. 2005. Evolving gene/transcript definitions significantly alter the interpretation of GeneChip data. *Nucleic Acids Research* 33:e175.) Gene expression differences induced by ATF4 overexpression were determined by t-test. Enrichment of the airway COPD signature among BEAS2B gene expression levels ranked according to association with ATF4 overexpression COPD was determined using GSEA.

Reversibility of COPD-Associated Airway Epithelial Gene Expression

GSE36221:

To determine the relationship between airway epithelial gene expression differences associated with COPD and treatment, we leveraged microarray data from 162 endobronchial biopsy samples obtained longitudinally from individuals with COPD randomized to receive fluticasone with (n=25 patients, n=61 samples) or without (n=20 patients, n=46 samples) salmeterol, or placebo (n=23 patients, n=55 samples) (Lapperre T S, et al, and Groningen Leiden Universities Corticosteroids in Obstructive Lung Disease Study Group. 2009. Effect of fluticasone with and without salmeterol on pulmonary outcomes in chronic obstructive pulmonary disease: a randomized trial. Ann Intern Med 151:517-527) (GSE36221) as part of the GLUCOLD trial (ClinicalTrials.gov registration number: NCT00158847) (FIG. 1). Samples were obtained a baseline prior to treatment, and at 6-months and 30-months after the initiation of treatment. After adjusting for RNA quality as measured by RIN and for patient, genes were ranked according to the t-statistic for longitudinal gene expression associated with fluticasone-containing treatment. Enrichment of airway epithelial gene expression associated with COPD was determined using GSEA, with an FDR<0.05 indicating significant enrichment.

GSE4302:

To identify a fluticasone-specific pattern of gene expression, we examined data from a whole-genome gene expression study of bronchial brushings obtained from asthmatics before and after treatment with fluticasone. (Woodruff P G, et al. 2007. Genome-wide profiling identifies epithelial cell genes associated with asthma and with treatment response to corticosteroids. Proc Natl Acad Sci USA 104:15858-15863.) Raw data were normalized using the RMA algorithm and Entrez Gene CDF v11.0.1. (Dai M, et al. 2005. Evolving gene/transcript definitions significantly alter the interpretation of GeneChip data. Nucleic Acids Research 33:e175.) Data from before and after treatment with fluticasone (n=19) or placebo (n=13) were analyzed using a linear mixed effects model including terms for time, treatment, and the interaction between time and treatment. Gene expression was ranked according to the magnitude of fluticasone-associated changes using the t-value for the time:treatment interaction term. Enrichment of the airway COPD signature among fluticasone-associated gene expression changes was determined using GSEA.

Example 1: Characteristics of the Study Population

There were no significant differences in age, cumulative smoking exposure, or smoking status between the 87 subjects with COPD and the 151 subjects without COPD (Table 1). Subjects with COPD had lower FEV1% predicted and FEV1/FVC than the control group. The FEV1 across subjects with COPD ranged from 15-79% of the reference value, with most COPD subjects having moderate disease (Global Initiative for Obstructive Lung Disease (GOLD) Grade 2) (Global initiative for chronic obstructive lung disease. 2011. Global initiative for chronic obstructive lung disease: Global strategy for the diagnosis, management, and prevention of chronic obstructive pulmonary disease.) as would be expected from a bronchoscopy-based cohort. A minority of the study population used inhaled corticosteroids or inhaled bronchodilators, with a statistically significant association with COPD status. Of the 14 subjects without COPD taking an inhaled medication, 3 had a history of asthma. A total of 17 subjects (8 with COPD and 9 without COPD) reported a history of asthma. Groups also differed with respect to statin use. There was no significant difference in the use of non-steroidal anti-inflammatory drugs (NSAID).

TABLE 1

Clinical Characteristics of the Study Population

| | COPD (n = 87)[‡] | No COPD (n = 151)[‡] | P-value* |
|---|---|---|---|
| Age in years | 65 (6) | 64 (6) | 0.25 |
| Gender | 52 Male | 83 Male | 0.5 |
| | 35 Female | 68 Female | |
| Smoking Status | 30 Current | 69 Current | 0.1 |
| | 57 Former | 82 Former | |
| Pack Years | 51 (25)[†] | 47 (19)[†] | 0.11 |
| $FEV_1$ % predicted | 60 (14) | 93 (13) | $<10^{-4}$ |
| $FEV_1/FVC$ | 0.56 (0.09) | 0.75 (0.06) | $<10^{-4}$ |
| Years since smoking cessation | 11.84 (9.86) | 11.11 (6.73) | 0.52 |
| Inhaled corticosteroid use | 18 (21%) | 7 (5%) | $<10^{-3}$ |
| Inhaled bronchodilator use | 21 (24%) | 11 (7%) | $<10^{-3}$ |
| Statin use | 23 (26%) | 23 (15%) | 0.041 |
| Nonsteroidal anti-inflammatory drug (NSAID) use | 21 (24%) | 46 (30%) | 0.37 |

The mean and standard deviation are shown for continuous variables.
*P-values were calculated using a Student's t-test or Fisher exact test.
[†]Missing PY for 5 subjects with COPD, and 11 subjects without COPD
[‡]97% of the subjects were Caucasian Example 2: Bronchial Epithelial Gene Expression Associated With COPD and Continuous Measures of Lung Function The expression levels of 107 genes were associated with COPD (FDR<0.05 and FC>1.25) after adjusting for major demographic variables and risk factors for COPD including age, gender, smoking status and cumulative smoke exposure. The expression levels of 110 genes were associated with $FEV_1$% predicted, and 102 with $FEV_1/FVC$ as continuous measures. The expression profiles of 98 genes were associated with all three measures; 54 of these genes were increased, and 44 were decreased in COPD (FIG. 2). This bronchial airway signature of COPD includes dihydropyrimidinase-like 3 (DPYSL3), CEACAM5, Sushi-repeat containing protein X-linked (SRPX), and enoyl-CoA delta isomerase 2 (PECI), four genes described in prior studies as irreversibly altered by cigarette smoke even decades after smoking cessation. (Beane J, et al. 2007. Reversible and permanent effects of tobacco smoke exposure on airway epithelial gene expression. *Genome Biol* 8:R201; and Spira A, et al. 2004. Effects of cigarette smoke on the human airway epithelial cell transcriptome. *Proc Natl Acad Sci USA* 101:10143-10148.) Among individuals with COPD, cluster membership in FIG. 2 was significantly associated with FEV1% predicted but not other clinical co-variates or RNA quality (Table 3). Further analysis of potential sources of the gene expression variability within classes is presented below.

TABLE 3

Association of COPD Sample Clusters With Clinical Co-Variates

| | COPD | | |
|---|---|---|---|
| | Cluster 1 (n = 40) | Cluster 2 (n = 47) | P-Value* |
| Age | 64 (6) | 66 (6) | 0.29 |
| Sex | 21 Male 19 Female | 31 Male 16 Female | 0.27 |
| Smoking Status | 17 Current 23 Former | 13 Current 34 Former | 0.18 |
| Pack Years | 52 (18)* | 50 (29)* | 0.73 |
| FEV1 % | 56 (15) | 64 (11) | 0.0038 |
| FEV1/FVC | 58 (10) | 61 (8) | 0.14 |
| % Emphysema | 10 (6)† | 14 (10)† | 0.08 |
| Inhaled corticosteroid use | 9 | 9 | 0.79 |
| Inhaled bronchodilator use | 9 | 10 | 0.13 |
| Statin use | 7 | 16 | 0.09 |
| NSAID use | 8 | 13 | 0.46 |
| RNA Integrity Number | 8 (1)‡ | 8 (1)‡ | 0.49 |

The mean and standard deviation are shown for continuous variables.
*Cluster 1 missing three values. Cluster 2 missing two values.
†Cluster 1 missing sixteen values. Cluster 2 missing five values.
‡Cluster 1 missing eighteen values. Cluster 2 missing thirteen values.

To determine whether asthma, inhaled medications, statin use, or the method of COPD classification affected this analysis, we repeated the analysis excluding individuals with a self-reported history of asthma (n=17), individuals using an inhaled corticosteroid or bronchodilator (n=37), individuals using a statin medication (n=46), or individuals with mild decreases in $FEV_1$% predicted (range: 70-80%) (n=49). We identified a consistent relationship between COPD-associated changes in airway gene expression in each of these analyses, with 80-99% of the 98 COPD-associated genes also showing an FDR<0.05 and FC>1.25 in these analyses (Table 4). We did not detect significant correlation of a metagene summarizing the COPD airway gene expression signature with years since quitting smoking among former smokers (p>0.05). We also failed to detect significant association between COPD status and a metagene representing inflammatory cell-specific gene expression. (Spira A, et al. 2004. Effects of cigarette smoke on the human airway epithelial cell transcriptome. *Proc Natl Acad Sci USA* 101: 10143-10148.) When the inflammatory cell metagene was included as a covariate in the linear model, all 98 COPD-associated genes remained significant at FDR<0.05 and FC>1.25.

TABLE 4

Concordance of COPD-Associated Bronchial Airway Gene Expression Changes in Sub-Group Analyses

| Samples excluded | Sample size of sub-groups | Number of COPD-associated genes* | Overlap with 98-gene COPD signature |
|---|---|---|---|
| History of asthma (n = 17) | 79 COPD 142 NoCOPD | 95 | 96% (94/98) |
| Inhaled medications (n = 37) | 64 COPD 137 NoCOPD | 78 | 80% (78/98) |
| Statin medications (n = 46) | 64 COPD 128 NoCOPD | 96 | 96% (94/98) |
| Mild decrease in $FEV_1$ % predicted (n = 49) | 62 COPD 127 NoCOPD | 99 | 99% (97/98) |

*Significant association of gene expression with COPD and continuous measures of lung function was determined as described in the methods.

To computationally validate the association of these genes with COPD, we performed Gene Set Enrichment Analysis (GSEA) using a publicly-available whole-genome gene-expression dataset of small airway epithelium (10th-12th generation bronchi) that included 12 healthy smokers and 4 smokers with COPD in GOLD Grade 1-2 severity (GSE5058). (Tilley A E, et al. 2009. Down-regulation of the Notch pathway in human airway epithelium in association with smoking and chronic obstructive pulmonary disease. *Am J Respir Crit Care Med* 179:457-466.) We identified a concordant relationship between the 98 genes whose expression patterns were associated with COPD in the present study and COPD-associated gene expression differences observed in this dataset ($FDR_{GSEA}$<0.05; FIG. 3). We also experimentally validated the COPD-associated expression pattern of 9 genes via qRT-PCR (FIG. 4). Together, these data identify a COPD-associated bronchial airway field of injury that reflects the presence and severity of COPD and that is consistent with COPD-associated gene expression changes in 10th to 12th generation bronchi. This finding is unexpected and surprising and identifies these genes as useful markers of COPD disease status.

To explore the biologic function of the 98 genes whose expression levels were associated with COPD, $FEV_1$% predicted, and $FEV_1$/FVC, genes were subdivided into two groups: 1) higher expression in COPD and 2) lower expression in COPD (FIG. 2). Both lists were significantly enriched for genes belonging to a variety of functional categories (Table 5) including glycoproteins (up-regulated), proteins involved in the acute inflammatory response (up-regulated), and EGF-like domains (down-regulated). These findings suggest that these gene expression changes reflect COPD-associated alterations in processes related to the inflammatory response and regulation of cell growth in bronchial airway epithelium.

TABLE 5

Functional Enrichment Among the 98 Genes Whose Expression in the Bronchial Epithelium is Associated With COPD

| Gene Cluster | Enriched Category | Modified Fisher Exact P-Value | Benjamini P-Value |
|---|---|---|---|
| Up-regulated in COPD | glycoprotein (SP_PIR_KEYWORD) | $3.30 * 10^{-6}$ | $1.20 * 10^{-3}$ |
| | SAA (SMART) | $2.10 * 10^{-7}$ | $2.40 * 10^{-3}$ |
| | PIRSF002472: Serum amyloid A (PIR_SUPERFAMILY) | $6.00 * 10^{-7}$ | $2.60 * 10^{-3}$ |
| | PIRSF002472: amyloid protein, SAA type (PIR_SUPERFAMILY) | $2.40 * 10^{-7}$ | $3.10 * 10^{-3}$ |

TABLE 5-continued

Functional Enrichment Among the 98 Genes Whose Expression in the Bronchial Epithelium is Associated With COPD

| Gene Cluster | Enriched Category | Modified Fisher Exact P-Value | Benjamini P-Value |
|---|---|---|---|
| | acute phase (SP_PIR_KEYWORD) | $1.1010^{-6}$ | $4.80 * 10^{-3}$ |
| | signal (SP_PIR_KEYWORDS) | $1.70 * 10^{-4}$ | $1.50 * 10^{-2}$ |
| | Secreted (SP_PIR_KEYWORDS) | $1.10 * 10^{-4}$ | $1.80 * 10^{-2}$ |
| | hdl (SP_PIR_KEYWORDS) | $1.50 * 10^{-5}$ | $3.20 * 10^{-2}$ |
| | polymorphism (SP_PIR_KEYWORDS) | $1.20 * 10^{-3}$ | $4.20 * 10^{-2}$ |
| | amyloid (SP_PIR_KEYWORDS) | $4.10 * 10^{-5}$ | $4.30 * 10^{-2}$ |
| | glycosylation site: N-linked (GlcNAc . . .) (UP_SEQ_FEATURE) | $2.20 * 10^{-4}$ | $4.70 * 10^{-2}$ |
| | disulfide bond (SP_PIR_KEYWORDS) | $1.30 * 10^{-3}$ | $5.30 * 10^{-2}$ |
| | insoluble fraction (GOTERM_CC_FAT) | $1.10 * 10^{-3}$ | $7.30 * 10^{-2}$ |
| | membrane fraction (GOTERM_CC_FAT) | $8.70 * 10^{-4}$ | $7.70 * 10^{-2}$ |
| | plasma liproprotein particle (GOTERM_CC_FAT) | $1.90 * 10^{-4}$ | $7.90 * 10^{-2}$ |
| | protein-lipid complex (GOTERM_CC_FAT) | $1.90 * 10^{-4}$ | $7.90 * 10^{-2}$ |
| | signal peptide (UP_SEQ_FEATURE) | $1.90 * 10^{-4}$ | $8.70 ** 10^{-2}$ |
| Down-regulated in COPD | secreted (SP_PIR_KEYWORDS) | $1.80 * 10^{-4}$ | $6.50 ** 10^{-2}$ |
| | signal (SP_PIR_KEYWORDS) | $8.40 * 10^{-4}$ | $6.80 * 10^{-2}$ |
| | differentiation (SP_PIR_KEYWORDS) | $4.60 * 10^{-4}$ | $7.40 * 10^{-2}$ |
| | egf-like domain(SP_PIR_KEYWORDS) | $1.40 * 10^{-4}$ | $7.50 * 10^{-2}$ |

Table A lists the 98 genes whose expression levels were associated with COPD status, identified by Probeset ID (col. 1), Gene Symbol (col. 2), and Entrez Gene ID (col. 3). The sequences for each gene (SEQ ID NOS: 1-98; Table A, col. 4) and the protein encoded by each gene (SEQ ID NOS: 99-195; Table A, col. 5) are presented in the Sequence Listing. (TPRXL (Entrez Gene ID 348825) is a non-coding RNA so there is no corresponding protein sequence.) The sixth column of Table A indicates whether the gene is upregulated (up) or downregulated (down) in airway epithelia of subjects with COPD.

TABLE A

| Probe ID | Gene Symbol | Entrez Gene ID | Gene Sequence Identification Number | Protein Sequence Identification Number | Direction in COPD |
|---|---|---|---|---|---|
| 10242_at | KCNMB2 | 10242 | 1 | 99 | down |
| 10321_at | CRISP3 | 10321 | 2 | 100 | down |
| 10391_at | CORO2B | 10391 | 3 | 101 | down |
| 10449_at | ACAA2 | 10449 | 4 | 102 | down |
| 10455_at | PECI | 10455 | 5 | 103 | down |
| 1048_at | CEACAM5 | 1048 | 6 | 104 | up |
| 10643_at | IGF2BP3 | 10643 | 7 | 105 | up |
| 11074_at | TRIM31 | 11074 | 8 | 106 | up |
| 11197_at | WIF1 | 11197 | 9 | 107 | down |
| 11213_at | IRAK3 | 11213 | 10 | 108 | up |
| 117156_at | SCGB3A2 | 117156 | 11 | 109 | down |
| 131450_at | CD200R1 | 131450 | 12 | 110 | up |
| 135228_at | CD109 | 135228 | 13 | 111 | up |
| 1562_at | CYP2C18 | 1562 | 14 | 112 | up |
| 158471_at | PRUNE2 | 158471 | 15 | 113 | down |
| 160728_at | SLC5A8 | 160728 | 16 | 114 | up |
| 1809_at | DPYSL3 | 1809 | 17 | 115 | up |
| 1825_at | DSC3 | 1825 | 18 | 116 | up |
| 1836_at | SLC26A2 | 1836 | 19 | 117 | up |
| 1847_at | DUSP5 | 1847 | 20 | 118 | up |
| 2037_at | EPB41L2 | 2037 | 21 | 119 | down |
| 219970_at | GLYATL2 | 219970 | 22 | 120 | up |
| 220416_at | LRRC63 | 220416 | 23 | 121 | down |
| 221395_at | GPR116 | 221395 | 24 | 122 | down |
| 23089_at | PEG10 | 23089 | 25 | 123 | down |
| 23120_at | ATP10B | 23120 | 26 | 124 | up |
| 2353_at | FOS | 2353 | 27 | 125 | up |
| 2525_at | FUT3 | 2525 | 28 | 126 | up |
| 2565_at | GABRG1 | 2565 | 29 | 127 | down |
| 2568_at | GABRP | 2568 | 30 | 128 | up |
| 2571_at | GAD1 | 2571 | 31 | 129 | up |
| 25849_at | DKFZP564O0823 | 25849 | 32 | 130 | up |
| 26154_at | ABCA12 | 26154 | 33 | 131 | up |
| 27286_at | SRPX2 | 27286 | 34 | 132 | up |
| 28234_at | SLCO1B3 | 28234 | 35 | 133 | up |

TABLE A-continued

| Probe ID | Gene Symbol | Entrez Gene ID | Gene Sequence Identification Number | Protein Sequence Identification Number | Direction in COPD |
|---|---|---|---|---|---|
| 2922_at | GRP | 2922 | 36 | 134 | down |
| 3043_at | HBB | 3043 | 37 | 135 | up |
| 3164_at | NR4A1 | 3164 | 38 | 136 | up |
| 3371_at | TNC | 3371 | 39 | 137 | up |
| 342035_at | GLDN | 342035 | 40 | 138 | down |
| 345275_at | HSD17B13 | 345275 | 41 | 139 | down |
| 348825_at | TPRXL | 348825 | 42 | | up |
| 3620_at | INDO | 3620 | 43 | 140 | up |
| 389136_at | VGLL3 | 389136 | 44 | 141 | down |
| 3934_at | LCN2 | 3934 | 45 | 142 | up |
| 400986_at | LOC400986 | 400986 | 46 | 143 | up |
| 4036_at | LRP2 | 4036 | 47 | 144 | down |
| 404220_at | C6orf201 | 404220 | 48 | 145 | down |
| 4057_at | LTF | 4057 | 49 | 146 | down |
| 4256_at | MGP | 4256 | 50 | 147 | down |
| 440603_at | BCL2L15 | 440603 | 51 | 148 | up |
| 4543_at | MTNR1A | 4543 | 52 | 149 | up |
| 4585_at | MUC4 | 4585 | 53 | 150 | up |
| 4883_at | NPR3 | 4883 | 54 | 151 | down |
| 5172_at | SLC26A4 | 5172 | 55 | 152 | up |
| 5275_at | SERPINB13 | 5275 | 56 | 153 | up |
| 5321_at | PLA2G4A | 5321 | 57 | 154 | up |
| 53842_at | CLDN22 | 53842 | 58 | 155 | down |
| 54575_at | UGT1A10 | 54575 | 59 | 156 | up |
| 55086_at | CXorf57 | 55086 | 60 | 157 | down |
| 552_at | AVPR1A | 552 | 61 | 158 | down |
| 55885_at | LMO3 | 55885 | 62 | 159 | down |
| 56169_at | GSDMC | 56169 | 63 | 160 | up |
| 56667_at | MUC13 | 56667 | 64 | 161 | up |
| 56892_at | C8orf4 | 56892 | 65 | 162 | up |
| 56938_at | ARNTL2 | 56938 | 66 | 163 | up |
| 5737_at | PTGFR | 5737 | 67 | 164 | down |
| 5743_at | PTGS2 | 5743 | 68 | 165 | up |
| 57718_at | KIAA1622 | 57718 | 69 | 166 | down |
| 60494_at | CCDC81 | 60494 | 70 | 167 | down |
| 6288_at | SAA1 | 6288 | 71 | 168 | up |
| 6289_at | SAA2 | 6289 | 72 | 169 | up |
| 629_at | CFB | 629 | 73 | 170 | up |
| 6291_at | SAA4 | 6291 | 74 | 171 | up |
| 63895_at | FAM38B | 63895 | 75 | 172 | down |
| 64759_at | TNS3 | 64759 | 76 | 173 | down |
| 653198_at | LOC653198 | 653198 | 77 | 174 | down |
| 6947_at | TCN1 | 6947 | 78 | 175 | up |
| 7092_at | TLL1 | 7092 | 79 | 176 | down |
| 729_at | C6 | 729 | 80 | 177 | down |
| 7348_at | UPK1B | 7348 | 81 | 178 | up |
| 7850_at | IL1R2 | 7850 | 82 | 179 | up |
| 79625_at | C4orf31 | 79625 | 83 | 180 | down |
| 79820_at | CATSPERB | 79820 | 84 | 181 | up |
| 80206_at | FHOD3 | 80206 | 85 | 182 | down |
| 8190_at | MIA | 8190 | 86 | 183 | up |
| 84419_at | C15orf48 | 84419 | 87 | 184 | up |
| 8471_at | IRS4 | 8471 | 88 | 185 | down |
| 84911_at | ZNF382 | 84911 | 89 | 186 | down |
| 85479_at | DNAJC5B | 85479 | 90 | 187 | down |
| 8710_at | SERPINB7 | 8710 | 91 | 188 | down |
| 8910_at | SGCE | 8910 | 92 | 189 | down |
| 9073_at | CLDN8 | 9073 | 93 | 190 | down |
| 9245_at | GCNT3 | 9245 | 94 | 191 | up |
| 9353_at | SLIT2 | 9353 | 95 | 192 | down |
| 9407_at | TMPRSS11D | 9407 | 96 | 193 | up |
| 9723_at | SEMA3E | 9723 | 97 | 194 | down |
| 9982_at | FGFBP1 | 9982 | 98 | 195 | up |

Figure 5A:
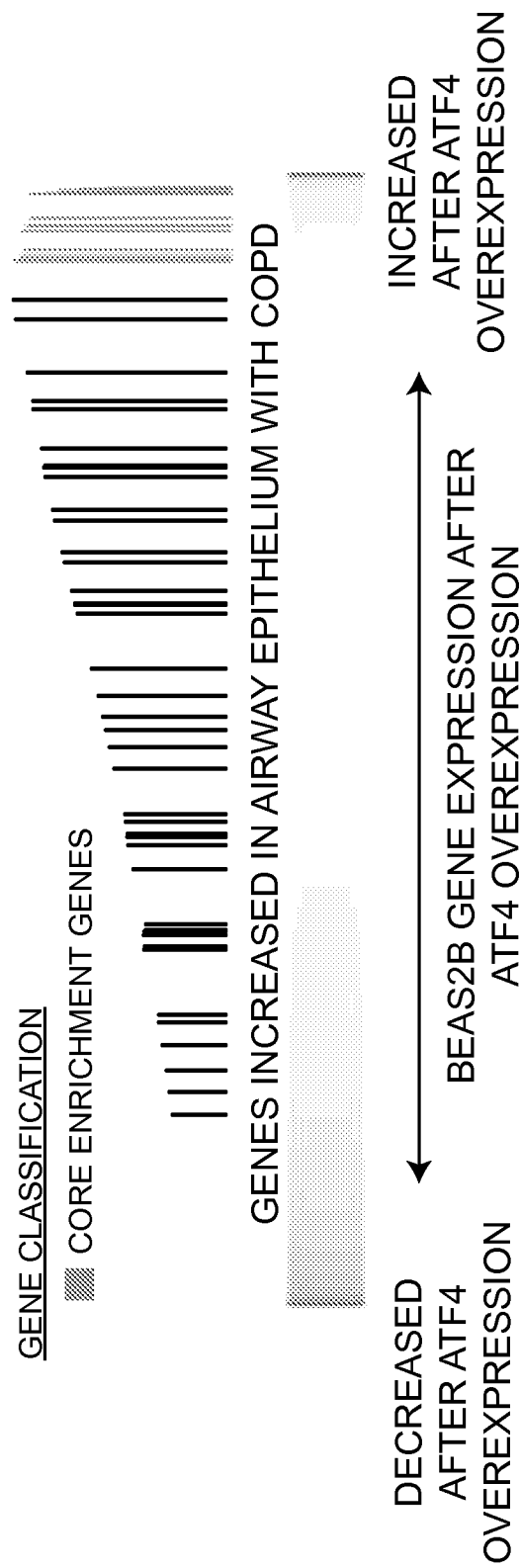
FIGS. 5A to 5C show that ATF4 overexpression in BEAS2B cells in vitro recapitulates the in vivo airway gene-expression signature of COPD. A) GSEA demonstrates enrichment of genes with increased expression in airway epithelium from individuals with COPD among genes whose expression is increased with ATF4 overexpression in BEAS2B cells (FDR<0.05). Genes are ranked from left to right based on their ATF4-associated expression pattern in vitro. The position of each vertical bar indicates the position of a gene with COPD-associated gene expression in airway epithelium within this ranked list. The height of this bar represents the running GSEA enrichment score. Core enrichment genes are highlighted in green. B) Expression levels of the core enrichment genes (green) in the bronchial brushing samples, all of which are predicted targets of ATF4 (p<0.001), are shown in this heatmap supervised by COPD status (orange: COPD; blue: Normal). C) Expression levels of the core enrichment genes (green) with ATF4 overexpression in airway epithelium in vitro (black: negative control; yellow: ATF4 overexpression).
Figure 5B:
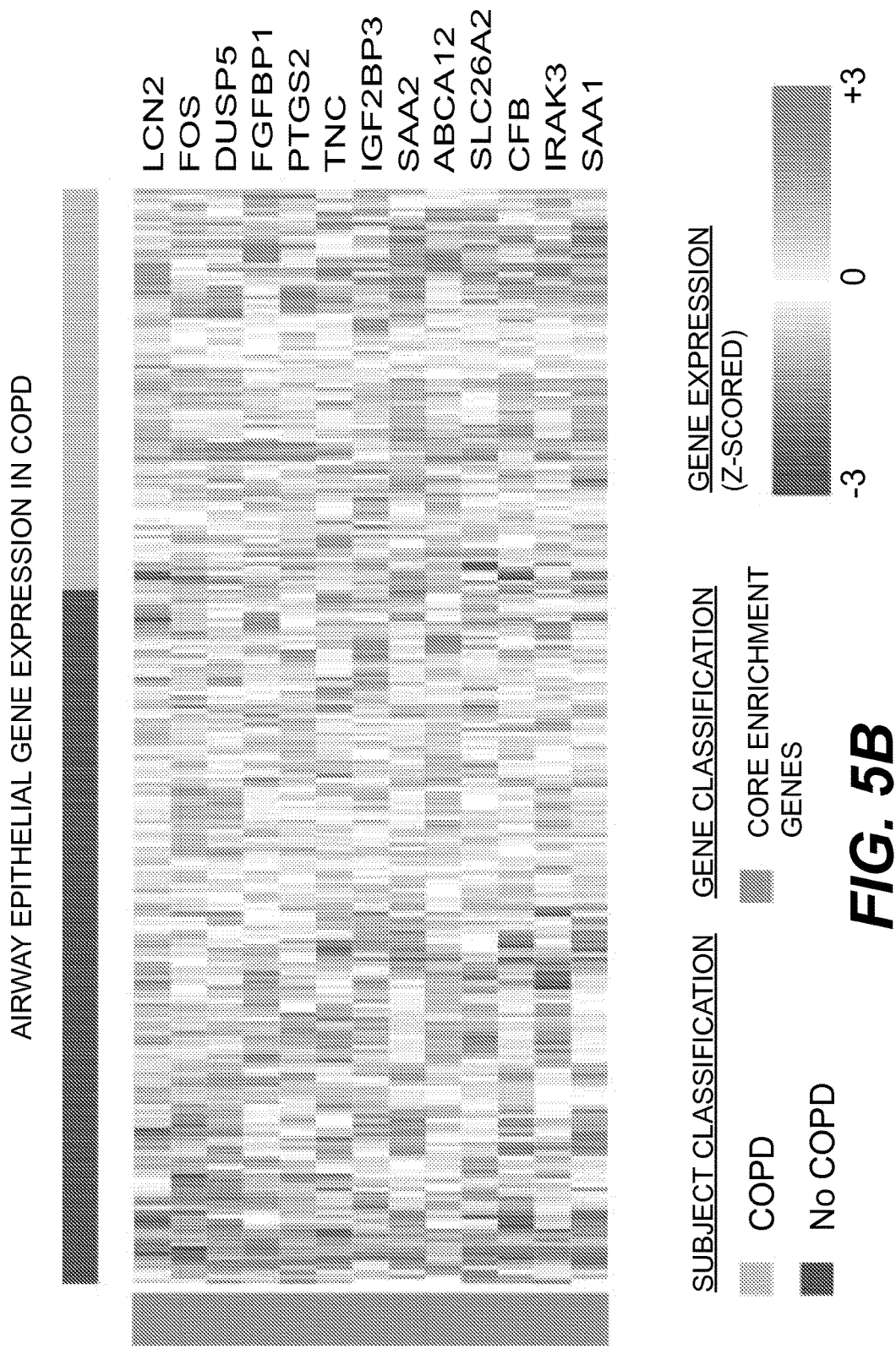
Figure 5C:
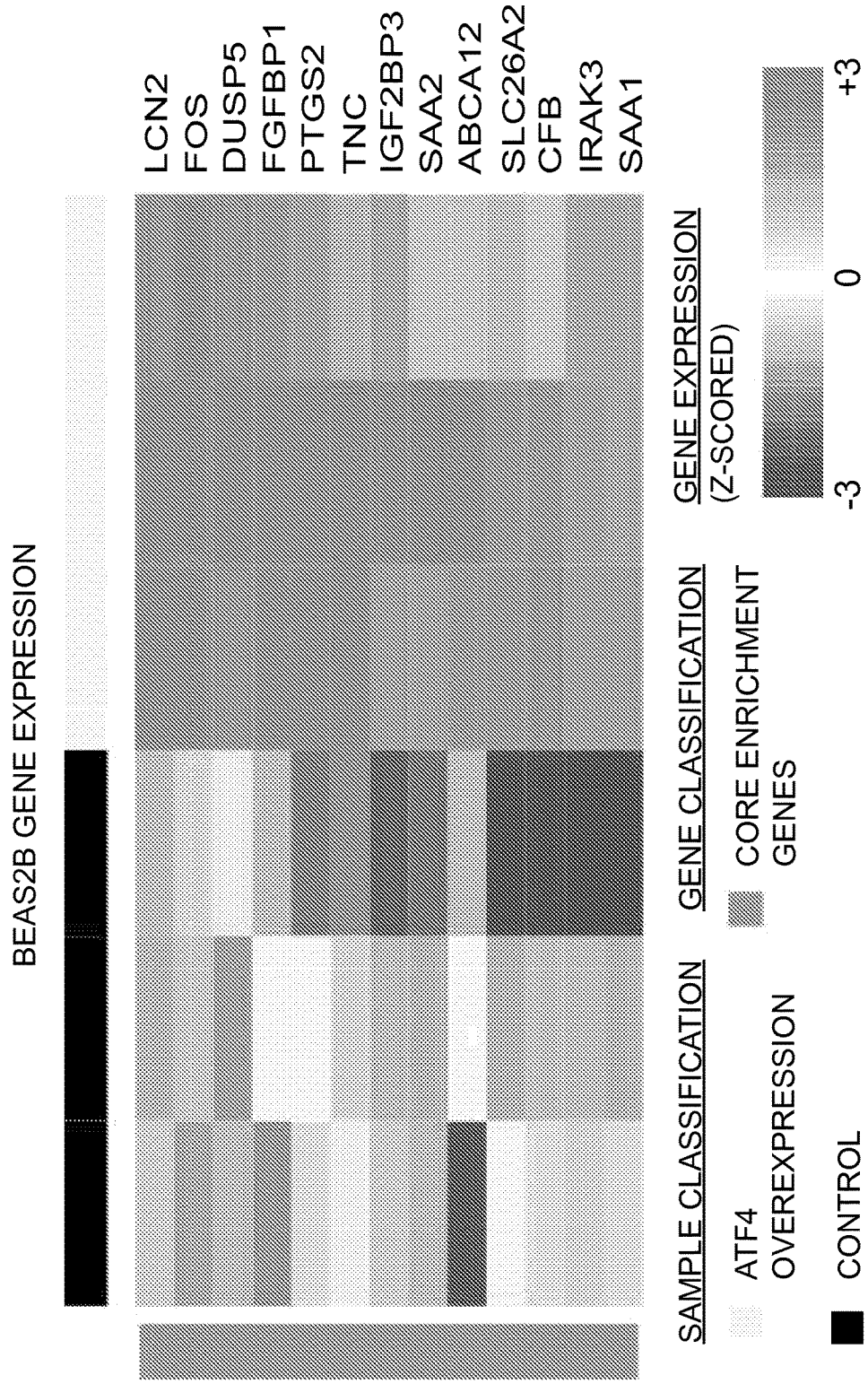
Figure 6:
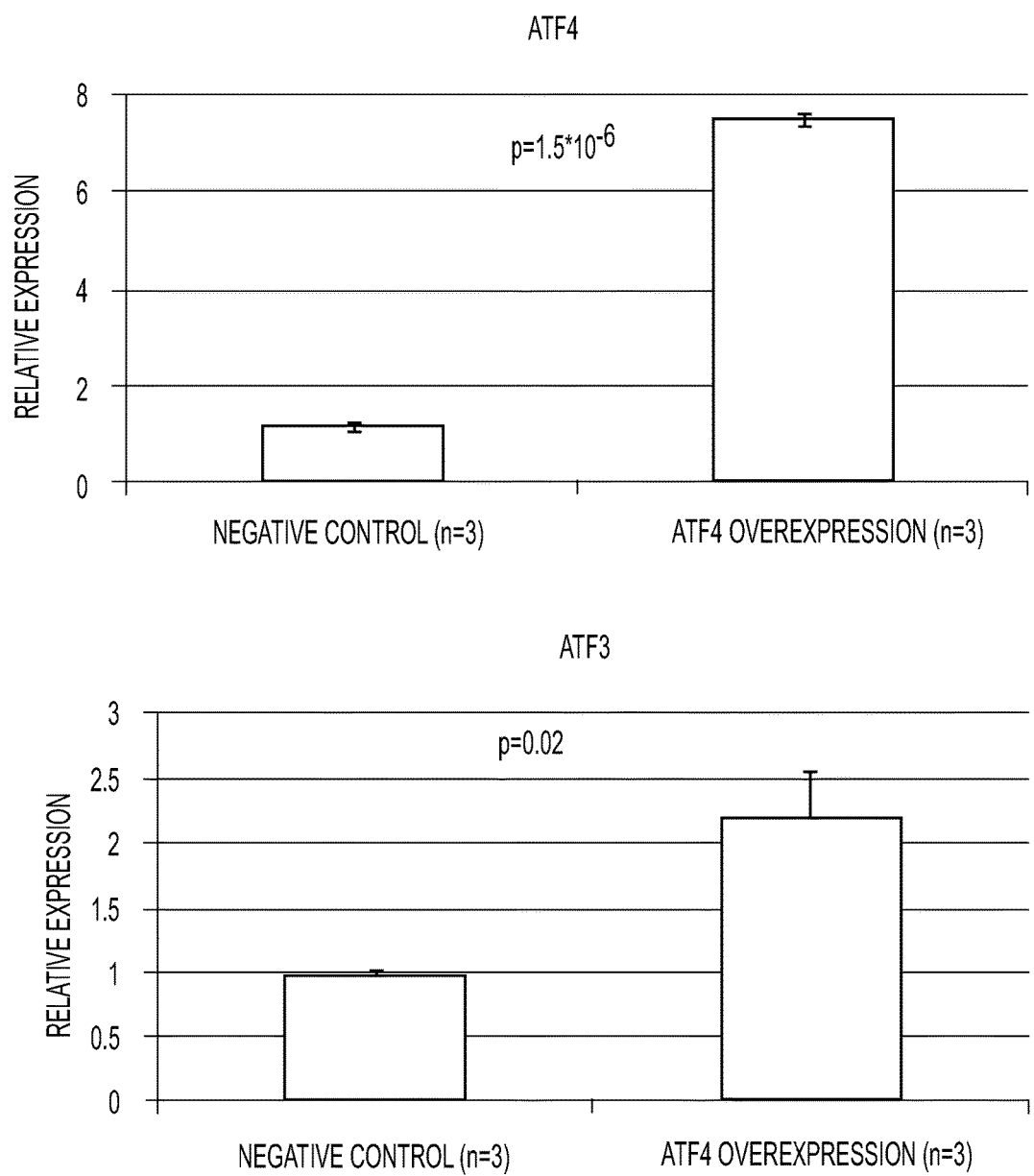

Example 3: ATF4 as a Mediator of Airway Gene-Expression Alterations Associated with COPD To explore potential regulators of COPD-associated changes in gene expression, we used GATHER to identify transcription factor binding sites enriched in the regulatory regions of differentially expressed genes. We identified enrichment of binding sites for ATF4 and CREB1 among the 98 genes with COPD-associated expression differences ($p<0.001$) (Table 6). To explore a potential mechanistic role for ATF4 in regulating COPD-associated gene expression differences, we examined the effects of overexpressing ATF4 in the BEAS2B bronchial epithelium cell line and found that this resulted in an increase in many of the same genes that are expressed at higher levels in the bronchial airway of individuals with COPD (FIG. 5A; FIG. 6). Furthermore, all 13 of the core enrichment genes increased by both ATF4 overexpression and in the airway COPD signature are predicted targets of ATF4 (FIG. 5B-C). (Matys V, et al. 2006. TRANSFAC and its module TRANSCompel: transcriptional gene regulation in eukaryotes. *Nucleic Acids Res* 34(Database issue):D108-110; Hertz G Z and Stormo G D. 1999. Identifying DNA and protein patterns with statistically significant alignments of multiple sequences. *Bioinformatics* 15:563-577.) Those 13 genes and the proteins they encode are listed in Table B. These findings suggest that over-expression of ATF4 is sufficient to recapitulate a component of the airway gene-expression differences associated with the presence of COPD in vivo, and that ATF4 might therefore be a mediator of these changes.

TABLE 6

Enrichment of transcription factor binding sites among bronchial airway gene expression changes associated with COPD.

| Transcription factor | GATHER annotation | Genes from COPD signature | P-value | Bayes Factor |
|---|---|---|---|---|
| Activating transcription factor 4 (ATF4) | V$ATF4_Q2 | FOS<br>GABRP<br>IRAK3<br>MIA<br>MTNR1A<br>NR4A1<br>PLA2G4A<br>SLIT2<br>UGT1A10<br>WIF1 | <0.001 | 6 |
| cAMP responsive binding element 1 (CREB1) | V$CREB_Q2_01 | ABCA12<br>ACAA2<br>DKFZP564O0823<br>EPB41L2<br>FOS<br>GRP<br>IRAK3<br>MIA<br>MUC13<br>NR4A1<br>PTGS2<br>SRPX2<br>UGT1A10 | <0.001 | 6 |

TABLE B

| Probe ID | Gene Symbol | Entrez Gene ID | Gene Sequence Identification Number | Protein Sequence Identification Number |
|---|---|---|---|---|
| 3934_at | LCN2 | 3934 | 45 | 142 |
| 2353_at | FOS | 2353 | 27 | 125 |
| 1847_at | DUSP5 | 1847 | 20 | 118 |
| 9982_at | FGFBP1 | 9982 | 98 | 195 |
| 5743_at | PTGS2 | 5743 | 68 | 165 |
| 3371_at | TNC | 3371 | 39 | 137 |
| 10643_at | IGF2BP3 | 10643 | 7 | 105 |
| 6289_at | SAA2 | 6289 | 72 | 169 |
| 26154_at | ABCA12 | 26154 | 33 | 131 |
| 1836_at | SLC26A2 | 1836 | 19 | 117 |
| 629_at | CFB | 629 | 73 | 170 |
| 11213_at | IRAK3 | 11213 | 10 | 108 |
| 6288_at | SAA1 | 6288 | 71 | 168 |

Figure 7:
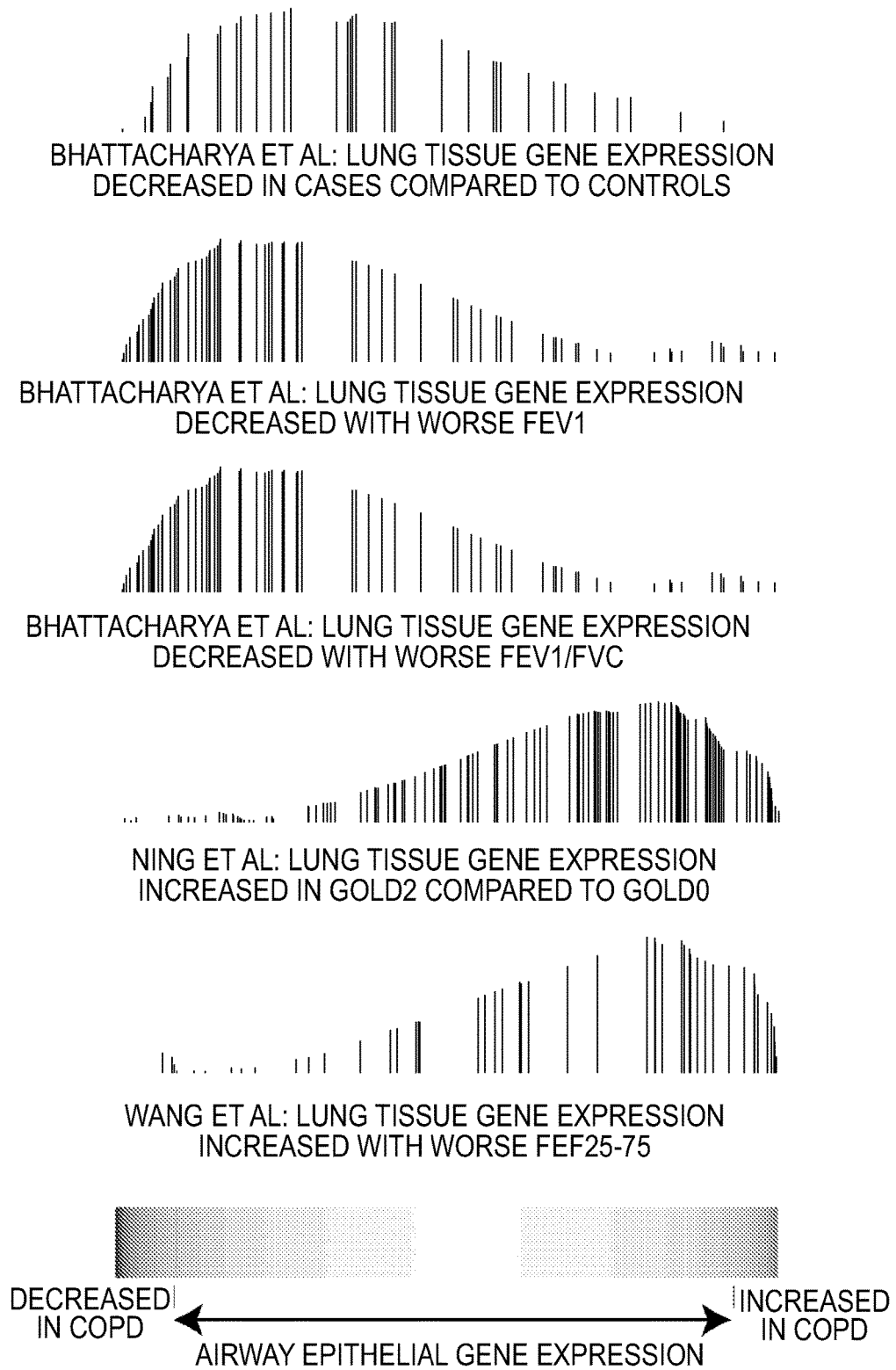

Example 4: The Relationship Between COPD-Associated Gene Expression in the Bronchial Airway Epithelium and In Lung Parenchyma We next examined whether COPD-associated gene expression changes in the bronchial airway reflect disease-associated processes in lung parenchyma. By GSEA, we found concordant enrichment of gene expression changes in bronchial airway and lung tissue in three previously published COPD datasets (FDR$_{GSEA}$<0.05) (FIG. 7). Genes whose expression levels were increased in the lung tissue of GOLD Grade 2 subjects compared to GOLD Grade 0 subjects (Ning W, et al. 2004. Comprehensive gene expression profiles reveal pathways related to the pathogenesis of chronic obstructive pulmonary disease. *Proc Natl Acad Sci USA* 101:14895-14900.) or negatively correlated with FEF$_{25-75\%}$ (Wang I M, et al. 2008. Gene Expression Profiling in Patients with Chronic Obstructive Pulmonary Disease and Lung Cancer. *Am J Respir Crit Care Med* 177:411.) were enriched among genes whose expression was increased in the bronchial airway with COPD. Similarly, genes down-regulated in the lung tissue of COPD cases compared to controls or in lung tissue from subjects with worse lung function were enriched among genes whose expression was decreased in the bronchial airway epithelium in COPD. (Bhattacharya S, et al. 2009. Molecular biomarkers for quantitative and discrete COPD phenotyes. *Am J Respir Cell Mol Biol* 40:359-367.) There were also similarities between COPD-associated airway gene expression and lung parenchymal gene expression when gene expression profiles from these previously published datasets were ranked according to the strength of association with COPD or COPD-related traits (FDR$_{GSEA}$<0.05) (FIG. 3) and interrogated with the disease-associated genes we identified in the bronchial airway. These findings demonstrate that similar changes in gene expression occur in the airway epithelium and lung tissue, suggesting that the COPD-associated airway gene expression differences mirror aspects of disease processes occurring in lung tissue. This finding validates the use of the expression of these 98 genes in airway epithelium as a merker of disease state in lung tissue.

Figure 8A:
FIGS. 8A to 8C show that airway transcriptomic alterations in COPD reflect gene-expression changes associated with emphysema severity in lung tissue. A) GSEA demonstrates enrichment of genes whose expression levels in the airway epithelium significantly increased in COPD among genes whose expression is increased with worsening emphysema severity in lung tissue (FDR<0.05). Genes are ranked from left to right based on their emphysema-associated expression pattern in lung tissue. The position of each vertical bar indicates the position of a gene whose expression in airway epithelium is associated with COPD within this ranked list. The height of this bar represents the running GSEA enrichment score. The core enrichment genes are highlighted in green. B) Expression of the core enrichment genes (green) in the bronchial brushing samples is shown in this heatmap supervised by COPD status (orange: COPD; blue: Normal). C) Expression of the core enrichment genes (green) in lung tissue samples is shown in this heatmap supervised by emphysema severity (light grey: no emphysema; black: severe emphysema).
Figure 8B:
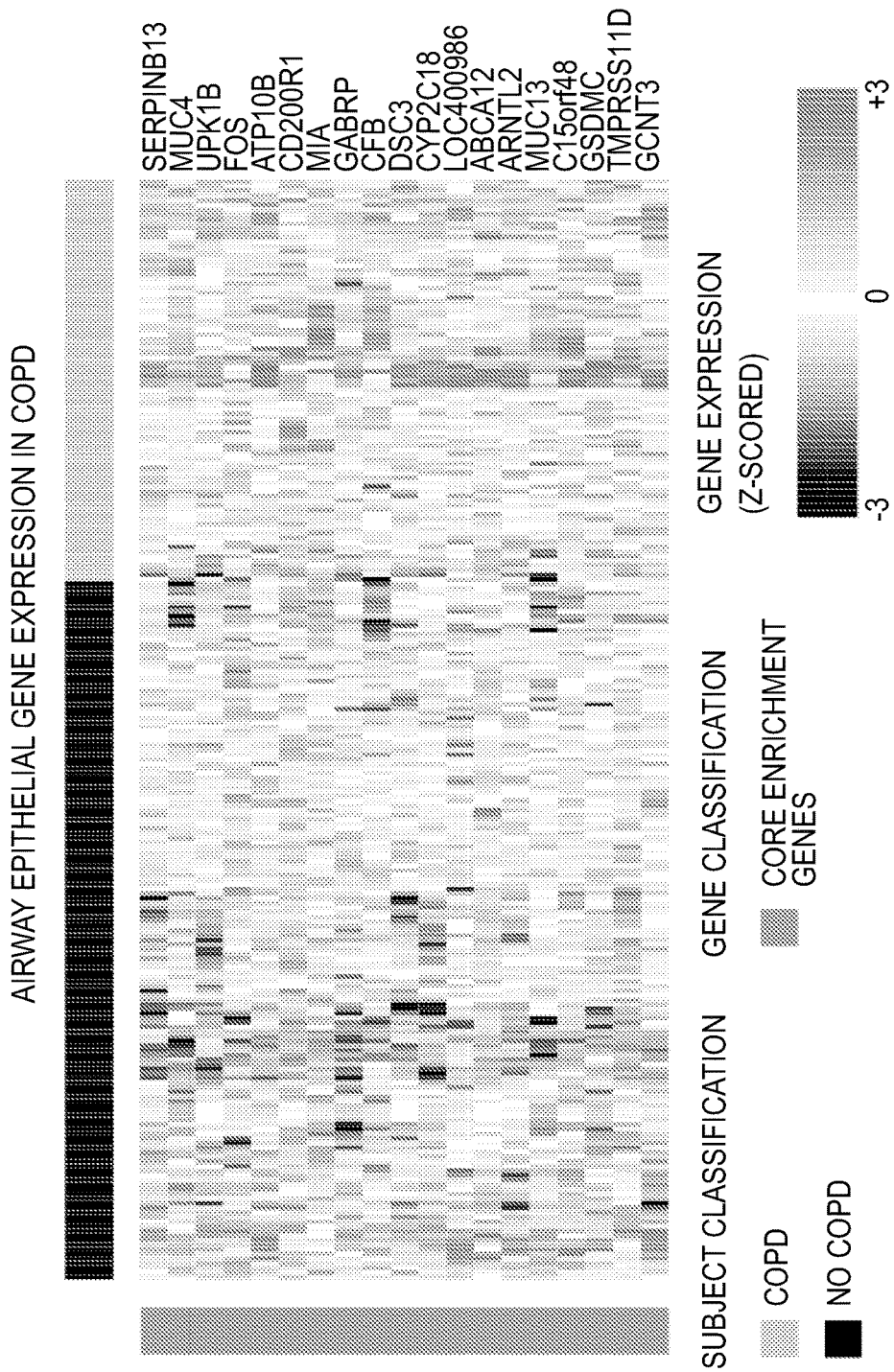
Figure 8C:
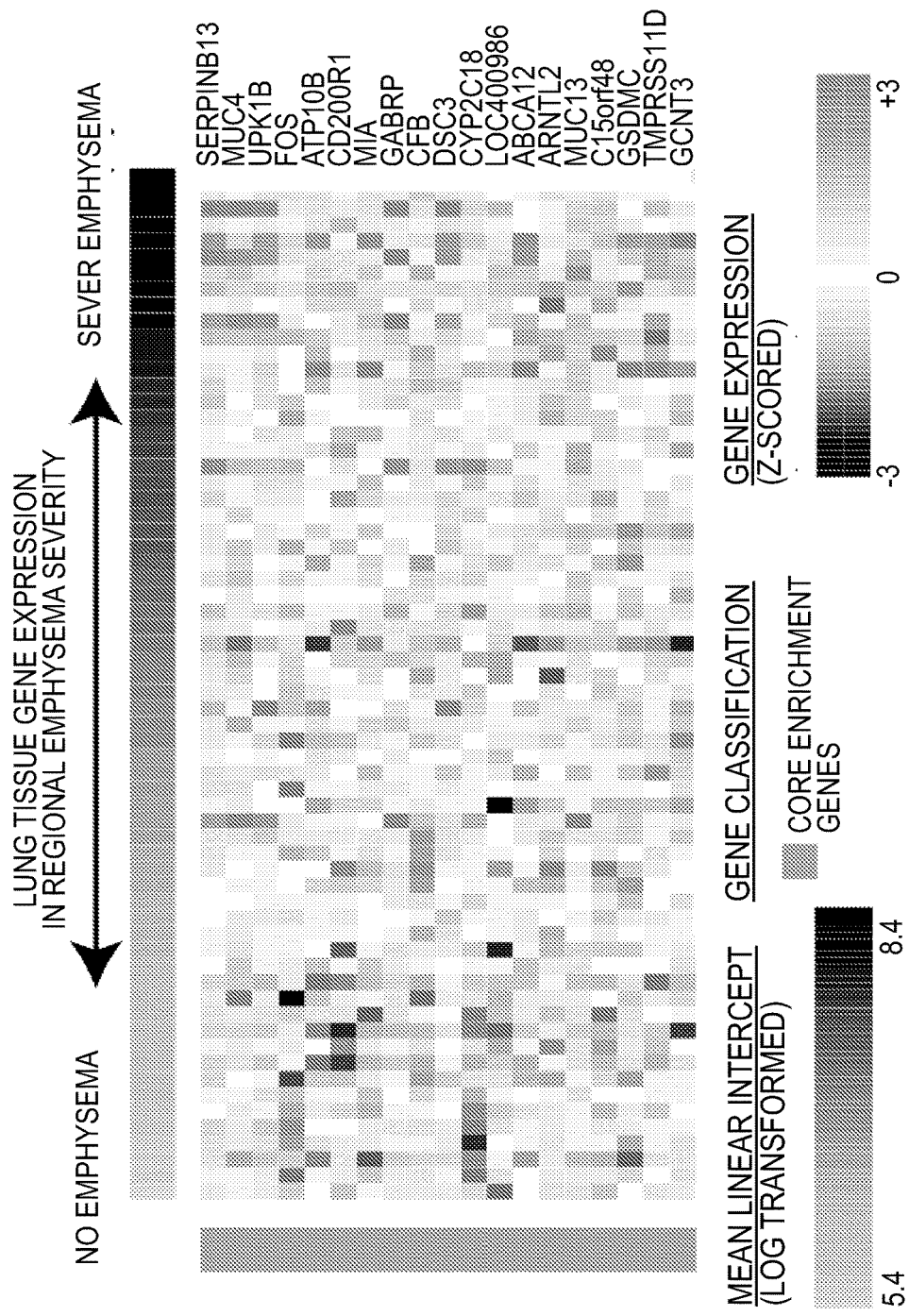

To further explore the relationship between bronchial epithelial and lung tissue gene expression related to COPD, we used GSEA to examine the distribution of the 98 genes whose expression levels were associated with COPD in a ranking of all genes according to their expression change in lung parenchyma as a function of mean linear intercept, a morphologic measure of emphysema (GSE27597). (Campbell J D, et al. 2012. A gene expression signature of emphysema-related lung destruction and its reversal by the tripeptide GHK. *Genome Med* 4:67.) Lung parenchymal genes whose expression levels increased with regional emphysema severity were enriched for bronchial epithelial genes whose expression was increased in COPD (FDR$_{GSEA}$<0.05) (FIG. 8). The genes contributing most strongly to this enrichment included SERPINB13, a serine peptidase inhibitor, and TMPRSS11D, a trypsin-like protease. The full list of identified genes and encoded proteins is presented in Table C. These findings support the biologic relevance of the bronchial epithelial gene expression signature of COPD by linking it to both clinical and pathologic measures of disease severity.

TABLE C

| Probe ID | Gene Symbol | Entrez Gene ID | Gene Sequence Identification Number | Protein Sequence Identification Number |
|---|---|---|---|---|
| 5275_at | SERPINB13 | 5275 | 56 | 153 |
| 4585_at | MUC4 | 4585 | 53 | 150 |
| 7348_at | UPK1B | 7348 | 81 | 178 |
| 2353_at | FOS | 2353 | 27 | 125 |
| 23120_at | ATP10B | 23120 | 26 | 124 |
| 131450_at | CD200R1 | 131450 | 12 | 110 |
| 8190_at | MIA | 8190 | 92 | 189 |
| 2568_at | GABRP | 2568 | 30 | 128 |
| 629_at | CFB | 629 | 73 | 170 |
| 1825_at | DSC3 | 1825 | 18 | 116 |
| 1562_at | CYP2C18 | 1562 | 14 | 112 |
| 400986_at | LOC400986 | 400986 | 46 | 143 |
| 26154_at | ABCA12 | 26154 | 33 | 131 |
| 56938_at | ARNTL2 | 56938 | 66 | 163 |
| 56667_at | MUC13 | 56667 | 64 | 161 |
| 84419_at | C15orf48 | 84419 | 87 | 184 |
| 56169_at | GSDMC | 56169 | 63 | 160 |
| 9407_at | TMPRSS11D | 9407 | 96 | 193 |
| 9245_at | GCNT3 | 9245 | 94 | 191 |

Genes (and encoded proteins) that are in common to tables B and C are listed in Table D.

TABLE D

| Probe ID | Gene Symbol | Entrez Gene ID | Gene Sequence Identification Number | Protein Sequence Identification Number |
|---|---|---|---|---|
| 26154_at | ABCA12 | 26154 | 33 | 131 |
| 629_at | CFB | 629 | 73 | 170 |
| 2353_at | FOS | 2353 | 27 | 125 |

Figure 9A:
FIGS. 9A and 9B show that gene expression changes in the airway of subjects with COPD are modulated by inhaled corticosteroids. A) Using GSEA, we identified enrichment of airway gene expression associated with COPD in an independent gene expression dataset of endobronchial biopsies obtained at 0, 6, and 30 months from individuals with COPD randomized to receive fluticasone (n=25), salmeterol and fluticasone (n=20), or placebo (n=23). Many genes increased in COPD decreased with fluticasone, and genes decreased in COPD increased with fluticasone. Genes are ranked from left to right based on their association with the time by treatment interaction effect. The position of each vertical bar indicates the position of a gene whose expression in airway epithelium is associated with COPD within this ranked list (the upper plot includes genes increased in COPD; while the lower plot includes genes decreased in COPD). The height of this bar represents the running GSEA enrichment score. B) Boxplots illustrate the expression levels of three core enrichment genes in the bronchial airway epithelium of subjects with COPD (n=87) compared to subjects without COPD (n=151) and in an independent cohort of subjects randomized to receive fluticasone-containing therapies or placebo (n=55 subjects with ≥1 time-point). The y-axis represents the z-score normalized residual matrix after adjusting for RIN, treatment, time, and patient effect.
Figure 9B:
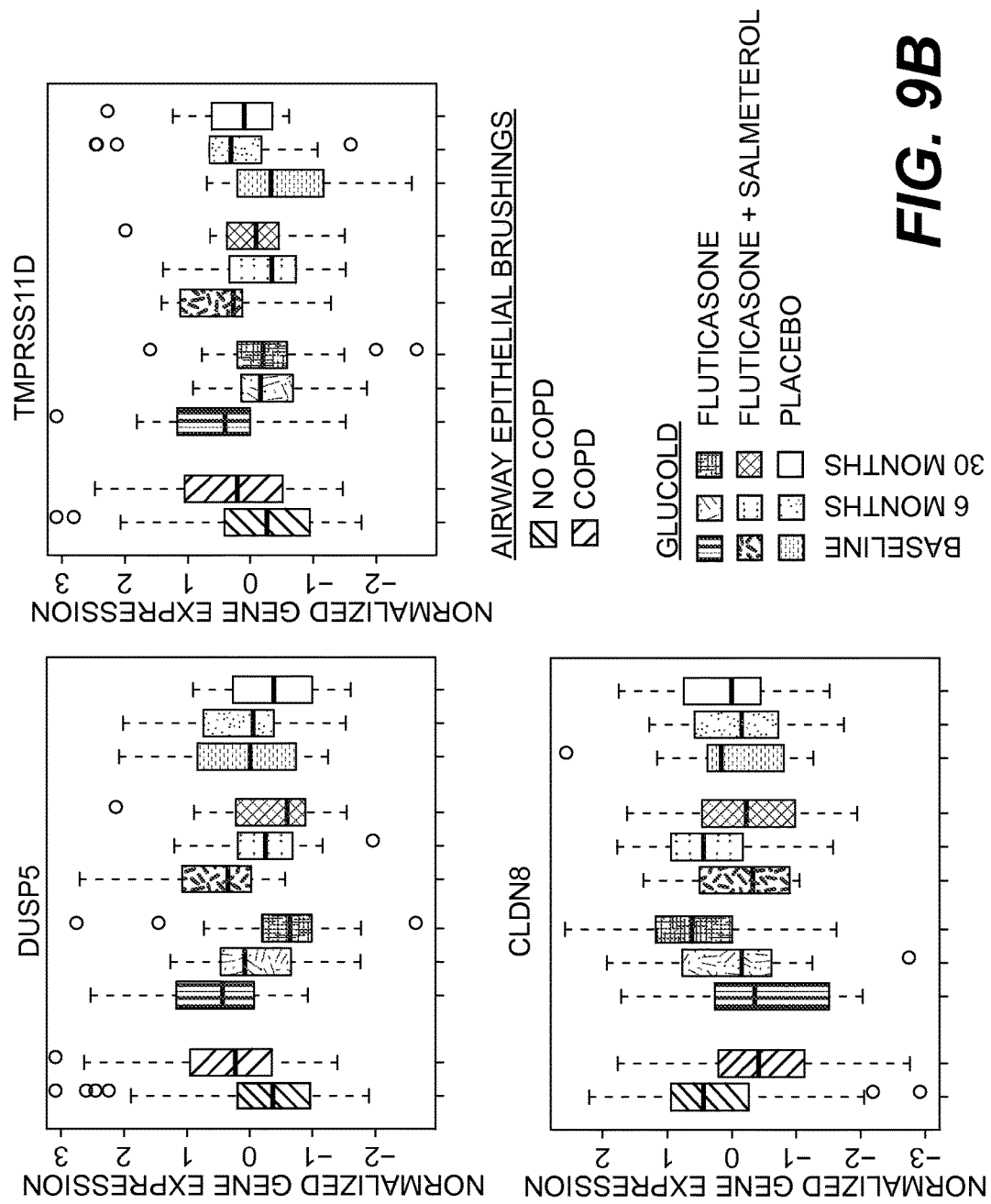

Example 5: Reversibility of COPD-Associated Changes in Airway Epithelial Gene Expression With Treatment Because inhaled corticosteroids are commonly used to treat COPD, we next sought to determine whether COPD-associated changes in airway gene expression were modifiable by fluticasone therapy in patients with COPD. We used GSEA to examine the expression of the bronchial epithelial COPD signature in a ranking of gene expression profiles derived from bronchial biopsies obtained from a subset of subjects from the GLUCOLD trial (ClinicalTrials.gov registration number: NCT00158847) (GSE36221), an independent longitudinal study of subjects with COPD randomized to fluticasone with or without salmeterol, or placebo. (Lapperre T S, et al, and Groningen Leiden Universities Corticosteroids in Obstructive Lung Disease Study Group. 2009. Effect of fluticasone with and without salmeterol on pulmonary outcomes in chronic obstructive pulmonary disease: a randomized trial. Ann Intern Med 151:517-527.) Expression levels of the 54 genes increased in the bronchial epithelial COPD signature were enriched among genes whose expression decreased following treatment containing fluticasone ($FDR_{GSEA}<0.05$, FIG. 9A). Similarly, expression levels of the 44 genes decreased with COPD in the bronchial airway signature were enriched among genes whose expression levels increased following treatment with fluticasone in the GLUCOLD cohort ($FDR_{GSEA}<0.05$, FIG. 9A). The genes contributing most strongly to the this enrichment included DUSP5, a key regulator of cell proliferation and differentiation, TMPRSS11D, which serves a key role in host defense in the airway, and CLDN8, which functions in tight junctions between epithelial cells (FIG. 9B). These results suggest that a subset of airway gene expression changes associated with COPD can be reversed by inhaled corticosteroids.

The genes contributing most strongly to significant GSEA enrichment of the 98-gene COPD signature among the GLUCOLD dataset ("core enrichment genes") are listed in Table E.

TABLE E

| Probe ID | Gene Symbol | Entrez Gene ID | Gene Sequence Identification Number | Protein Sequence Identification Number |
|---|---|---|---|---|
| 56667_at | MUC13 | 56667 | 64 | 161 |
| 1847_at | DUSP5 | 1847 | 20 | 118 |
| 5172_at | SLC26A4 | 5172 | 55 | 152 |
| 56938_at | ARNTL2 | 56938 | 66 | 163 |
| 4585_at | MUC4 | 4585 | 53 | 150 |
| 131450_at | CD200R1 | 131450 | 12 | 110 |
| 1048_at | CEACAM5 | 1048 | 6 | 104 |
| 135228_at | CD109 | 135228 | 13 | 111 |
| 5743_at | PTGS2 | 5743 | 68 | 165 |
| 7348_at | UPK1B | 7348 | 81 | 178 |
| 3371_at | TNC | 3371 | 39 | 137 |
| 440603_at | BCL2L15 | 440603 | 51 | 148 |
| 1825_at | DSC3 | 1825 | 18 | 116 |
| 54575_at | UGT1A10 | 54575 | 59 | 156 |
| 56169_at | GSDMC | 56169 | 63 | 160 |
| 2571_at | GAD1 | 2571 | 31 | 129 |
| 1562_at | CYP2C18 | 1562 | 14 | 112 |
| 4543_at | MTNR1A | 4543 | 52 | 149 |
| 23120_at | ATP10B | 23120 | 26 | 124 |
| 10643_at | IGF2BP3 | 10643 | 7 | 105 |
| 5275_at | SERPINB13 | 5275 | 56 | 153 |
| 27286_at | SRPX2 | 27286 | 34 | 132 |
| 7850_at | IL1R2 | 7850 | 82 | 179 |
| 26154_at | ABCA12 | 26154 | 33 | 131 |
| 2568_at | GABRP | 2568 | 30 | 128 |
| 9407_at | TMPRSS11D | 9407 | 96 | 193 |
| 117156_at | SCGB3A2 | 117156 | 11 | 109 |
| 552_at | AVPR1A | 552 | 61 | 158 |
| 389136_at | VGLL3 | 389136 | 44 | 141 |
| 4256_at | MGP | 4256 | 50 | 147 |
| 8910_at | SGCE | 8910 | 92 | 189 |
| 10455_at | PECI | 10455 | 5 | 103 |
| 23089_at | PEG10 | 23089 | 25 | 123 |
| 404220_at | C6orf201 | 404220 | 48 | 145 |
| 10391_at | CORO2B | 10391 | 3 | 101 |
| 9353_at | SLIT2 | 9353 | 95 | 192 |
| 79625_at | C4orf31 | 79625 | 83 | 180 |
| 80206_at | FHOD3 | 80206 | 85 | 182 |
| 10449_at | ACAA2 | 10449 | 4 | 102 |
| 2565_at | GABRG1 | 2565 | 29 | 127 |
| 2037_at | EPB41L2 | 2037 | 21 | 119 |
| 221395_at | GPR116 | 221395 | 24 | 122 |
| 4883_at | NPR3 | 4883 | 54 | 151 |
| 9723_at | SEMA3E | 9723 | 97 | 194 |
| 158471_at | PRUNE2 | 158471 | 15 | 113 |
| 8471_at | IRS4 | 8471 | 88 | 185 |
| 64759_at | TNS3 | 64759 | 76 | 173 |
| 9073_at | CLDN8 | 9073 | 93 | 190 |
| 7092_at | TLL1 | 7092 | 79 | 176 |
| 342035_at | GLDN | 342035 | 40 | 138 |
| 10321_at | CRISP3 | 10321 | 2 | 100 |
| 5737_at | PTGFR | 5737 | 67 | 164 |

Figure 10:
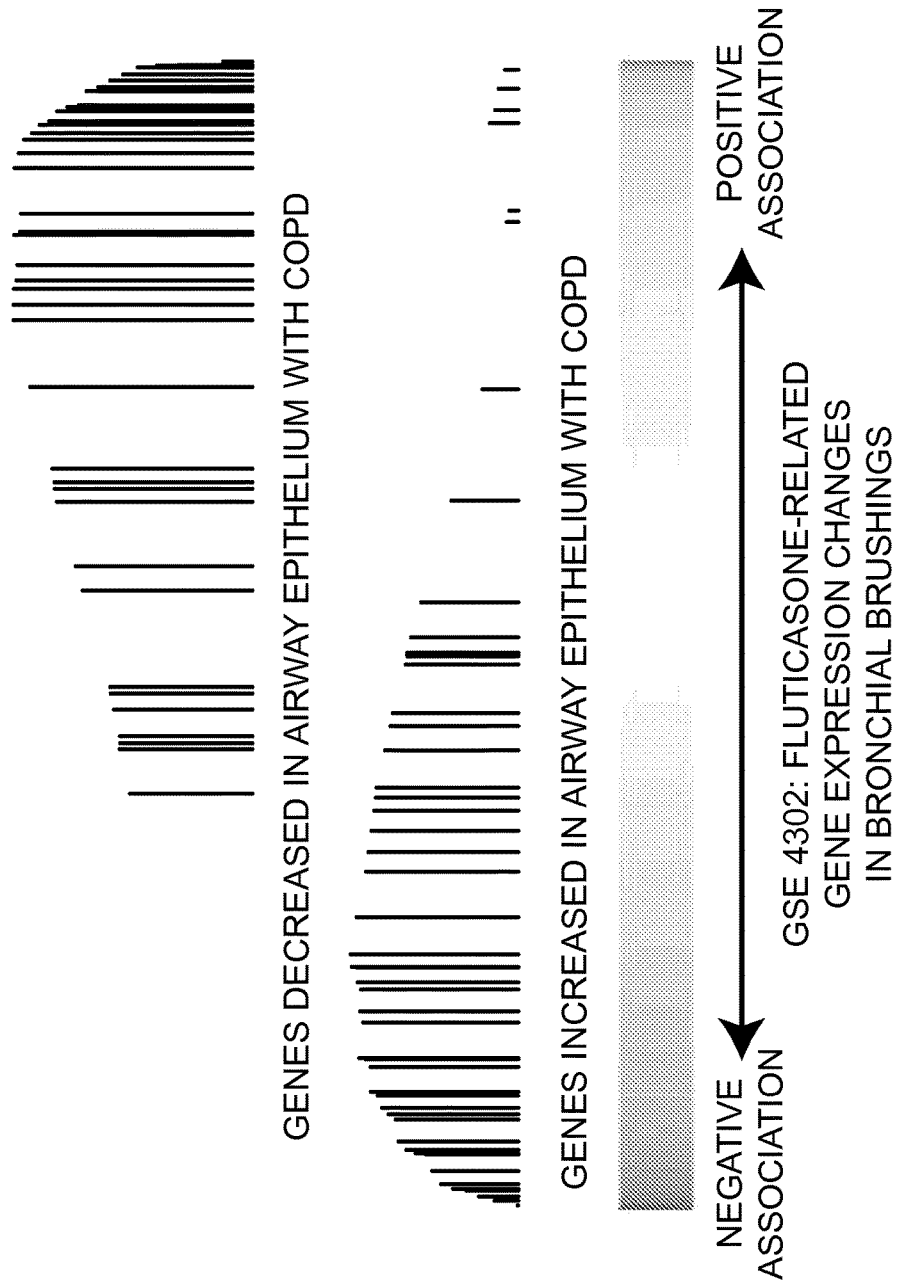
FIG. 10 shows modulation of the bronchial airway gene expression signature of COPD by fluticasone. Fluticasone-associated changes in bronchial airway epithelial gene expression was compared to the bronchial airway COPD signature. Genes are ranked from left to right based on their association with the time and treatment interaction effect, and the color bar indicates the strength of this association. Each vertical bar indicates the position of a gene from the COPD airway gene expression signature within the ranked list, and the height of this bar represents the running GSEA enrichment score. These findings demonstrate that the airway COPD signature can be modulated by fluticasone (FDR<0.05).

To validate our findings in the GLUCOLD cohort, we examined the relationship between the airway gene expression signature of COPD and fluticasone-related gene expression differences from an independent dataset in which gene expression in bronchial epithelium samples from before and after fluticasone treatment was profiled using microarrays. (Woodruff P G, et al. 2007. Genome-wide profiling identifies epithelial cell genes associated with asthma and with treatment response to corticosteroids. *Proc Natl Acad Sci USA* 104:15858-15863.) Using a linear mixed effects model, genes were ranked according to their change with fluticasone over time. Using GSEA, we found that the 54 genes up-regulated in the airway COPD signature were enriched among the genes decreased by fluticasone treatment and that the 44 genes down-regulated in the airway COPD signature were enriched among the genes increased by fluticasone treatment (FDR$_{GSEA}$<0.05, FIG. 10). This finding suggests that fluticasone reverts genes that are altered in the airways of patients with COPD. Taken together with our observations in the GLUCOLD cohort, these data suggest that COPD-associated gene expression patterns are potentially dynamic with therapy.

Table F lists genes (and corresponding proteins) in commone between Tables B and E.

TABLE F

| Probe ID | Gene Symbol | Entrez Gene ID | Gene Sequence Identification Number | Protein Sequence Identification Number |
|---|---|---|---|---|
| 26154_at | ABCA12 | 26154 | 33 | 131 |
| 1847_at | DUSP5 | 1847 | 20 | 118 |
| 10643_at | IGF2BP3 | 10643 | 7 | 105 |
| 5743_at | PTGS2 | 5743 | 68 | 165 |
| 1836_at | SLC26A2 | 1836 | 19 | 117 |
| 3371_at | TNC | 3371 | 39 | 137 |

Table G lists genes (and corresponding proteins) in common between Tables C and E.

TABLE G

| Probe ID | Gene Symbol | Entrez Gene ID | Gene Sequence Identification Number | Protein Sequence Identification Number |
|---|---|---|---|---|
| 26154_at | ABCA12 | 26154 | 33 | 131 |
| 56938_at | ARNTL2 | 56938 | 66 | 163 |
| 23120_at | ATP10B | 23120 | 26 | 124 |
| 131450_at | CD200R1 | 131450 | 12 | 110 |
| 1562_at | CYP2C18 | 1562 | 14 | 112 |
| 1825_at | DSC3 | 1825 | 18 | 116 |
| 2568_at | GABRP | 2568 | 30 | 128 |
| 56169_at | GSDMC | 56169 | 63 | 160 |
| 56667_at | MUC13 | 56667 | 64 | 161 |
| 4585_at | MUC4 | 4585 | 53 | 150 |
| 5275_at | SERPINB13 | 5275 | 56 | 153 |
| 9407_at | TMPRSS11D | 9407 | 96 | 193 |
| 7348_at | UPK1B | 7348 | 81 | 178 |

DISCUSSION

By performing whole genome gene-expression profiling of bronchial brushings in a study of individuals with and without COPD, we have identified a COPD-related bronchial airway field of injury that is defined by gene expression alterations and has several important characteristics. Firstly, the gene-expression alterations in this field of injury are associated both with COPD and continuous COPD-related measures of lung function. Secondly, the COPD-associated gene expression field of injury measured in the bronchial airway epithelium is similar to COPD-associated gene-expression differences occurring in lung parenchyma. Thirdly, the COPD-associated gene expression field of injury is modifiable with treatment.

We have validated the COPD-associated airway-epithelium gene expression differences we identified, by comparison to a number of previously published studies including one study of small-airway gene expression (Tilley A E, et al. 2009. Down-regulation of the Notch pathway in human airway epithelium in association with smoking and chronic obstructive pulmonary disease. *Am J Respir Crit Care Med* 179:457-466.), and six studies of lung parenchyma. (Spira A, et al. 2004. Gene Expression Profiling of Human Lung Tissue from Smokers with Severe Emphysema. *Am J Respir Cell Mol Biol* 31:601-610; Golpon H A, et al. 2004. Emphysema Lung Tissue Gene Expression Profiling. *Am J Respir Cell Mol Biol* 31:595-600; Ning W, et al. 2004. Comprehensive gene expression profiles reveal pathways related to the pathogenesis of chronic obstructive pulmonary disease. *Proc Natl Acad Sci USA* 101:14895-14900; Bhattacharya S, et al. 2009. Molecular biomarkers for quantitative and discrete COPD phenotyes. *Am J Respir Cell Mol Biol* 40:359-367; Wang I M, et al. 2008. Gene Expression Profiling in Patients with Chronic Obstructive Pulmonary Disease and Lung Cancer. *Am J Respir Crit Care Med* 177:411; Campbell J D, et al. 2012. A gene expression signature of emphysema-related lung destruction and its reversal by the tripeptide GHK. *Genome Med* 4:67.) These observations suggest a reliable COPD-associated pattern of gene expression in the bronchial airway that is similar to distal COPD-associated gene expression differences. While the COPD-associated gene expression similarities between the bronchial airway and whole lung tissue could be due to similarities between the bronchial airway and either the lung parenchyma and/or the terminal bronchioles, our data suggest that the accessible bronchial airways reflect disease-associated processes occurring deep in the lung. Importantly, many of the previous studies of COPD-associated gene expression have involved lung tissue that is adjacent to lung cancer. In this study, by leveraging bronchoscopy samples from a lung-cancer screening cohort where the prevalence of cancer is low, we were able to profile samples exclusively from a large number of patients without lung cancer. Taken together, these findings demonstrate that the bronchial airway can serve as a readily accessible biospecimen to measure COPD-related processes in both research and clinical settings, thus enabling the systems, methods, and other aspects of the inventions of this disclosure.

The two major sites of COPD-associated pathology are the alveolae and the terminal bronchioles. We measured gene expression in much more proximal airways. If the major site of disease is more distal in the lung, there is no reason that gene expression should be altered at sites removed from the sites of pathology. The existence of an airway field of injury in COPD is an unexpected and exciting finding. Until this study, the airway field of injury concept has been described in several malignant diseases (initially oral cancer in the 1950s, subsequently lung cancer, and also some non-pulmonary cancers like breast cancer). However, this is the first study to demonstrate an airway field of injury (gene expression in the airway epithelium involved in disease that is similar to gene expression changes in distal diseased lung tissue) in a non-malignant lung disease.

The specific genes within the COPD airway epithelial gene expression signature support the biologic plausibility of this signature. For example, TMPRSS11D, also called human airway trypsin-like protease, localizes to ciliated bronchial epithelial cells and was first isolated from the sputum of patients with chronic airway diseases. (Takahashi M, et al. 2001. Localization of human airway trypsin-like protease in the airway: an immunohistochemical study.

*Histochem Cell Biol* 115:181-187.) The increased levels of TMPRSS11D gene expression in the airway epithelium of individuals with COPD are consistent with the hypothesis that this protein plays a key role in the biologic defense against inhaled substances (Takahashi M, et al. 2001. Localization of human airway trypsin-like protease in the airway: an immunohistochemical study. *Histochem Cell Biol* 115: 181-187.) SERPINB13 is a serine peptidase inhibitor increased in both airway and lung parenchyma in association with COPD. Our finding that both TMPRSS11D and SERPINB13 are increased in the airway of patients with COPD and our finding that these genes are decreased with fluticasone suggests the protease/anti-protease imbalance that is thought to play a key role in COPD pathogenesis is also reflected in airway epithelial cells, and that restoration of this balance could be useful for monitoring response to COPD therapies such as inhaled corticosteroids. Prostaglandin-endoperoxidase synthase 2 (PTGS2), is a pro-inflammatory mediator increased in the bronchial airway of individuals with COPD and is a potential target for novel anti-inflammatory therapies. Claudin 8 (CLDN8) is a member of the claudin family, which plays a key role in tight junctions and paracellular permeability. (Lal-Nag M and Morin P J. 2009. The claudins. *Genome Biol* 10:235.) Our finding that CLDN8 is decreased in the airway epithelium of subjects with COPD and increased after treatment with fluticasone suggests a potentially reversible impairment in the airway epithelium's critical barrier function (Heijink I H, et al. 2010. Characterization of cell adhesion in airway epithelial cell types using electric cell-substrate impedance sensing. *Eur Respir J* 35:894-903), and this finding is consistent with the previously observed down-regulation of claudins and other tight junction genes in bronchial epithelial cells from smokers with COPD. (Shaykhiev R, et al. 2011. Cigarette smoking reprograms apical junctional complex molecular architecture in the human airway epithelium in vivo. *Cell Mol Life Sci* 68:877-892; Soini Y. 2011. Claudins in lung diseases. *Respir Res* 12:70.)

Our observations about the potential role of ATF4 in mediating COPD-associated gene expression differences in bronchial epithelium is intriguing given the role of ATF4 in mediating the unfolded protein response. (Wek R C and Cavener D R. 2007. Translational control and the unfolded protein response. *Antioxid Redox Signal* 9:2357-2371; Rzymski T, Milani M, Singleton D C, and Harris A L. 2009. Role of ATF4 in regulation of autophagy and resistance to drugs and hypoxia. *Cell Cycle* 8:3838-3847.) ER stress from acute cigarette smoke exposure leads to an unfolded protein response which is proposed to play a role in the development of COPD. (Kelsen S G, et al. 2008. Cigarette smoke induces an unfolded protein response in the human lung: a proteomic approach. *Am J Respir Cell Mol Biol* 38:541-550; Geraghty P, et al. 2011. Induction of the unfolded protein response by cigarette smoke is primarily an activating transcription factor 4-C/EBP homologous protein mediated process. *International Journal of COPD* 6:309-319.) An increase in ER stress markers has been described in the lungs of patients with COPD. (Malhotra D, et al. 2009. Heightened endoplasmic reticulum stress in the lungs of patients with chronic obstructive pulmonary disease: the role of Nrf2-regulated protesasomal activity. *Am J Respir Crit Care Med* 180:1196-1207), and administration of acrolein, an aldehyde in cigarette smoke, leads to an increase in ER stress markers and airspace enlargement in mice, suggesting that ER stress and the unfolded protein response play key roles in the development of emphysema. (Kitaguchi Y, et al. Acrolein induces endoplasmic reticulum stress and causes airspace enlargement. *PLoS ONE* 7:e38038.) This is the first study to our knowledge to identify ATF4-driven gene expression differences in individuals with COPD. We have validated predicted targets of ATF4 in the airway COPD signature, and have further demonstrated significant enrichment of genes increased in the airway COPD signature among genes increased by ATF4. While we identified this potential regulatory relationship in airway epithelium, further studies will be necessary to examine the extent of this response in lung tissue and its importance for disease development.

The potential clinical relevance of the COPD-associated field of injury is supported by its reversal with inhaled corticosteroids in the GLUCOLD cohort. (Lapperre T S, et al, and Groningen Leiden Universities Corticosteroids in Obstructive Lung Disease Study Group. 2009. Effect of fluticasone with and without salmeterol on pulmonary outcomes in chronic obstructive pulmonary disease: a randomized trial. *Ann Intern Med* 151:517-527.) This aspect of the airway signature of COPD indicates that the constituent gene expression differences reflect more than differences due to demographic or smoking-related factors, but rather an aspect of the disease process that is modifiable with therapy. Moreover, further studies should be conducted to determine whether heterogeneity in the extent to which the airway signature of COPD is reversed by therapy is associated with differences in the clinical benefit obtained by patients. Similarly, it will be important to determine whether gene-expression heterogeneity among patients with COPD reflects underlying biological differences that can be used to develop markers that predict aspects of the clinical heterogeneity of COPD such as therapeutic response or rate of lung function decline.

As with other distal lung diseases, there are a number of potential mechanisms that might account for the similarity between lung tissue and bronchial airway gene expression. (Steiling K, et al. 2008. The field of tissue injury in the lung and airway. *Cancer Prev Res* 1:396-403.) The COPD-associated transcriptomic alterations may reflect, in part, specific physiologic responses to the toxins in cigarette smoke that in turn contribute to COPD pathogenesis. The relationship between the airway signature of COPD and gene expression differences associated with regional emphysema severity within an individual, as well as the reversal of the signature following therapy, suggest that the etiology of the COPD-associated gene expression differences is not solely due to an individual's physiologic response to tobacco smoke.

Other potential mechanisms for the airway field of injury are related to cell-cell communication. For example, inflammatory cells recruited into the airway and lungs of smokers with COPD and the cytokines they produce may induce gene-expression alterations throughout the airway epithelium. This hypothesis is consistent with our finding of specific inflammatory-related pathways enriched among the genes in our signature (FIG. 2; Table 4). However, in silico analysis of white blood cell-specific gene-expression in these samples did not reveal significant proportions of inflammatory cells nor differences in the proportion of inflammatory cells in smokers with and without COPD, and thus we do not believe that our signature directly reflects changing numbers of inflammatory cells within our airway brushings in individuals with COPD. Nonetheless, infiltration of the airway wall with inflammatory cells in smokers with COPD (Lapperre T S, et al, and Groningen Leiden Universities Corticosteroids in Obstructive Lung Disease Study Group. 2009. Effect of fluticasone with and without salmeterol on pulmonary outcomes in chronic obstructive pulmonary disease: a randomized trial. *Ann Intern Med* 151:517-527) could produce changes in the adjacent epithelial layer lining that airway.

Through analysis of the largest cohort of bronchial airway gene expression in COPD, we have identified a COPD-associated airway field of injury despite a number of potentially important limitations to our study design. Due to the nature of this lung cancer screening cohort, characterization of COPD-related phenotypes was limited, and we defined COPD as airflow obstruction on pre-bronchodilator spirometry. However, the similarity with previously published lung tissue gene expression datasets demonstrates that these COPD-associated changes in bronchial airway gene expression are reproducible and reflective of disease activity. While spirometry remains the standard for diagnosing COPD (Global initiative for chronic obstructive lung disease. 2011. Global initiative for chronic obstructive lung disease: Global strategy for the diagnosis, management, and prevention of chronic obstructive pulmonary disease.), the association of airway gene expression with subphenotypes of COPD was not evaluated including quantitative imaging of airway remodeling and emphysema, gas transfer capacity, chronic bronchitis, previous respiratory illness, frequency of exacerbations and/or quality of life metrics. Given the clinical heterogeneity among smokers with COPD, it is possible that different clinical subphenotypes of disease will impact airway gene expression differently and might contribute to the heterogeneity seen in the gene-expression signature. Furthermore, given that we were leveraging a bronchoscopy-based cohort for this study in which the majority of subjects with COPD had mild to moderate disease, it is unclear if our findings will generalize to smokers with later stage disease or if there are alterations specific to more severe disease. However, the enrichment of our airway gene expression signature among genes that change with regional emphysema severity in the lungs of smokers with severe COPD suggests that our gene expression signature is also relevant in more severe disease. Finally, while fluticasone-containing therapy has not been consistently linked with a clinical benefit, the decrease in the COPD airway gene expression signature following fluticasone therapy in two independent cohorts suggests that the COPD-associated airway field of injury is not a static consequence of disease but rather is dynamic.

In summary, we have shown that COPD induces a field of injury that extends from the lung parenchyma into the bronchial airway, and that some of the COPD-associated alterations in airway gene expression may be mediated by ATF4. We have also shown that a subset of these COPD-associated airway gene expression changes is reversed by fluticasone in a COPD cohort where that treatment resulted in improvement in lung function. These data demonstrate that gene expression profiling of the airway epithelium, which can be sampled via bronchoscopy, serves as a surrogate biomarker of disease activity. These findings suggest that this field of injury in COPD extends to epithelial cells that can be more readily sampled from the nose. (Zhang X, et al. 2010. Similarities and differences between smoking-related gene expression in the nasal and bronchial epithelium. *Physiol Genomics* 41:1-8.).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09677138B2). An electronic copy of the "Sequence Listing" will also be available from the USPTO upon request and payment of the fee set forth in 37 CFR 1.19(b)(3).

The invention claimed is:

1. A method of detecting respiratory tract epithelium gene expression, comprising:
    (a) obtaining a respiratory tract epithelium sample from a human subject; and
    (b) detecting expression in the sample of each gene of a gene set, wherein the gene set consists of DUSP5 and at least one gene selected from LCN2, FOS, FGFBP1, PTGS2, TNC, IGF2BP3, SAA2, ABCA12, SLC26A2, CFB, IRAK3, and SAA1.

2. The method of claim 1, wherein the gene set consists of LCN2, FOS, DUSP5, FGFBP1, PTGS2, TNC, IGF2BP3, SAA2, ABCA12, SLC26A2, CFB, IRAK3, and SAA1.

3. The method of claim 1, further comprising determining the expression level of each gene in the gene set, wherein an increased linear fold change of greater than 1.25 in the expression level of each gene in the gene set relative to the expression level of each gene in the gene set in a control sample is detected.

4. The method of claim 3, wherein the subject has chronic obstructive pulmonary disease (COPD).

5. The method of claim 1, further comprising determining the expression level of each gene in the gene set, wherein an increased linear fold change of greater than 1.25 in the expression level of each gene in the gene set relative to the expression level of each gene in the gene set in a control sample is not detected.

6. The method of claim 5, wherein the subject does not have COPD.

7. The method of claim 1, wherein FOS is also a member of the gene set.

8. The method of claim 3, wherein FOS is also a member of the gene set.

9. The method of claim 4, wherein FOS is also a member of the gene set.

10. The method of claim 5, wherein FOS is also a member of the gene set.

11. The method of claim 6, wherein FOS is also a member of the gene set.

12. The method of claim 1, wherein the sample from the subject is obtained from the bronchi walls of at least one of sixth generation, seventh generation, and eighth generation bronchi of the subject.

13. The method of claim 1, wherein the sample from the subject is obtained during fiberoptic bronchoscopy by brushing the bronchi walls of the subject.

14. The method of claim 1, wherein the expression of each gene of the gene set is detected by a process comprising contacting the sample with a probe and measuring hybridization between the probe and mRNA in the sample.

15. The method of claim 1, wherein the expression of each gene of the gene set is detected by a process comprising reverse transcribing mRNA in the sample into cDNA, contacting the cDNA with a probe, and measuring hybridization between the probe and the cDNA.

16. The method of claim 1, wherein the expression of each gene of the gene set is detected by a process comprising contacting the sample with a primer pair, amplifying mRNA in the sample with the primer pair, and measuring amplification of the mRNA.

17. The method of claim 1, wherein the expression of each gene of the gene set is detected by a process comprising reverse transcribing mRNA in the sample into cDNA, contacting the cDNA with a primer pair, amplifying the cDNA with the primer pair, and measuring amplification of the cDNA.

* * * * *